(12) United States Patent
Guilford

(10) Patent No.: US 9,702,009 B2
(45) Date of Patent: *Jul. 11, 2017

(54) URINE GENE EXPRESSION RATIOS FOR DETECTION OF CANCER

(75) Inventor: Parry John Guilford, Dunedin (NZ)

(73) Assignee: PACIFIC EDGE LIMITED, Dunedin (NZ)

( * ) Notice: Subject to any disclaimer, the term of this patent is extended or adjusted under 35 U.S.C. 154(b) by 392 days.

This patent is subject to a terminal disclaimer.

(21) Appl. No.: 12/843,435

(22) Filed: Jul. 26, 2010

(65) Prior Publication Data

US 2011/0151464 A1 Jun. 23, 2011

Related U.S. Application Data

(63) Continuation of application No. 12/221,626, filed on Aug. 5, 2008, now abandoned, which is a continuation of application No. PCT/NZ2007/000029, filed on Feb. 9, 2007.

(30) Foreign Application Priority Data

Feb. 10, 2006 (NZ) ........................................ 545243

(51) Int. Cl.
| | | |
|---|---|---|
| C07H 21/04 | (2006.01) |
| C12Q 1/68 | (2006.01) |
| G01N 33/574 | (2006.01) |
| G06F 19/00 | (2011.01) |

(52) U.S. Cl.
CPC ..... *C12Q 1/6886* (2013.01); *G01N 33/57407* (2013.01); *G06F 19/345* (2013.01); *C12Q 2600/118* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| 5,474,796 | A | * | 12/1995 | Brennan | ............ | B01J 19/0046 |
| | | | | | | 422/547 |
| 2005/0239083 | A1 | * | 10/2005 | Erlander | ............ | 435/6 |
| 2009/0098553 | A1 | * | 4/2009 | Guilford | ............ | 435/6 |
| 2011/0143360 | A1 | * | 6/2011 | Kuroda | ............ | 435/6.14 |
| 2011/0183862 | A1 | * | 7/2011 | Buendia | ............ | 506/9 |

OTHER PUBLICATIONS

Affymetrix GeneCHip Human Mapping 100K Set (Data Sheet, 2004-2005).*
IDS of U.S. Appl. No. 12/221,626.
Office Action dated Feb. 24, 2010 of U.S. Appl. No. 12/221,626.
IDS of U.S. Appl. No. 12/221,626 signed by Examiner Feb. 20, 2010.
Yerushalmi, "ERGL, a novel gene related to ERGIC-53 that is highly expressed in normal and neoplastic prostate and several other tissues," Elsevier, Gene 265 (2001) 55-60.
Stanton, P., "Epidermal growth factor receptor expression by human squamous cell carcinomas of the head and neck, cell lines and xenografts," Macmillan Press Ltd, 1994.
Abbaszadegan, Mohammad R., "Analysis of Multidrug Resistance-associated Protein (MRP) Messenger RNA in Normal and Malignant Hematopoietic Cells," Cancer Research 54, 4676-4679.
Iehle, Catherine, "Differences in sertoid fx-reductase iso-enzymes expression between normal and pathological human prostate tissue," Pergamon, Journal of Steroid Biochemistry and Molecular Biology 68 (1999) 189-195.
Zhao, Hua, "Plasma Levels of Insulin-Like Growth Factor-1 and Binding Protein-3, and Their Association with Bladder Cancer Risk," The Journal of Urology(2003)vol. 169;714-717.
Caillou, Bernard, "Expression of Reduced Nicotinaminde Adenine Dinucleotide Phosphate Exidase (ThoX, LNOX, Duox) Genes and Proteins in Human Thyroid Tissues," The Journal of Clinical Endocrinology & Metabolism (2001) vol. 86, No. 7, The Endocrine Society.
Supplemental Reply to Office Action dated Oct. 28, 2009 in U.S. Appl. No. 12/221,626.
Reply to Office Action dated Oct. 28, 2009 in U.S. Appl. No. 12/221,626.
Office Action dated Aug. 28, 2010 in U.S. Appl. No. 12/221,626.
IDS in U.S. Appl. No. 12/221,626.
Ying-Hao, Sun, "Monitoring gene expression profile changes in bladder transitional cell carcinoma using cDNA microarray," Elsevier, Urologic Oncology 7(2002)207-212.
Thykjaer, Thomas, "Identification of Gene Expression Patterns in Superficial and Invasive Human Bladder Cancer," Cancer Research 61, 2492-2499 Mar. 15, 2001.
Kawakami, Kazumori, "Identification of differentially expressed genes in human bladder cancer through genome-wide gene expression profiling," Oncology Reports 16:521-531, 2006.
Osman, Iman, "Novel Blood Biomarkers of Human Urinary Bladder Cancer," Imagining, Diagnosis, Prognosis, ClinCancerRes 2006:12(11)Jun. 1, 2006.
Dyrskjat, Lars, "Identifying Distinct Classes of Bladder Carcinoma using Microarrays," Nature Genetics, vol. 33, Jan. 2003.
Extended EP Search Report Appl. No. 07715981.2-2402/1991699 PCT/NZ2007/000029.

* cited by examiner

*Primary Examiner* — Jeanine A Goldberg
(74) *Attorney, Agent, or Firm* — D. Benjamin Borson; Borson Law Group, PC

(57) ABSTRACT

This invention relates to methods for determining the presence of cancer in a subject based on the analysis of the expression levels of an under-expressed tumor marker (TM) and at least one other TM. Specifically, this invention relates to the determination of a cancer, particularly bladder cancer, by performing ratio, regression or classification analysis of the expression levels of at least one under-expressed TM, particularly an under-expressed bladder TM (BTM), and at least one over-expressed TM, particularly an over-expressed BTM. In various aspects, the invention relates to kits and devices for carrying out these methods.

12 Claims, 102 Drawing Sheets

| disease state | age | stage | grade |
|---|---|---|---|
| Prostate hyperplasia | 73 | | |
| Urolithiasis | 76 | | |
| normal | 40 | | |
| Prostate hyperplasia | 61 | | |
| Prostate hyperplasia | 78 | | |
| Neurogenic bladder | 72 | | |
| Prostate hyperplasia | 68 | | |
| Urolithiasis | 63 | | |
| normal | 40 | | |
| Neurogenic bladder | 76 | | |
| Prostate hyperplasia | 69 | | |
| normal | 24 | | |
| Prostate hyperplasia | 65 | | |
| normal | 24 | | |
| normal | 37 | | |
| Urolithiasis | 48 | | |
| normal | 28 | | |
| Urolithiasis | 23 | | |
| Neurogenic bladder | 69 | | |
| normal | 28 | | |
| normal | 25 | | |
| Neurogenic bladder | 78 | | |
| Normal | 50 | | |
| normal | 36 | | |
| normal | 34 | | |
| Urolithiasis | 85 | | |
| Neurogenic bladder | 54 | | |
| Normal | 53 | | |
| Prostate hyperplasia | 55 | | |
| Prostate hyperplasia | 76 | | |
| Infection | 19 | | |
| Normal | 64 | | |
| Normal | 62 | | |
| Infection | 62 | | |
| Neurogenic bladder | 83 | | |
| normal lab | 35 | | |
| Urolithiasis | 76 | | |
| normal lab | 40 | | |
| Urolithiasis | 80 | | |
| Prostate hyperplasia | 72 | | |
| Normal | 70 | | |
| Urolithiasis | 63 | | |
| TCC | 82 | - | - |
| TCC | 69 | 2 | 3 |
| TCC | 52 | a | 1-2 |
| Ureteral ca | 77 | 3a | 2-3 |
| TCC | 67 | a | 3 |
| TCC | 57 | a | 3 |
| TCC | 64 | 1 | 1 |
| TCC | 87 | a | 2 |
| TCC | 77 | a | 3 |
| TCC | 37 | a | 2 |
| TCC | 73 | 0 | 0 |
| TCC | 72 | 2 | 3 |

Fig. 1

| disease state | age | stage | grade |
|---|---|---|---|
| TCC | 76 | a | 2 |
| TCC | 74 | a | 3 |
| TCC | 38 | a | 2 |
| TCC | 86 | a | 2 |
| TCC | 77 | a | 3 |
| TCC | 78 | 1 | 3 |
| TCC | 72 | - | - |
| TCC | 72 | 1 | 2 |
| TCC | 71 | a | 2 |
| TCC | 64 | 1 | 1 |
| TCC | 81 | a | 1 |
| TCC | 67 | a | 2 |
| TCC | 75 | a | 2 |
| TCC | 76 | a | 2 |
| TCC | 70 | a | 3 |
| TCC | 78 | is | 3 |
| TCC | 76 | 2a | 3 |
| TCC | 76 | ?ureteral | 2=3 |
| TCC | 68 | 2 | 3 |
| TCC | 78 | 0 | 0 |
| TCC | 78 | 1 | 3 |
| TCC | 70 | a | 2>3 |
| TCC | 77 | 1 | 3>2 |
| TCC | 83 | a | 2 |
| TCC | 83 | a | 1 |

Fig. 1 (continued)

| Name | Symbol | Forward Primer | Seq ID # | Reverse Primer | Seq ID # | Probe | Seq ID # |
|---|---|---|---|---|---|---|---|
| Insulin-like growth factor binding protein 5 | IGFBP5 | AATTGTGACCGCAAAGGAT TCT | 1 | CAGCAGATGCCACGCTTG | 2 | AAGAGAAAGCAGTGCAAA CCTTCCCGT | 3 |
| homeo box A13 | HOXA13 | Taqman(R) Gene Expression Assay Hs00426284_m1 | | | | | |
| midkine (neurite growth-promoting factor 2) | MDK | Taqman(R) Gene Expression Assay Hs00171084_m1 | | | | | |
| Leukotriene B4 12-dehydrogenase | LTB4DH | TATAACAGAACCGGCCGA CTTC | 4 | CCCATTTCAGCAAGTCCTT CA | 5 | CCAGGCCCAGCCCCAGAG ATTG | 6 |
| cell division cycle 2, G1 to S and G2 to M | | | | TGT CTA CCC TTA TAC ACA ACT CCA TAG G | 7 | AGC CGG GAT CTA CCA TAC CCA TTG ACT AAC T | 8 |
| Topoisomerase (DNA) II alpha | TOP2A | CCG CCC AGA CAC CTA CAT TG | 9 | TGT ACA AAC CAG GAA CAA AAG TGA CT | 10 | TTC TGT GGA ATT AGT GAC CCA GCA AAT GTG | 11 |
| BCL2-associated athanogene | BAG1 | Taqman(R) Gene Expression Assay Hs00185390_m1 | | | | | |
| hypothetical protein FLJ21511 | FLJ21511 | Taqman(R) Gene Expression Assay Hs00228221_m1 | | | | | |

Fig. 2

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| ras homolog gene family, member B (RHOB), mRNA | NP_004031.1 | NM_004040.2 | mwghuman3 0K#A:08114 | -2.684592 | 2.13794E-10 | 2.25758E-08 | -10.53678 | 38 | 8789.5 | 4176 | 23 |
| hypothetical protein FLJ21511 (FLJ21511), mRNA | NP_079363.1 | NM_025087.1 | mwghuman3 0K#A:00410 | -2.080908 | 2.54894E-11 | 3.22908E-08 | -8.925773 | 68 | 14455 | 9272.5 | 0 |
| paired box gene 8 (PAX8), transcript variant PAX8A, mRNA | NP_003457.1 | NM_003466.3 | mwghuman3 0K#B:3648 | -1.961896 | 4.71874E-11 | 4.07014E-08 | -6.806281 | 82 | 19419 | 12899.5 | 0 |
| UPF3 regulator of nonsense transcripts homolog A (yeast) (UPF3A), transcript variant 1, mRNA | NP_076387.1 | NM_023011.2 | mwghuman3 0K#A:05295 | -3.84007 | 1.03703E-13 | 3.34027E-08 | -7.811653 | 96.5 | 5663.5 | 1825 | 0 |
| leukotriene B4 12-hydroxydehydrogenase (LTB4DH), mRNA | NP_036344.1 | NM_012212.2 | mwghuman3 0K#B:8886 | -5.034613 | 3.08873E-10 | 1.41836E-07 | -6.436167 | 122.5 | 11340.5 | 3138 | 0 |

Fig. 3

| Gene name/ symbol | protein accession | mRNA ref seq accession. | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| RAB11 family interacting protein 2 (class I) (RAB11FIP2), mRNA | NP_055719.1 | NM_014904.1 | mwghuman3 0K#A:10479 | -1.993629 | 4.57825E-09 | 5.83951E-08 | -7.711624 | 156 | 19636.5 | 12951 | 0 |
| TSC22 domain family, member 1 (TSC22D1), transcript variant 2, mRNA | NP_006013.1 | NM_006022.2 | mwghuman3 0K#A:00577 | -2.133066 | 1.12033E-07 | 1.8543E-07 | -7.698568 | 156.5 | 8415 | 6130 | 1 |
| sulfite oxidase (SUOX), nuclear gene encoding mitochondrial protein, transcript variant 1, mRNA | NP_000447.2 | NM_000456.2 | mwghuman3 0K#A:05512 | -1.622803 | 4.52404E-10 | 5.29156E-09 | -6.728692 | 223 | 11312.5 | 8789.5 | 0 |
| tetratricopeptid e repeat domain 21A (TTC21A), mRNA | NP_665698.1 | NM_145755.1 | mwghuman3 0K#B:6976 | -2.976809 | 2.11314E-07 | 4.28603E-07 | -6.286432 | 225 | 8375.5 | 3870.5 | 1 |

Fig. 3 (continued)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| RAS p21 protein activator (GTPase activating protein) 1 (RASA1), transcript variant 2, mRNA | NP_072178.1 | NM_022650.1 | mwghuman3 0K#A:08292 | -1.947454 | 3.74664E-09 | 2.68048E-06 | -5.99299 | 235 | 6895.5 | 5277.5 | 7 |
| ensembl genscan prediction | | AC024384.3.1 079751.118435.1 | mwghuman3 0K#C:6841 | -2.471322 | 4.47058E-08 | 1.54585E-08 | -6.085076 | 255.5 | 3327.5 | 1537 | |
| ensembl genscan prediction | | AL031689.28.1.94224.1 | mwghuman3 0K#C:0930 | -1.774123 | 6.77812E-09 | 1.13272E-06 | -5.56118 | 288.5 | 4367 | 3218 | |
| geminin, DNA replication inhibitor (GMNN), mRNA | NP_056979.1 | NM_015895.3 | mwghuman3 0K#A:03435 | -2.046753 | 1.94848E-07 | 4.07898E-06 | -5.89032 | 311 | 11844 | 8413.75 | 2 |
| fatty acid binding protein 1, liver (FABP1), mRNA | NP_001434.1 | NM_001443.1 | mwghuman3 0K#A:09506 | -1.885247 | 2.20148E-06 | 6.83453E-07 | -6.750762 | 312.5 | 25595 | 19500.75 | 0 |
| v-jun sarcoma virus 17 oncogene homolog (avian) (JUN), mRNA | NP_002219.1 | NM_002228.3 | mwghuman3 0K#A:04848 | -3.222311 | 6.2171E-07 | 4.59274E-06 | -6.363849 | 318.5 | 12139 | 5321.5 | 11 |

Fig. 3 (continued)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| transmembrane and coiled-coil domains 4 (TMCO4), mRNA | NP_859070.2 | NM_181718.2 | mwghuman3 OK#B:3094 | -1.799143 | 8.41415E-09 | 3.21175E-06 | -5.702577 | 322.5 | 4584.5 | 3158 | 5 |
| ensembl genscan prediciton | | AP002080.2.3 7398.74587.1 | mwghuman3 OK#C:4035 | -1.860121 | 5.75299E-08 | 1.01121E-07 | -7.300326 | 332.5 | 4972.5 | 2643 | |
| synaptotagmin-like 2 (SYTL2), transcript variant b, mRNA | NP_115755.2 | NM_032379.3 | mwghuman3 OK#B:9411 | -2.343357 | 4.07528E-10 | 9.87494E-09 | -7.993821 | 342 | 19820 | 12053.5 | 0 |
| cyclin G1 (CCNG1), transcript variant 1, mRNA | NP_004051.1 | NM_004060.3 | mwghuman3 OK#B:5261 | -1.83737 | 2.79204E-08 | 4.64998E-07 | -6.214778 | 365 | 8269.5 | 4453 | 7 |
| F-box protein 34 (FBXO34), mRNA | NP_060413.2 | NM_017943.2 | mwghuman3 OK#B:4885 | -1.801846 | 1.15594E-08 | 1.13272E-06 | -7.185506 | 365.5 | 17957.5 | 13192.75 | 5 |
| hypothetical protein xp_097916 loc150582 | | XM_097916 | mwghuman3 OK#B:6228 | -2.291304 | 2.69775E-08 | 3.84322E-06 | -5.299383 | 375 | 3591 | 1276 | |
| RNA pseudouridylate synthase domain containing 4 (RPUSD4), mRNA | NP_116184.1 | NM_032795.1 | mwghuman3 OK#B:8888 | -1.588438 | 2.0145E-10 | 1.14227E-08 | -8.404434 | 407 | 15747.5 | 11247 | 5 |

Fig. 3 (continued)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| WD repeat domain 33 (WDR33), transcript variant 2, mRNA | NP_001006 23.1 | NM_001006 22.1 | mwghuman3 OK#A:08115 | -1.765322 | 1.47232E-07 | 1.45307E-06 | -6.190057 | 413 | 14876 | 13787.5 | 8 |
| FLJ20859 gene (FLJ20859), transcript variant 1, mRNA | NP_0010251 62.1 | NM_0010299 91.1 | mwghuman3 OK#A:10470 | -1.706985 | 8.133E-08 | 1.13272E-06 | -6.182853 | 420.5 | 3781 | 2693.75 | |
| activating transcription factor 3 (ATF3), transcript variant 2, mRNA | NP_004015.3 | NM_004024.3 | mwghuman3 OK#A:00588 | -3.134291 | 8.40437E-08 | 1.51698E-07 | -7.446028 | 421 | 13832.5 | 5301.25 | 3 |
| cytochrome P450, family 3, subfamily A, polypeptide 5 (CYP3A5), mRNA | NP_000768.1 | NM_000777.2 | mwghuman3 OK#A:04559 | -2.482182 | 7.0225E-08 | 1.9772E-06 | -4.813425 | 451.5 | 20350.5 | 12190.5 | 2 |
| ensembl genscan prediction | | AL161725.13. 1.181179.3 | mwghuman3 OK#C:3443 | -1.953495 | 1.18555E-09 | 9.24336E-08 | -5.881512 | 455 | 2738.5 | 1799 | |
| KIT ligand (KITLG), transcript variant b, mRNA | NP_000890.1 | NM_000899.3 | mwghuman3 OK#A:07355 | -4.28251 | 3.8867E-08 | 7.23184E-07 | -5.884133 | 470 | 19497 | 10599.75 | 2 |

Fig. 3 (continued)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| decay accelerating factor for complement (CD55, Cromer blood group system) (DAF), mRNA | NP_000565.1 | NM_000574.2 | mwghuman3 OK#A:08760 | -2.146033 | 1.44112E-06 | 6.53282E-06 | -5.668184 | 471.5 | 9808.5 | 4753.25 | 10 |
| solute carrier family 25 (mitochondrial carrier; phosphate carrier), member 23 (SLC25A23), mRNA | NP_077008.2 | NM_024103.2 | mwghuman3 OK#A:055530 | -1.465915 | 7.79426E-09 | 8.80903E-07 | -5.741772 | 497 | 16285.5 | 12418.75 | 4 |
| wingless-type MMTV Integration site family, member 2B (WNT2B), transcript variant WNT-2B1, mRNA | NP_004178.2 | NM_004185.2 | mwghuman3 OK#A:056896 | -10.745275 | 2.92382E-12 | 3.19726E-07 | -6.175471 | 501 | 10718 | 2016.25 | 0 |
| protocadherin gamma subfamily A, 12 (PCDHGA12), transcript variant 1, mRNA | NP_003726.1 | NM_003735.2 | mwghuman3 OK#A:03393 | -2.070447 | 2.89557E-07 | 6.92439E-06 | -4.862742 | 511 | 2537 | 1931.5 | 0 |

Fig. 3 (continued)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| ensembl genscan prediction | | AC010828.3. 125573.1581 93.2 | mwghuman3 OK#C:4737 | -1.679455 | 2.34945E-07 | 6.18322E-07 | -5.341693 | 511 | 26962 | 25287.75 | |
| olfactory receptor, family 1, subfamily D, member 5 (OR1D5), mRNA | NP_055381.1 | NM_014566.1 | mwghuman3 OK#A:06766 | -1.640751 | 5.38884E-08 | 4.32856E-06 | -5.134756 | 539.5 | 1644 | 1134 | 0 |
| G protein-coupled receptor 126 (GPR126), transcript variant b1, mRNA | NP_940971.1 | NM_198569.1 | mwghuman3 OK#B:2989 | -2.181735 | 3.9002E-07 | 1.05021E-05 | -5.047901 | 549 | 15985.5 | 8040.75 | 0 |
| similar to be40865.4 novel protein dmpk-like cdc42-binding kinase beta cdc42bpb loc144850 | | XM_090553 | mwghuman3 OK#B:9158 | -4.265957 | 2.38683E-08 | 5.29006E-07 | -6.259229 | 573 | 1784 | 632 | |
| ubiquitin specific peptidase 9, Y-linked (fat facets-like, Drosophila) (USP9Y), mRNA | NP_004845.2 | NM_004654.3 | mwghuman3 OK#A:10655 | -1.584085 | 3.40815E-07 | 8.23838E-08 | -5.287284 | 587 | 10035.5 | 7858.25 | 1 |

Fig. 3 (continued)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| ensembl genscan prediction | | AC022554.2.1 1725.14587.1 | mwghuman3 OK#C:7523 | -2.800527 | 1.74508E-07 | 8.41199E-07 | -5.902891 | 597 | 3330 | 1288 | |
| solute carrier family 35 (CMP-sialic acid transporter), member A1 (SLC35A1), mRNA | NP_006407.1 | NM_006416.2 | mwghuman3 OK#B:6203 | -1.879113 | 1.20877E-08 | 5.48118E-06 | -5.287694 | 606 | 20639 | 15438.75 | 1 |
| cell line sc30 t receptor alpha chain v-j junctional region tcr v 29.1 j 11 coding sequence reported spans from nucleotide position | | U14083 | mwghuman3 OK#B:9790 | -2.442854 | 9.94216E-08 | 1.14277E-08 | -7.365379 | 617 | 6673 | 2661.5 | |
| chromosome 2 open reading frame 33 (C2orf33), mRNA | NP_084579.3 | NM_020194.4 | mwghuman3 OK#A:06988 | -1.615311 | 3.24982E-07 | 9.24336E-06 | -5.392632 | 624 | 11555.5 | 8888.25 | 4 |
| ensembl genscan prediction | | AC073108.7.1 14033.192530.1 | mwghuman3 OK#C:4991 | -2.137812 | 1.453E-05 | 1.08394E-08 | -6.345675 | 650.5 | 9983.5 | 5676.75 | |

Fig. 3 (continued)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| UDP-N-acetyl-alpha-D-galactosamine: polypeptide N-acetylgalactosaminyltransferase 7 (GalNAc-T7) (GALNT7), mRNA | NP_059119.1 | NM_017423.1 | mwghuman3 OK#A:01420 | -1.401046 | 7.53042E-08 | 1.13272E-06 | -6.143981 | 658.5 | 10573 | 8997.75 | 2 |
| chromosome 11 open reading frame 1 (C11orf1), mRNA | NP_073598.1 | NM_022761.1 | mwghuman3 OK#A:01834 | -1.81726 | 1.38032E-08 | 1.22937E-05 | -5.104229 | 673.5 | 12025.5 | 9585.25 | 0 |
| heterogeneous nuclear ribonucleoprotein H2 (H') (HNRPH2), transcript variant 1, mRNA | NP_062643.1 | NM_019597.3 | mwghuman3 OK#A:08547 | -2.03901 | 2.40085E-08 | 8.16248E-06 | -5.465662 | 684 | 777 | 472 | 9 |
| Werner syndrome (WRN), mRNA | NP_000544.1 | NM_000553.2 | mwghuman3 OK#A:03163 | -1.605462 | 7.49708E-08 | 6.16248E-06 | -4.681771 | 696 | 4585 | 4351.25 | 3 |
| ensembl genscan prediction | | AC040160.3.6 1245.138821.5 | mwghuman3 OK#C:7317 | -4.953847 | 7.54477E-12 | 1.43666E-08 | -6.602868 | 706.5 | 4523.5 | 744.5 | |

Fig. 3 (continued)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| adducin 3 (gamma) (ADD3), transcript variant 1, mRNA | NP_058432.1 | NM_016824.3 | mwghuman3 0K#B:5211 | -2.092475 | 1.34331E-05 | 1.16158E-05 | -5.883251 | 718 | 7668.5 | 4808.75 | 8 |
| hydroxysteroid dehydrogenase like 2 (HSDL2), mRNA | NP_115679.2 | NM_032303.2 | mwghuman3 0K#B:3888 | -2.1317 | 9.39999E-07 | 5.81228E-06 | -5.58267 | 732.5 | 7276.5 | 5055 | 2 |
| DNA-damage-inducible transcript 4 (DDIT4), mRNA | NP_061931.1 | NM_019058.2 | mwghuman3 0K#B:2115 | -2.860775 | 6.68634E-05 | 5.16818E-06 | -5.869252 | 750 | 10960.5 | 5082.75 | 12 |
| RNA binding protein, autoantigenic (hnRNP-associated with lethal yellow homolog (mouse)) (RALY), transcript variant 1, mRNA | NP_057951.1 | NM_016732.1 | mwghuman3 0K#A:06376 | -1.801576 | 1.7076E-07 | 4.32856E-06 | -4.392163 | 750.5 | 977 | 386.5 | 28 |

Fig. 3 (continued)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| acyl-CoA synthetase medium-chain family member 3 (ACSM3), transcript variant 1, mRNA | NP_005613.2 | NM_005622.3 | mwghuman3 0K#B:8076 | -1.967123 | 1.7751E-05 | 7.33836E-06 | -5.050721 | 765.5 | 18908.5 | 12252.25 | 3 |
| BCL2-associated athanogene (BAG1), mRNA | NP_004314.3 | NM_004323.3 | mwghuman3 0K#A:08581 | -2.525417 | 2.13163E-08 | 5.29008E-07 | -5.934904 | 776 | 9031 | 4503.5 | 1 |
| neural precursor cell expressed, developmentally down-regulated 4 (NEDD4), transcript variant 1, mRNA | NP_006145.1 | NM_006154.1 | mwghuman3 0K#B:7862 | -1.800818 | 3.7763E-06 | 8.23334E-06 | -5.249282 | 781 | 15497 | 12075 | 2 |
| chromosome 7 open reading frame 19 (C7orf19), mRNA | NP_116220.1 | NM_032831.1 | mwghuman3 0K#B:2324 | -1.780735 | 4.63759E-06 | 0.000016624 | -5.43532 | 783 | 11586.5 | 6704.75 | 16 |
| calpain 13 (CAPN13), mRNA | NP_653176.2 | NM_144575.2 | mwghuman3 0K#B:8754 | -1.542431 | 4.41704E-06 | 5.81228E-06 | -4.843249 | 808.5 | 23318 | 19953.5 | 0 |
| homeo box B2 (HOXB2), mRNA | NP_002136.1 | NM_002145.2 | mwghuman3 0K#A:01639 | -2.702849 | 2.94488E-11 | 5.08294E-08 | -8.774876 | 814.5 | 11537.5 | 6408 | 3 |

Fig. 3 (continued)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| coiled-coil domain containing 28A (CCDC28A), mRNA | NP_056254.1 | NM_015439.2 | mwghuman3 0K#B:3128 | -1.960606 | 1.97345E-06 | 5.49118E-06 | -5.330597 | 826 | 19022 | 14223.75 | 4 |
| myofibrillogene sis regulator 1 (MR-1), transcript variant 1, mRNA | NP_058303.2 | NM_015488.3 | mwghuman3 0K#B:3179 | -1.526799 | 1.22924E-05 | 6.92439E-06 | -5.874478 | 832 | 13007 | 10755.75 | 8 |
| guanine nucleotide binding protein (G protein), beta polypeptide 2-like 1 (GNB2L1), mRNA | NP_006089.1 | NM_006098.4 | mwghuman3 0K#C:0841 | -1.789085 | 2.16356E-06 | 4.35419E-05 | -4.900058 | 844.5 | 1710 | 1178 | 106 |
| spectrin repeat containing, nuclear envelope 1 (SYNE1), transcript variant beta, mRNA | NP_056108.1 | NM_015293.1 | mwghuman3 0K#B:9104 | -1.414534 | 7.52733E-07 | 3.02433E-06 | -5.983107 | 851 | 20159.5 | 17233.75 | 64 |
| ensembl genscan prediction | | AL021155.1.1 .107603.5 | mwghuman3 0K#C:7334 | -1.766409 | 2.12121E-06 | 2.01355E-05 | -4.468876 | 853 | 1264 | 847.5 | |

Fig. 3 (continued)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| bone morphogenetic protein receptor, type IA (BMPR1A), mRNA | NP_004320.2 | NM_004329.2 | mwghuman3 0K#A:02464 | -1.558832 | 2.22237E-07 | 1.22937E-05 | -4.618211 | 874.5 | 5116 | 5037.5 | 4 |
| IQ motif containing B1 (IQCB1), transcript variant 1, mRNA | NP_0010188 64.1 | NM_0010235 70.1 | mwghuman3 0K#B:4020 | -1.846898 | 2.79485E-05 | 1.62908E-05 | -5.169855 | 882.5 | 10922 | 8773.5 | 2 |
| ensembl genscan prediction | | AC069502.8.1 .18380.1 | mwghuman3 0K#C:3683 | -1.484573 | 8.94397E-07 | 2.53657E-05 | -4.951029 | 901 | 21078 | 19035 | |
| similar to death-associated protein (LOC92196), mRNA | NP_0010179 20.1 | NM_0010179 20.1 | mwghuman3 0K#B:8718 | -2.553467 | 5.76345E-07 | 7.76152E-07 | -5.221107 | 907 | 23255 | 15888 | 0 |
| ensembl genscan prediction | | AC012203.4.1 05191.123571 .1 | mwghuman3 0K#C:4578 | -1.438718 | 3.21936E-05 | 4.85862E-07 | -5.989899 | 907 | 27071.5 | 25867.5 | |
| ensembl genscan prediction mwg oligo matches these RefSeq numbers NM_000980 | | AL158153.8.4 5139.113162. 3 | mwghuman3 0K#C:2173 | -2.089238 | 4.80586E-07 | 4.32856E-06 | -5.395407 | 908.5 | 1290 | 1010.25 | |

Fig. 3 (continued)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| growth arrest and DNA-damage-inducible, alpha (GADD45A), mRNA | NP_001915.1 | NM_001924.2 | mwghuman3 OK#A:04348 | -1.68216 | 7.53908E-08 | 2.67916E-05 | -4.924921 | 916.5 | 11634.5 | 8596.75 | 3 |
| stress 70 protein chaperone, microsome-associated, 60kDa (STCH), mRNA | NP_008879.3 | NM_006948.4 | mwghuman3 OK#A:05064 | -1.761334 | 4.58163E-05 | 1.72268E-05 | -5.784774 | 916.5 | 10794 | 6231.25 | 5 |
| ensembl genscan prediction | | Z84474.1.1.1 07526.2 | mwghuman3 OK#C:0911 | -1.884499 | 1.62444E-08 | 2.23413E-08 | -5.434325 | 933.5 | 1974 | 1488.5 | |
| family with sequence similarity 44, member B (FAM44B), mRNA | NP_612378.1 | NM_138369.1 | mwghuman3 OK#B:4192 | -1.357114 | 7.91633E-07 | 1.64431E-06 | -6.047548 | 942.5 | 15308.5 | 13004.75 | 1 |
| ensembl genscan prediction | | AC078789.15. 1.55074.2 | mwghuman3 OK#C:6283 | -1.786484 | 1.80836E-06 | 3.70631E-05 | -4.861731 | 948 | 25553.5 | 22990.75 | |
| citrate lyase beta like (CLYBL), transcript variant 1, mRNA | NP_612124.3 | NM_138280.3 | mwghuman3 OK#B:8855 | -1.444822 | 1.17336E-06 | 5.16818E-06 | -5.775319 | 953 | 21231 | 19330.25 | 1 |

Fig. 3 (continued)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| ensembl genscan prediction | | AP001015.3.6 6054.1156655.1 | mwghuman3 OK#C:3998 | -1.709242 | 1.48259E-07 | 7.36585E-05 | -4.504002 | 972.5 | 3374.5 | 2739.5 | |
| ensembl genscan prediction | | AL159169.14. 1.86155.2 | mwghuman3 OK#C:4465 | -1.474035 | 8.90434E-07 | 3.25437E-06 | -5.020854 | 996.5 | 28575 | 28030 | |
| chromosome 6 open reading frame 130 (C6orf130), mRNA | NP_669500.1 | NM_145063.2 | mwghuman3 OK#B:4652 | -1.874298 | 1.77778E-05 | 3.32844E-05 | -4.846371 | 1011.5 | 14804 | 10754.75 | 3 |
| methyltransfera se like 1 (METTL1), transcript variant 1, mRNA | NP_005362.1 | NM_005371.3 | mwghuman3 OK#A:00607 | -1.464425 | 1.73108E-07 | 5.48118E-06 | -5.447819 | 1026 | 943 | 645.5 | 2 |
| nucleosome assembly protein 1-like 4 (NAP1L4), mRNA | NP_005960.1 | NM_005969.3 | mwghuman3 OK#A:00706 | -1.902267 | 1.44614E-05 | 6.99321E-05 | -4.962357 | 1042.5 | 10336.5 | 8978.5 | 12 |
| tumor protein D52 (TPD52), transcript variant 3, mRNA | NP_005070.1 | NM_005079.2 | mwghuman3 OK#A:05633 | -1.55805 | 1.79544E-06 | 3.15409E-05 | -4.599069 | 1070 | 19033 | 14646.75 | 4 |
| EH-domain containing 4 (EHD4), mRNA | NP_644670.1 | NM_139265.2 | mwghuman3 OK#B:5911 | -1.64935 | 1.97898E-05 | 3.70831E-05 | -4.903865 | 1077 | 12134 | 9167.5 | 4 |

Fig. 3 (continued)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| fibroblast growth factor receptor 4 (FGFR4), transcript variant 2, mRNA | NP_075252.2 | NM_022963.2 | mwghuman3 OK#B:8174 | -2.638426 | 2.02402E-06 | 3.21175E-06 | -6.251766 | 1087.5 | 17098 | 9702.5 | 0 |
| KIAA0674 (KIAA0674), mRNA | XP_376903.2 | XM_376903.2 | mwghuman3 OK#B:0240 | -1.362278 | 3.88739E-08 | 3.62055E-08 | -5.432041 | 1092.5 | 10744 | 9097.25 | 4 |
| chromosome 16 bac clone cit987sk-a-363e6 | | U91321 | mwghuman3 OK#B:5375 | -1.568388 | 5.91844E-05 | 6.53282E-08 | -6.349455 | 1114.5 | 10576.5 | 6083.25 | |
| ensembl genscan prediction | | AC073610.11. 63494.102478.3 | mwghuman3 OK#C:1337 | -1.828108 | 1.68631E-08 | 1.30096E-05 | -5.253574 | 1114.5 | 1434.5 | 737 | |
| androgen receptor (AR), transcript variant 1, mRNA | NP_000035.2 | NM_000044.2 | mwghuman3 OK#A:01003 | -1.575215 | 1.18973E-07 | 1.54035E-05 | -4.291628 | 1120.5 | 18067.5 | 15252.5 | 0 |
| thyroid transcription factor 1 (TITF1), mRNA | NP_003308.1 | NM_003317.3 | mwghuman3 OK#A:07197 | -1.466987 | 8.57665E-07 | 1.54585E-06 | -6.023277 | 1124.5 | 2139 | 1026.25 | 0 |

Fig. 3 (continued)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| spectrin repeat containing, nuclear envelope 1 (SYNE1), transcript variant longest, mRNA | NP_892006.1 | NM_182961.1 | mwghuman3 OK#C:2340 | -1.440164 | 8.37872E-05 | 2.15085E-05 | -5.805222 | 1124.5 | 26092.5 | 21681.5 | 64 |
| ensembl genscan prediction | | AC019084.7.9 3515.134992.2 | mwghuman3 OK#C:5482 | -1.55364 | 1.48692E-08 | 7.77583E-06 | -5.043927 | 1126.5 | 8785.5 | 8789.5 | |
| ensembl genscan prediction | | AC026235.12. 9210.157122.4 | mwghuman3 OK#C:3969 | -1.693854 | 8.74991E-08 | 0.000122 803 | -4.393663 | 1136.5 | 804 | 493.5 | |
| ensembl genscan prediction | | AP002840.1.9 8623.121675.1 | mwghuman3 OK#C:59950 | -1.784079 | 2.98992E-05 | 7.75722E-05 | -4.89759 | 1156 | 16893.5 | 14033.25 | |
| CDC-like kinase 1 (CLK1), transcript variant 1, mRNA | NP_004062.2 | NM_004071.2 | mwghuman3 OK#A:07840 | -2.034707 | 6.15281E-05 | 6.99321E-05 | -5.146308 | 1157.5 | 12199 | 7934.75 | 4 |
| lipin 1 (LPIN1), mRNA | NP_663731.1 | NM_145693.1 | mwghuman3 OK#B:8172 | -1.851742 | 1.40757E-07 | 2.98753E-05 | -4.301729 | 1159.5 | 3757 | 2609 | 2 |
| lamin A/C (LMNA), transcript variant 2, mRNA | NP_005563.1 | NM_005572.2 | mwghuman3 OK#A:08943 | -1.724223 | 9.63727E-05 | 5.67358E-05 | -5.305029 | 1162.5 | 4447 | 3295 | 10 |
| ensembl genscan prediction | | AC079456.15. 119608.15149 0.1 | mwghuman3 OK#C:3309 | -1.38662 | 6.38081E-08 | 4.32856E-06 | -6.439308 | 1169.5 | 26755.5 | 26493.5 | |

Fig. 3 (continued)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| similar to riken cdna 1500002b03 clone mgc12928 image:4284414 | | BC007768 | mwghuman3 0K#B:4242 | -1.518352 | 5.21322E-08 | 3.51403E-05 | -4.463332 | 1171 | 21159 | 20375 | |
| ensembl genscan prediction | | AC027086.2.2 3033.31927.1 | mwghuman3 0K#C:8982 | -1.659003 | 1.16113E-11 | 3.62785E-07 | -6.295271 | 1172.5 | 2767 | 2062.75 | . |
| hyaluronogluco saminidase 3 (HYAL3), mRNA | NP_003540.2 | NM_003549.2 | mwghuman3 0K#A:09529 | -2.01277 | 6.70905E-08 | 1.16156E-05 | -4.684969 | 1175 | 4326 | 3464.5 | 4 |
| ensembl genscan prediction VprBP protein (VprBP), mRNA | | AC083822.10. 126484.12912 2.1 | mwghuman3 0K#C:9101 | -1.479802 | 6.01319E-08 | 2.53667E-05 | -4.526859 | 1177 | 22091.5 | 20578.5 | |
| nuclear RNA export factor 1 (NXF1), mRNA | NP_055518.1 | NM_014703.1 | mwghuman3 0K#B:0332 | -1.720326 | 3.28082E-05 | 2.40122E-05 | -5.246883 | 1178 | 17312.5 | 14031 | 0 |
| empty spiracles homolog 2 (Drosophila) (EMX2), mRNA | NP_006353.2 | NM_006362.3 | mwghuman3 0K#B:1047 | -1.485619 | 7.48559E-05 | 1.62908E-05 | -5.178445 | 1195.5 | 15210 | 14049.75 | 20 |
| homeo box D8 (HOXD8), mRNA | NP_004089.1 | NM_004088.2 | mwghuman3 0K#B:9279 | -1.745088 | 8.49886E-09 | 5.64117E-07 | -5.709572 | 1199.5 | 19380 | 10749.25 | 0 |
| | NP_062458.1 | NM_019558.2 | mwghuman3 0K#B:3465 | -1.41555 | 6.70306E-08 | 2.1019E-06 | -5.674131 | 1208 | 9672.5 | 7512.25 | 0 |

Fig. 3 (continued)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| pro2591 predicted protein of hq2591 | | AF119666 | mwghuman3 0K#B:1001 | -1.487408 | 7.83971E-05 | 1.30297E-05 | -4.929888 | 1212 | 27543.5 | 26699 | 0 |
| ensembl genscan prediction | | AC016432.3.1 6946.19371.1 | mwghuman3 0K#C:8058 | -3.528975 | 4.33482E-13 | 5.08294E-08 | -6.731611 | 1216.5 | 3962.5 | 1303 | |
| ensembl genscan prediction | | AF286885.1.7 5372.1158543 | mwghuman3 0K#C:7800 | -1.83051 | 1.14443E-05 | 5.11795E-05 | -4.359199 | 1218 | 21183.5 | 21224.5 | |
| zinc finger protein 25 (KOX 19) (ZNF25), mRNA | NP_858448.1 | NM_145011.2 | mwghuman3 0K#C:1648 | -1.473477 | 6.43814E-09 | 4.35863E-07 | -5.84264 | 1253.5 | 21026.5 | 19171 | 1 |
| zinc finger protein 626 (ZNF626), mRNA | NP_860340.1 | NM_145297.2 | mwghuman3 0K#B:4148 | -1.773183 | 2.31455E-06 | 6.63845E-05 | -4.294361 | 1266 | 14806.5 | 10341 | 1 |
| growth arrest and DNA-damage-inducible, beta (GADD45B), mRNA | NP_056490.1 | NM_015675.1 | mwghuman3 0K#A:00537 | -1.850707 | 0.000200032 | 2.03519E-05 | -5.558029 | 1270.5 | 13309 | 8615.5 | 5 |
| nebulette (NEBL), transcript variant 1, mRNA | NP_006384.1 | NM_006393.1 | mwghuman3 0K#A:10459 | -1.513391 | 1.95755E-05 | 3.15409E-05 | -4.789714 | 1276 | 22836 | 20052.5 | 1 |

Fig. 3 (continued)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| hypothetical protein pro2832 pro2832 | | NM_018541 | mwghuman3 0K#A:00371 | -1.457098 | 3.06355E-05 | 6.99321E-05 | -5.164495 | 1289.5 | 16692.5 | 14266.5 | |
| ring finger protein 44 (RNF44), mRNA | NP_055716.1 | NM_014901.4 | mwghuman3 0K#A:10660 | -1.353366 | 7.76079E-07 | 2.37433E-06 | -5.842265 | 1292 | 6288.5 | 4664.5 | 1 |
| REX1, RNA exonuclease 1 homolog (S. cerevisiae) (REXO1), mRNA | NP_065746.2 | NM_020695.2 | mwghuman3 0K#B:8218 | -1.36867 | 1.73225E-05 | 2.38069E-05 | -5.111364 | 1305.5 | 4933 | 3309.5 | 6 |
| pyrimidinergic receptor P2Y, G-protein coupled, 4 (P2RY4), mRNA | NP_002556.1 | NM_002565.3 | mwghuman3 0K#A:00433 | -1.732075 | 5.0193E-08 | 2.88048E-06 | -5.510614 | 1309 | 18307 | 12139.5 | 0 |
| ensembl genscan prediction | | AL023804.2.1 96460.1 | mwghuman3 0K#C:5405 | -1.533348 | 1.03637E-06 | 2.808E-05 | -4.693772 | 1313 | 28610 | 27980.5 | |
| ensembl genscan prediction | | AL139823.3.4 9422.51911.1 | mwghuman3 0K#C:8800 | -1.894452 | 4.41409E-05 | 0.000129 14 | -4.650026 | 1320 | 11214.5 | 7548 | |
| similar to hypothetical protein (LOC440804), mRNA | XP_036936.3 | XM_036936.3 | mwghuman3 0K#B:4832 | -4.049648 | 5.38047E-11 | 1.51698E-07 | -6.579174 | 1332 | 3647 | 996.5 | 0 |

Fig. 3 (continued)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| chromosome X open reading frame 41 (CXorf41), mRNA | NP_775765.1 | NM_173494.1 | mwghuman3 0K#C:1526 | -1.448331 | 1.77872E-05 | 2.53657E-05 | -5.140193 | 1334 | 27414 | 24082.75 | 0 |
| chromosome 20 open reading frame 152 (C20orf152), mRNA | NP_543024.1 | NM_080834.1 | mwghuman3 0K#B:3251 | -1.948612 | 6.84261E-06 | 1.82138E-05 | -4.987586 | 1349 | 10775 | 8652.5 | 0 |
| ensembl genscan prediction | | AL380766.11. 35886.142382 .1 | mwghuman3 0K#C:4546 | -1.516487 | 5.60886E-05 | 4.81914E-05 | -4.842988 | 1352 | 28469.5 | 27078.25 | |
| phosphorylase, glycogen; liver (Hers disease, glycogen storage disease type VI) (PYGL), mRNA | NP_002854.3 | NM_002863.3 | mwghuman3 0K#A:04342 | -2.190281 | 5.14475E-06 | 0.000269 936 | -4.316788 | 1388.5 | 10289.5 | 7222 | 21 |
| ensembl genscan prediction | | AC013764.3.1 17501.157349 .1 | mwghuman3 0K#C:3927 | -1.871849 | 8.77886E-06 | 7.36585E-05 | -4.28185 | 1395.5 | 1205 | 826.5 | |
| follistatin-like 4 (FSTL4), mRNA | NP_055897.1 | NM_015082.1 | mwghuman3 0K#B:0510 | -1.544042 | 4.79688E-05 | 4.35419E-05 | -4.607854 | 1405.5 | 17051 | 12319 | 0 |

Fig. 3 (continued)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| chromosome 14 open reading frame 168 (C14orf168), mRNA | NP_113615.1 | NM_031427.1 | mwghuman3 0K#B:4011 | -1.512002 | 1.58095E-05 | 5.97939E-05 | -4.895177 | 1414 | 15738 | 14705.75 | 1 |
| aldehyde dehydrogenas e 7 family, member A1 (ALDH7A1), mRNA | NP_001173.1 | NM_001182.2 | mwghuman3 0K#A:08361 | -1.837545 | 4.80787E-07 | 0.000105 508 | -3.903403 | 1433 | 20103.5 | 14345.5 | 2 |
| ensembl genscan prediction | | AC010904.9.3 83.204857.4 | mwghuman3 0K#C:7433 | -1.40403 | 4.74755E-05 | 3.07684E-05 | -4.852328 | 1444 | 27423.5 | 25979.25 | |
| kallikrein 8 (neuropsin/ova sin) (KLK8), transcript variant 2, mRNA | NP_853086.1 | NM_144505.1 | mwghuman3 0K#B:0129 | -2.091505 | 3.56009E-06 | 2.81655E-06 | -5.991679 | 1449.5 | 8391 | 8488 | 0 |
| leucine zipper, down-regulated in cancer 1-like (LDOC1L), mRNA | NP_115683.2 | NM_032287.2 | mwghuman3 0K#B:8710 | -1.501021 | 2.8566E-06 | 1.22937E-05 | -4.280727 | 1454.5 | 16509.5 | 14157 | 0 |
| two pore segment channel 1 (TPCN1), mRNA | NP_060371.2 | NM_017901.3 | mwghuman3 0K#B:7759 | -1.497443 | 4.32588E-06 | 3.32844E-05 | -4.567011 | 1460.5 | 17545 | 11635.75 | 8 |

Fig. 3 (continued)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| hypothetical protein MGC11242, (MGC11242), mRNA | NP_077298.1 | NM_024320.2 | mwghuman3 0K#A:05130 | -1.527839 | 2.70218E-05 | 1.72268E-05 | -4.004461 | 1463.5 | 17585 | 13134.5 | 0 |
| phosphofurin acidic cluster sorting protein 1 (PACS1), mRNA | NP_080496.2 | NM_018026.2 | mwghuman3 0K#B:7703 | -1.494259 | 5.23361E-05 | 7.36585E-05 | -4.899266 | 1482.5 | 9352 | 7757.75 | 19 |
| hypothetical protein xp_036408 loc91138 | | XM_036408 | mwghuman3 0K#B:8080 | -1.533764 | 1.02161E-05 | 4.59223E-05 | -4.93538 | 1486.5 | 15372.5 | 14852 | |
| KIAA1274 (KIAA1274), mRNA | NP_055246.1 | NM_014431.1 | mwghuman3 0K#B:8047 | -1.41942 | 7.87044E-05 | 2.27276E-05 | -5.659345 | 1488.5 | 8059 | 5085 | 0 |
| ensembl genscan prediction | | AC080851.1.9 901.366661.2 | mwghuman3 0K#C:6027 | -1.525691 | 2.39913E-05 | 7.36585E-05 | -4.620984 | 1489.5 | 21092 | 20253 | |
| hypothetical protein FLJ13111 (FLJ13111), mRNA | NP_079358.1 | NM_025082.1 | mwghuman3 0K#A:02890 | -1.488988 | 3.89098E-05 | 7.08197E-05 | -4.489468 | 1494 | 4861 | 7579.25 | 10 |
| glycophorin C (Gerbich blood group) (GYPC), transcript variant 1, mRNA | NP_002092.1 | NM_002101.3 | mwghuman3 0K#A:01278 | -1.628829 | 9.49623E-06 | 0.000135784 | -4.110107 | 1502 | 8042 | 6771 | 2 |

Fig. 3 (continued)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| hypothetical LOC401510 (LOC401510), mRNA | XP_378843.2 | XM_378843.2 | mwghuman3 0K#B:8807 | -1.402822 | 3.03035E-06 | 0.000105 508 | -4.471835 | 1504 | 13882.5 | 11233.25 | 0 |
| ensembl genscan prediction | | AC068282.4.1 68870.201224 .1 | mwghuman3 0K#C:14421 | -1.273285 | 1.4683E-06 | 4.32856E-06 | -5.673395 | 1505.5 | 4650 | 3232.25 | |
| phospholipase A2, group IVA (cytosolic, calcium-dependent) (PLA2G4A), mRNA | NP_077734.1 | NM_024420.1 | mwghuman3 0K#C:2728 | -1.656839 | 1.32347E-05 | 2.82936E-05 | -4.522341 | 1508.5 | 17887.5 | 14140.5 | 5 |
| plastin 1 (I isoform) (PLS1), mRNA | NP_002661.1 | NM_002670.1 | mwghuman3 0K#A:06551 | -1.626206 | 5.67628E-05 | 2.98753E-05 | -4.852263 | 1509.5 | 20943 | 14040.5 | 1 |
| neurobeachin-like 1 (NBEAL1), mRNA | NP_945183.1 | NM_199945.1 | mwghuman3 0K#C:8646 | -1.528965 | 7.51176E-06 | 2.82936E-05 | -5.005478 | 1511.5 | 23554.5 | 20060 | 3 |
| alcohol dehydrogenas e 4 (class II), pi polypeptide (ADH4), mRNA | NP_000661.2 | NM_000670.3 | mwghuman3 0K#A:04002 | -1.485933 | 6.40488E-05 | 7.36585E-05 | -4.608549 | 1520.5 | 22288 | 20240.75 | 0 |

Fig. 3 (continued)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| clone rp5-847l8 on chromosome 1p34.1-36.11. contains ests gsss and stss. part of novel cub sushi ser repeat domain containing p | | AL355178 | mwghuman3 OK#B:9614 | -1.466888 | 8.43097E-06 | 3.15409E-05 | -4.397922 | 1529 | 4847.5 | 4650.25 | |
| cytochrome b5 reductase 3 (CYB5R3), transcript variant M, mRNA | NP_000389.1 | NM_000398.4 | mwghuman3 OK#A:01423 | -1.497796 | 0.0001216 06 | 9.05266E-05 | -5.28459 | 1531.5 | 9574.5 | 6353.5 | 9 |
| clone flb5834 pro1477 predicted protein of hq1477 | | AF130059 | mwghuman3 OK#E:1074 | -1.699661 | 1.17568E-05 | 3.32944E-05 | -4.802552 | 1535 | 5685 | 3946.75 | 10 |
| zinc finger, DHHC-type containing 2 (ZDHHC2), mRNA | NP_057437.1 | NM_016353.2 | mwghuman3 OK#A:03494 | -1.588633 | 8.03858E-06 | 0.000106 508 | -4.741236 | 1536 | 13684.5 | 10087.5 | 0 |
| cone-rod homeobox (CRX), mRNA | NP_000545.1 | NM_000554.2 | mwghuman3 OK#A:09219 | -3.022299 | 2.51326E-05 | 9.24336E-06 | -5.849282 | 1548 | 16588.5 | 7500.5 | 0 |

Fig. 3 (continued)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| chromosome 14 open reading frame 154 (C14orf154), transcript variant 1, mRNA | NP_115609.2 | NM_032233.2 | mwghuman3 0K#B:2655 | -1.704809 | 8.00302E-05 | 0.000166 293 | -4.427372 | 1561.5 | 16629 | 15080.75 | 5 |
| hypothetical protein xp_098665 loc155085 | | XM_098665 | mwghuman3 0K#B:6056 | -1.672814 | 4.27782E-05 | 0.000142 749 | -4.312941 | 1568.5 | 8795 | 8847.25 | |
| clone hq0117 pro0117 | | AF090895 | mwghuman3 0K#B:0914 | -1.888405 | 1.18377E-05 | 9.05268E-05 | -4.735768 | 1570.5 | 20158 | 14933.5 | 4 |
| prostate and breast cancer overexpressed 1 (PBOV1), mRNA | NP_087648.1 | NM_021635.1 | mwghuman3 0K#A:05114 | -1.610345 | 5.40979E-06 | 8.1662E-05 | -4.437567 | 1571.5 | 22494.5 | 19845.75 | 0 |
| esterase D/formylglutath ione hydrolase (ESD), mRNA | NP_001975.1 | NM_001984.1 | mwghuman3 0K#C:2841 | -1.535083 | 6.75303E-06 | 4.84259E-05 | -4.777065 | 1574 | 8049 | 4838.75 | 6 |
| ATG4 autophagy related 4 homolog B (S. cerevisiae) (ATG4B), transcript variant 1, mRNA | NP_037457.3 | NM_013325.4 | mwghuman3 0K#B:2748 | -1.348856 | 8.59727E-06 | 1.6224E-05 | -4.71932 | 1575 | 15166 | 16712.25 | 13 |

Fig. 3 (continued)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| NADPH oxidase 1 (NOX1), transcript variant NOH-1Lv, mRNA | NP_038249.1 | NM_139955.1 | mwghuman3 OK#B:1370 | -1.903809 | 5.04367E-06 | 2.65189E-05 | -3.799677 | 1585.5 | 18807.5 | 17371.5 | 0 |
| ensembl genscan prediction | | AL445675.9.1 .171885.3 | mwghuman3 OK#C:8741 | -1.774793 | 2.60881E-05 | 0.000182916 | -4.133137 | 1598 | 22483.5 | 18071.5 | |
| putative nuclear protein ORF1-FL49 (ORF1-FL49), mRNA | NP_115788.1 | NM_032412.2 | mwghuman3 OK#B:7958 | -1.499659 | 8.10749E-05 | 3.32944E-05 | -4.457256 | 1810.5 | 8598 | 4986 | 8 |
| THUMP domain containing 1 (THUMPD1), mRNA | NP_060206.2 | NM_017736.3 | mwghuman3 OK#B:2088 | -1.313257 | 4.11592E-07 | 6.53282E-08 | -5.325518 | 1651.5 | 14877 | 15313.5 | 0 |
| glutaminyl-peptide cyclotransferase (glutaminyl cyclase) (QPCT), mRNA | NP_036545.1 | NM_012413.3 | mwghuman3 OK#A:09422 | -1.769671 | 4.89509E-07 | 0.000122803 | -3.882851 | 1651.5 | 11960 | 8357.75 | 2 |
| PHD finger protein 23 (PHF23), mRNA | NP_077273.1 | NM_024297.1 | mwghuman3 OK#A:02678 | -1.398461 | 1.43961E-05 | 0.000109884 | -4.356774 | 1657.5 | 10656.5 | 9355.75 | 0 |

Fig. 3 (continued)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| nasopharyngeal carcinoma associated gene protein-8 (NAG8), mRNA | NP_055226.1 | NM_014411.2 | mwghuman3 0K#B:1462 | -1.380055 | 2.38325E-05 | 5.10584E-05 | -4.601658 | 1660 | 15731.5 | 12161 | 0 |
| ensembl genscan prediction | | AC013487.5.1 02379.117540.1 | mwghuman3 0K#C:3348 | -1.465832 | 0.0001448 57 | 2.37433E-06 | -6.225756 | 1682 | 14711 | 9423 | |
| ensembl genscan prediction | | AC079757.5.5 4037.628672.1 | mwghuman3 0K#C:3844 | -1.486502 | 2.89825E-05 | 4.12788E-05 | -4.765229 | 1684.5 | 25678.5 | 23576.5 | |
| hypothetical protein FLJ22313 (FLJ22313), mRNA | NP_071768.2 | NM_022373.3 | mwghuman3 0K#B:3974 | -1.47429 | 0.0001047 25 | 5.67358E-05 | -4.784258 | 1688.5 | 8360.5 | 9165.25 | 2 |
| holocytochrome c synthase (cytochrome c heme-lyase) (HCCS), mRNA | NP_005324.2 | NM_005333.2 | mwghuman3 0K#A:04510 | -2.084412 | 0.0003328 32 | 0.000211 888 | -5.978649 | 1692.5 | 10130.5 | 5488.25 | 4 |
| dual specificity phosphatase 5 (DUSP5), mRNA | NP_004410.3 | NM_004419.3 | mwghuman3 0K#A:04028 | -1.866767 | 5.52516E-05 | 2.27276E-05 | -5.708882 | 1694.5 | 16243.5 | 8885 | 2 |
| hypothetical protein FLJ20245 (FLJ20245), mRNA | NP_060193.1 | NM_017723.1 | mwghuman3 0K#B:2083 | -1.525801 | 6.09068E-05 | 0.000116 76 | -4.325617 | 1697 | 16122 | 13101 | 3 |

Fig. 3 (continued)

| Gene name/ symbol | protein accession | mRNA ref seq accession | MWG Probe name | median fold change | t-test | Wilcoxon test | SAM | rank score | tumour tissue median Intensity rank | non-malignant tissue median Intensity rank | blood |
|---|---|---|---|---|---|---|---|---|---|---|---|
| protein kinase, AMP-activated, gamma 2 non-catalytic subunit (PRKAG2), mRNA | NP_057287.2 | NM_018203.2 | mwghuman3 0K#A:00771 | -1.408092 | 1.41299E-05 | 8.59969E-05 | -4.435082 | 1697.5 | 16315.5 | 13437.25 | 5 |
| clone rp11-314a4 on chromosome 20. contains part of the eya2 eyes absent drosophila homolog 2 ests an sts and gsss_starts l | | AL359434 | mwghuman3 0K#B:9838 | -1.591958 | 1.67257E-05 | 6.56055E-05 | -4.203762 | 1702 | 25348.5 | 23840.75 | |
| hypothetical protein pro1598 pro1598 | | NM_018503 | mwghuman3 0K#B:0983 | -1.446989 | 3.89533E-06 | 1.30096E-05 | -5.339446 | 1716.5 | 24112.5 | 22818.75 | |
| NIMA (never in mitosis gene a)- related kinase 9 (NEK9), mRNA | NP_149107.3 | NM_033116.3 | mwghuman3 0K#C:0238 | -1.359292 | 3.822E-05 | 4.35419E-05 | -4.78725 | 1722.5 | 10134.5 | 7455.5 | 5 |
| glycine receptor, alpha 3 (GLRA3), mRNA | NP_006520.1 | NM_006529.1 | mwghuman3 0K#A:03690 | -1.412224 | 0.00010376 3 | 8.1682E-05 | -4.59741 | 1726 | 9472.5 | 8083.25 | 2 |

Fig. 3 (continued)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| ensembl genscan prediction | | AC004408.1.1.113252.2 | mwghuman3 OK#C:9512 | -1.54073 | 2.55537E-06 | 1.54035E-05 | -3.618774 | 1727 | 2977 | 2622.75 | |
| ensembl genscan prediction | | AP001655.2.148977.153525.1 | mwghuman3 OK#C:7868 | -1.286997 | 2.84478E-05 | 1.98829E-05 | -4.601991 | 1746 | 28566 | 28245.5 | |
| HERV-H LTR-associating 3 (HHLA3), transcript variant 3, mRNA | NP_001031722.1 | NM_001036845.1 | mwghuman3 OK#B:1046 | -2.043346 | 8.67677E-05 | 9.52087E-05 | -3.941702 | 1759 | 13925.5 | 11798 | 0 |
| ensembl genscan prediction | | AL355497.14.1.215397.9 | mwghuman3 OK#C:7911 | -3.056765 | 1.10766E-06 | 3.82785E-07 | -6.916789 | 1760 | 5872.5 | 2481.25 | |
| fibronectin leucine rich transmembrane protein 3 (FLRT3), transcript variant 1, mRNA | NP_037413.1 | NM_013281.2 | mwghuman3 OK#A:05822 | -4.204569 | 1.4941E-08 | 9.99201E-07 | -6.042443 | 1770 | 18156 | 9231.25 | 0 |
| cyp3a5 allele cyp3a5*3 alternatively spliced | | AF355802 | mwghuman3 OK#B:1830 | -1.371576 | 7.33293E-06 | 1.91497E-05 | -4.382299 | 1784 | 26198.5 | 24518.25 | |

Fig. 3 (continued)

| Gene name/ symbol | protein accession | mRNA ref seq accession | MWG Probe name | median fold change | t-test | Wilcoxon test | SAM | rank score | tumour tissue median Intensity rank | non-malignant tissue median intensity rank | blood |
|---|---|---|---|---|---|---|---|---|---|---|---|
| microfibrillar-associated protein 3-like (MFAP3L), transcript variant 1, mRNA | NP_067679.5 | NM_021647.5 | mwghuman3 OK#B:0217 | -1.887417 | 0.0001373 75 | 1.98715E -06 | -4.959479 | 1785 | 22262 | 18475.25 | 3 |
| cell division cycle associated 7 (CDCA7), transcript variant 1, mRNA | NP_114148.2 | NM_031942.3 | mwghuman3 OK#B:4810 | -1.959598 | 9.26637E-05 | 0.000150 506 | -4.246093 | 1788 | 14828 | 12577.25 | 1 |
| WD repeat domain 61 (WDR61), mRNA | NP_078510.1 | NM_025234.1 | mwghuman3 OK#B:1624 | -1.531798 | 0.0001544 91 | 0.000105 506 | -4.38785 | 1801.5 | 9756.5 | 8041.75 | 3 |
| protein kinase, AMP-activated, beta 1 non-catalytic subunit (PRKAB1), mRNA | NP_008244.2 | NM_006253.4 | mwghuman3 OK#A:04935 | -1.514877 | 9.29449E-05 | 0.000105 508 | -4.4366 | 1805.5 | 16011.5 | 13954 | 3 |
| zinc finger, A20 domain containing 2 (ZA20D2), mRNA | NP_009998.1 | NM_006007.1 | mwghuman3 OK#A:10213 | -1.857823 | 2.79105E-06 | 2.67916E -05 | -4.781221 | 1808.5 | 6855.5 | 4583.25 | 13 |
| similar to pro2852 loc93374 | | XM_050978 | mwghuman3 OK#B:7206 | -1.359998 | 8.48914E-05 | 6.30077E -05 | -5.206744 | 1817 | 19163 | 16436 | |

Fig. 3 (continued)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| catalase (CAT), mRNA | NP_001743.1 | NM_001752.2 | mwghuman3 OK#C:3530 | -2.225675 | 8.1938E-07 | 6.92439E-06 | -4.777325 | 1820 | 7219.5 | 4208.75 | 31 |
| peptidylprolyl isomerase (cyclophilin)-like 2 (PPIL2), transcript variant 2, mRNA | NP_680480.1 | NM_148175.1 | mwghuman3 OK#B:8262 | -1.384263 | 4.77437E-07 | 4.59274E-06 | -5.398075 | 1834.5 | 3806 | 3514 | 5 |
| perlexin (PRX), transcript variant 2, mRNA | NP_870998.1 | NM_181882.1 | mwghuman3 OK#A:01781 | -1.399169 | 1.03356E-05 | 6.63845E-05 | -4.549994 | 1838 | 19643.5 | 17122.5 | 0 |
| breast carcinoma amplified sequence 3 (BCAS3), mRNA | NP_060148.2 | NM_017679.2 | mwghuman3 OK#A:01576 | -1.41274 | 2.55423E-07 | 3.64015E-06 | -4.03611 | 1839 | 15754.5 | 17860.25 | 2 |
| HtrA serine peptidase 2 HTRA2 | AAF66598.1 | AF141307.1 | mwghuman3 OK#B:11170 | -1.284282 | 2.27894E-05 | 1.83362E-05 | -4.071282 | 1850 | 22760.5 | 20044.75 | |
| ensembl genscan prediction | | AC012095.13. 12848.174419. 1 | mwghuman3 OK#C:7012 | -1.517696 | 0.0001343 14 | 0.000172 435 | -4.407333 | 1854 | 26139.5 | 25010.5 | |
| formin binding protein 4 (FNBP4), mRNA | NP_056123.1 | NM_015308.1 | mwghuman3 OK#B:8897 | -1.360042 | 0.0001194 22 | 2.15085E-05 | -5.532889 | 1855 | 17142 | 14814.25 | 11 |

Fig. 3 (continued)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| aldehyde dehydrogenase 1 family, member L1 (ALDH1L1), mRNA | NP_036322.2 | NM_012190.2 | mwghuman3 0K#A:07479 | -2.396851 | 2.32309E-05 | 0.000157 701 | -3.740555 | 1858.5 | 13469 | 8189.5 | 3 |
| ensembl genscan prediction | | AP001487.3.8 5282.114407.1 | mwghuman3 0K#C:8733 | -1.603991 | 4.09016E-06 | 5.97939E-05 | -4.353485 | 1870 | 3882 | 3994.75 | |
| ensembl genscan prediction | | AC015851.18.1.191583.4 | mwghuman3 0K#C:2191 | -1.392136 | 5.55423E-07 | 1.72268E-05 | -4.562358 | 1873.5 | 2463 | 1928.25 | |
| OTU domain containing 5 (OTUD5), mRNA | NP_060072.1 | NM_017602.2 | mwghuman3 0K#B:7999 | -1.721318 | 3.42749E-06 | 1.37851E-05 | -5.356883 | 1894.5 | 1453 | 1011 | 14 |
| ensembl genscan prediction | | AC026868.5.8 4589.93793.1 | mwghuman3 0K#C:5546 | -1.668723 | 3.74924E-06 | 2.40122E-05 | -5.209366 | 1899 | 3201 | 1676.5 | |
| chromosome 20 open reading frame 121 (C20orf121), mRNA | NP_077307.1 | NM_024331.2 | mwghuman3 0K#A:03031 | -1.520517 | 5.93503E-08 | 1.82138E-05 | -4.163788 | 1906 | 8788 | 6894 | 2 |
| pyruvate dehydrogenase kinase, isozyme 4 (PDK4), mRNA | NP_002603.1 | NM_002612.2 | mwghuman3 0K#A:07564 | -1.735687 | 1.72294E-05 | 1.22937E-05 | -5.445156 | 1911.5 | 18087 | 13997.25 | 1 |

Fig. 3 (continued)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| KIAA1049 protein (KIAA1049), mRNA | NP_055787.1 | NM_014972.1 | mwghuman3 0K#B:2555 | -1.400381 | 1.30483E-05 | 7.36685E-05 | -4.350759 | 1913.5 | 10872 | 8868.5 | 12 |
| DnaJ (Hsp40) homolog, subfamily B, member 6 (DNAJB6), transcript variant 1, mRNA | NP_490647.1 | NM_058246.3 | mwghuman3 0K#A:04884 | -1.455602 | 9.60314E-05 | 0.000150 | -4.286084 | 1917 | 3609 | 2895.5 | 14 |
| lectin, galactoside-binding, soluble, 3 (galectin 3) (LGALS3), mRNA | NP_002287.1 | NM_002306.1 | mwghuman3 0K#A:10308 | -1.97733 | 6.69527E-06 | 2.55121E-05 | -4.890215 | 1923 | 2753 | 1803.5 | 6 |
| PTPRF interacting protein, binding protein 2 (liprin beta 2) (PPFIBP2), mRNA | NP_003612.1 | NM_003621.1 | mwghuman3 0K#B:0552 | -1.881545 | 1.28489E-06 | 2.98753E-05 | -4.14602 | 1937.5 | 8372.5 | 4594.5 | 2 |
| polymerase (DNA directed), lambda (POLL), mRNA | NP_037406.1 | NM_013274.2 | mwghuman3 0K#B:1279 | -1.399567 | 3.5582E-05 | 2.98753E-05 | -4.793854 | 1938 | 15108.5 | 11461.25 | 8 |

Fig. 3 (continued)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| growth differentiation factor 15 (GDF15), mRNA | NP_004855.1 | NM_004864.1 | mwghuman3 OK#A:07217 | -2.483648 | 0.0002241 34 | 0.000257 25 | -4.296268 | 1944 | 6377 | 3127.5 | 2 |
| hypothetical protein xp_089809 loc159765 | | XM_089809 | mwghuman3 OK#B:6474 | -1.381507 | 9.90157E-07 | 2.40122E-05 | -4.083057 | 1949 | 11626.5 | 11522.5 | |
| leucine rich repeat and sterile alpha motif containing 1 (LRSAM1), transcript variant 1, mRNA | NP_612370.3 | NM_138361.3 | mwghuman3 OK#B:4416 | -2.034574 | 0.0001840 31 | 0.000233 537 | -4.13512 | 1959. 5 | 7671.5 | 4421.75 | 1 |
| trafficking protein particle complex 6A (TRAPPC6A), mRNA | NP_077013.1 | NM_024108.1 | mwghuman3 OK#A:02117 | -1.452954 | 2.44741E-06 | 2.53657E-05 | -3.509555 | 1985 | 1279 | 1294 | 8 |
| ensembl genscan prediction | | AL357146.10. 1.82494.1 | mwghuman3 OK#C:3608 | -1.287782 | 1.49736E-05 | 6.05474E-05 | -4.826659 | 1989 | 28444.5 | 28083.25 | |
| hypothetical protein MGC14327 (MGC14327), mRNA | NP_444273.1 | NM_053045.1 | mwghuman3 OK#B:4427 | -1.504495 | 0.0001502 58 | 0.000174 117 | -4.521635 | 1992 | 16805 | 15440.5 | 4 |

Fig. 3 (continued)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| similar to kinesin family member 5b clone mgc:15265 image:4297793 | | BC009353 | mwghuman3 0K#B:4438 | -1.51682 | 0.0001882 14 | 0.000192 131 | -4.531075 | 1982 | 23071.5 | 21809.75 | |
| potassium channel tetramerisation domain containing 3 (KCTD3), mRNA | NP_057205.2 | NM_016121.3 | mwghuman3 0K#A:04386 | -1.358006 | 1.34593E-05 | 5.38262E-05 | -4.810824 | 1994.5 | 17479.5 | 13203.75 | 3 |
| ensembl genscan prediction | | AC018425.3.1 53134.186975 .1 | mwghuman3 0K#C:3925 | -1.466534 | 0.0001495 25 | 0.000192 131 | -4.315259 | 1997 | 25336 | 25414.75 | |
| guanine nucleotide binding protein (G protein), alpha inhibiting activity polypeptide 1 (GNAI1), mRNA | NP_002060.4 | NM_002069.4 | mwghuman3 0K#A:10201 | -1.631361 | 5.34666E-06 | 0.000433 377 | -3.885348 | 2003 | 16803.5 | 14082 | 1 |
| microtubule-associated protein 4 (MAP4), transcript variant 1, mRNA | NP_002366.2 | NM_002375.3 | mwghuman3 0K#B:4355 | -1.468752 | 0.0001551 87 | 0.000257 25 | -4.423897 | 2004 | 10052 | 9080 | 11 |

Fig. 3 (continued)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| nucleolar protein family 6 (RNA-associated) (NOL6), transcript variant alpha, mRNA | NP_075068.2 | NM_022917.4 | mwghuman3 OK#A:07182 | -1.30257 | 1.12604E-06 | 3.70831E-05 | -4.767639 | 2009 | 10513 | 8821 | 7 |
| cerebral endothelial cell adhesion molecule 1 (CEECAM1), mRNA | NP_057258.2 | NM_016174.3 | mwghuman3 OK#A:10231 | -1.516413 | 4.80846E-05 | 0.000109198 | -3.867581 | 2014 | 16662.5 | 13757.75 | 0 |
| ubiquinol-cytochrome c reductase, complex III subunit VII, 9.5kDa (UQCRQ), nuclear gene encoding mitochondrial protein, mRNA | NP_055217.2 | NM_014402.3 | mwghuman3 OK#B:8060 | -1.71221 | 4.79881E-05 | 4.35419E-05 | -5.049158 | 2014 | 4199.5 | 2985.25 | 14 |
| hypothetical protein xp_092745 loc164337 | | XM_092745 | mwghuman3 OK#B:3255 | -1.386871 | 3.26973E-05 | 0.000165718 | -4.513374 | 2041 | 19510 | 15741.25 | |

Fig. 3 (continued)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| hypothetical protein FLJ22995 (FLJ22995), mRNA | NP_071384.1 | NM_022101.2 | mwghuman3 OK#A:09776 | -1.903469 | 7.16955E-05 | 0.000475 592 | -4.078844 | 2041.5 | 2596 | 2337 | 0 |
| chromosome 9 open reading frame 102 (C9orf102), transcript variant 1, mRNA | NP_064592.1 | NM_020207.2 | mwghuman3 OK#B:8956 | -1.369819 | 3.05523E-05 | 0.000105 506 | -4.676244 | 2049 | 16457.5 | 13970 | 0 |
| sphingosine-1-phosphate phosphatase 1 (SGPP1), mRNA | NP_110418.1 | NM_030791.2 | mwghuman3 OK#B:1809 | -1.477332 | 4.90035E-05 | 0.000142 749 | -4.328137 | 2062.5 | 20094 | 17541.5 | 1 |
| pleckstrin and Sec7 domain containing 3 (PSD3), transcript variant 1, mRNA | NP_056125.2 | NM_015310.2 | mwghuman3 OK#B:9515 | -1.395381 | 2.70551E-05 | 0.000142 896 | -3.953529 | 2072 | 14023 | 13223.25 | 1 |
| hypothetical protein LOC283874 (LOC283874), mRNA | NP_001012749.1 | NM_001012731.1 | mwghuman3 OK#B:2101 | -1.376341 | 1.45793E-05 | 2.67916E-05 | -5.079903 | 2080.5 | 23511.5 | 23000 | 1 |

Fig. 3 (continued)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| zinc finger, FYVE domain containing 21 (ZFYVE21), mRNA | NP_076976.1 | NM_024071.2 | mwghuman3 OK#A:05842 | -1.579562 | 0.0001142 53 | 0.000342 648 | -4.238027 | 2094 | 2984.5 | 2740.25 | 0 |
| forkhead box E1 (thyroid transcription factor 2) (FOXE1), mRNA | NP_004464.2 | NM_004473.3 | mwghuman3 OK#A:07899 | -1.878652 | 1.3104E-05 | 0.000192 131 | -3.837954 | 2107 | 7269 | 5293.75 | 0 |
| ensembl genscan prediction | | AL158168.17. 82811.114103 .1 | mwghuman3 OK#C:5892 | -1.54059 | 5.72345E-05 | 8.88591E-05 | -4.136599 | 2114 | 28578 | 27753.75 | |
| similar to per-hexamer repeat protein 5 loc149135 | | XM_089208 | mwghuman3 OK#B:9694 | -1.363387 | 0.0001055 64 | 3.77872E-05 | -3.9371 | 2131 | 27002.5 | 27249.5 | |
| zinc finger, matrin type 1 (ZMAT1), transcript variant 3, mRNA | NP_115817.1 | NM_032441.1 | mwghuman3 OK#C:0108 | -1.423698 | 0.0001562 67 | 0.000211 888 | -4.538065 | 2134.5 | 20339.5 | 17180.25 | 2 |
| endoplasmic reticulum to nucleus signalling 2 (ERN2), mRNA | NP_150286.2 | NM_033266.2 | mwghuman3 OK#B:9444 | -1.735187 | 1.98165E-05 | 2.70994E-05 | -4.509363 | 2135 | 24789 | 18903 | 0 |

Fig. 3 (continued)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| ring finger protein 38 (RNF38), transcript variant 1, mRNA | NP_073618.3 | NM_022781.3 | mwghuman3 0K#B:5588 | -1.302865 | 2.50283E-06 | 2.15085E-05 | -4.986001 | 2138 | 24546.5 | 22148.75 | 1 |
| Myc-induced mitochondria protein (mimitin), mRNA | NP_777549.1 | NM_174889.2 | mwghuman3 0K#B:3716 | -1.474873 | 8.439E-05 | 0.000359234 | -4.207401 | 2151.5 | 9215 | 7030.25 | 1 |
| TGF beta-inducible nuclear protein 1 (TINP1), mRNA | NP_055701.1 | NM_014886.2 | mwghuman3 0K#A:06520 | -1.655993 | 0.0003187 59 | 0.000571 767 | -4.798546 | 2153 | 7530 | 5545.5 | 8 |
| similar to developmental pluripotency associated 5; embryonal stem cell specific gene 1 (LOC341912), mRNA | XP_292301.3 | XM_292301.3 | mwghuman3 0K#B:8134 | -1.639786 | 7.64251E-07 | 4.32856E-06 | -5.437632 | 2155 | 18581.5 | 12815.25 | 1 |
| dehydrogenase/reductase (SDR family) member 3 (DHRS3), mRNA | NP_004744.2 | NM_004753.4 | mwghuman3 0K#B:0738 | -1.439285 | 4.39582E-05 | 0.000222 464 | -3.974187 | 2160.5 | 4626 | 3570 | 3 |

Fig. 3 (continued)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
| --- | --- | --- | --- | --- | --- | --- | --- | --- | --- | --- | --- |
| flavin containing monooxygenase 4 (FMO4), mRNA | NP_002013.1 | NM_002022.1 | mwghuman3 0K#B:2927 | -1.804252 | 0.0001959 67 | 0.000222 464 | -4.159771 | 2173.5 | 21428 | 18241 | 1 |
| ensembl genscan prediction | | AC022526.4.9 087.13827.1 | mwghuman3 0K#C:9081 | -1.518222 | 0.0001284 09 | 0.000174 117 | -4.437239 | 2174 | 25713.5 | 23316 | |
| serologically defined colon cancer antigen 8 (SDCCAG8), mRNA | NP_006633.1 | NM_006642.1 | mwghuman3 0K#B:4992 | -1.359218 | 5.81032E-06 | 1.22937E-05 | -4.628131 | 2177.5 | 18848 | 16568 | 4 |
| CDC14 cell division cycle 14 homolog B (S. cerevisiae) (CDC14B), transcript variant 2, mRNA | NP_201588.1 | NM_033331.1 | mwghuman3 0K#B:0753 | -1.438488 | 0.0001500 76 | 0.000245 124 | -4.702655 | 2178.5 | 23322 | 22971 | 2 |
| myeloid/lymph oid or mixed-lineage leukemia (trithorax homolog, Drosophila); translocated to, 3 (MLLT3), mRNA | NP_004520.1 | NM_004529.1 | mwghuman3 0K#A:00725 | -1.503791 | 3.87447E-05 | 0.000311 603 | -4.282874 | 2186 | 20164.5 | 17452 | 4 |

Fig. 3 (continued)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| cytochrome P450, family 27, subfamily A, polypeptide 1 (CYP27A1), nuclear gene encoding mitochondrial protein, mRNA | NP_000775.1 | NM_000784.2 | mwghuman3 0K#A:07422 | -1.399908 | 4.05019E-05 | 3.91276E-05 | -4.065883 | 2197 | 20714 | 13781.5 | 10 |
| pre-tnk cell associated protein 1f6 3' end | | L17326 | mwghuman3 0K#B:9025 | -1.643879 | 5.92884E-06 | 3.84322E-06 | -5.055927 | 2201 | 6449.5 | 4787.5 | |
| hepcidin antimicrobial peptide (HAMP), mRNA | NP_066998.1 | NM_021175.2 | mwghuman3 0K#A:08397 | -1.279742 | 2.53831E-05 | 1.72266E-05 | -4.893297 | 2205.5 | 3722.5 | 3385.25 | 0 |
| ensembl genscan prediction | | AC078819.13. 1.41283.1 | mwghuman3 0K#C:7792 | -1.349603 | 2.94705E-06 | 7.88194E-05 | -4.262185 | 2213 | 21361.5 | 17800.75 | |
| hypothetical protein BC009862 (LOC901113), mRNA | XP_291077.3 | XM_291077.3 | mwghuman3 0K#B:3668 | -1.769275 | 0.00034056 9 | 0.000454 027 | -4.413577 | 2221.5 | 6281.5 | 5176 | 0 |
| elongation factor, RNA polymerase II, 2 (ELL2), mRNA | NP_036213.1 | NM_012081.3 | mwghuman3 0K#A:00356 | -1.499648 | 5.40285E-05 | 0.000157 701 | -4.384409 | 2223.5 | 14138 | 11702.5 | 4 |

Fig. 3 (continued)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| FGFR1 oncogene partner (FGFR1OP), transcript variant 1, mRNA | NP_008976.1 | NM_007045.2 | mwghuman3 0K#53:4675 | -1.513357 | 9.11409E-05 | 0.000233 537 | -4.085108 | 2228.5 | 19894 | 19145.25 | 0 |
| ensembl genscan prediction | | AC025953.2.1 16948.127472 .1 | mwghuman3 0K#C:6647 | -2.043219 | 0.0001551 45 | 0.000283 207 | -3.955032 | 2231 | 21041 | 17429.5 | |
| EH domain binding protein 1 (EHBP1), mRNA | NP_056067.1 | NM_015252.2 | mwghuman3 0K#B:0385 | -1.35833 | 2.50342E-08 | 6.99321E-05 | -4.628579 | 2249.5 | 13151.5 | 12131 | 5 |
| propionyl Coenzyme A carboxylase, alpha polypeptide (PCCA), mRNA | NP_000273.2 | NM_000282.2 | mwghuman3 0K#B:3551 | -1.505038 | 8.411E-05 | 0.000110 999 | -4.042034 | 2251 | 16323 | 13459 | 5 |
| ensembl genscan prediction | | AL138499.4.1 .185713.1 | mwghuman3 0K#C:4137 | -1.655664 | 1.65577E-05 | 8.59968E-05 | -3.700791 | 2252.5 | 6728 | 6542.5 | |
| ensembl genscan prediction | | AC025937.3.2 8407.38498.1 | mwghuman3 0K#C:9420 | -5.821331 | 1.28566E-11 | 3.14688E-07 | -6.568115 | 2255.5 | 3524 | 1068.5 | |

Fig. 3 (continued)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| myocilin, trabecular meshwork inducible glucocorticoid response (MYOC), mRNA | NP_000252.1 | NM_000261.1 | mwghuman3 0K#A:09842 | -1.384785 | 4.81814E-05 | 2.61402E-05 | -4.638227 | 2263 | 23815.5 | 22357.25 | 0 |
| hspc074 | | AF161337 | mwghuman3 0K#B:1281 | -1.61806 | 1.54865E-06 | 1.54035E-05 | -4.428706 | 2284.5 | 1792 | 1727 | 3 |
| epoxide hydrolase 2, cytoplasmic (EPHX2), mRNA | NP_001970.2 | NM_001979.4 | mwghuman3 0K#A:08300 | -1.416388 | 5.8666E-05 | 5.81228E-05 | -4.695716 | 2267.5 | 19752.5 | 16857 | 3 |
| centromere protein C 1 (CENPC1), mRNA | NP_001803.2 | NM_001812.2 | mwghuman3 0K#A:10535 | -1.578112 | 0.0001833 56 | 0.000192 131 | -4.258306 | 2275 | 19346.5 | 14107.25 | 4 |
| polyA polymerase beta (testis specific) (PAPOLB), mRNA | NP_084529.4 | NM_020144.4 | mwghuman3 0K#A:00034 | -1.533242 | 0.0001793 94 | 0.000311 803 | -4.111846 | 2284 | 24777 | 23772.75 | 1 |
| oligonucleotide /oligosaccharid e-binding fold containing 1 (OBFC1), mRNA | NP_079204.1 | NM_024928.3 | mwghuman3 0K#A:07368 | -1.597262 | 0.0001519 06 | 0.000150 05 | -4.338099 | 2292 | 15940.5 | 11655 | 4 |

Fig. 3 (continued)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| tripartite motif-containing 10 (TRIM10), transcript variant 1, mRNA | NP_006769.1 | NM_006778.2 | mwghuman3 0K#A:10515 | -1.7509612 | 5.52205E-05 | 0.000135 784 | -4.621742 | 2296.5 | 4089.5 | 1585.5 | 0 |
| Rap2-binding protein 9 (RPIB9), mRNA | NP_612147.1 | NM_138280.1 | mwghuman3 0K#B:7696 | -1.451227 | 1.03873E-06 | 1.37651E-05 | -5.068475 | 2297 | 24138.5 | 22036.5 | 1 |
| fksg17 | | NM_032031 | mwghuman3 0K#B:1656 | -1.576144 | 0.0001418 34 | 0.000233 537 | -4.037861 | 2320.5 | 2050 | 1701.75 | 1 |
| G protein-coupled receptor 83 (GPR83), mRNA | NP_057624.2 | NM_016540.2 | mwghuman3 0K#A:05359 | -1.472466 | 6.54909E-05 | 0.000182 816 | -3.811779 | 2322.5 | 18971.5 | 15879.25 | 0 |
| ensembl genscan prediction | | AC078987.9.1 35718.144151 .1 | mwghuman3 0K#C:4632 | -1.300374 | 2.50018E-05 | 1.72266E-05 | -4.918105 | 2322.5 | 25018.5 | 21332.5 | |
| LIM homeobox 9 (LHX9), transcript variant 1, mRNA | NP_084589.2 | NM_020204.2 | mwghuman3 0K#B:8634 | -1.374971 | 4.8851E-06 | 9.24336E-06 | -5.312469 | 2333.5 | 16158 | 13872.25 | 0 |
| pellino homolog 1 (Drosophila) (PELI1), mRNA | NP_065702.2 | NM_020851.2 | mwghuman3 0K#A:10770 | -1.492084 | 8.8328E-06 | 8.23838E-06 | -5.23835 | 2338 | 22421.5 | 17524.5 | 7 |

Fig. 3 (continued)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| hypothetical LOC401500 (LOC401500), mRNA | XP_379529.1 | XM_379529.1 | mwghuman3 OK#B:5223 | -1.325858 | 2.27785E-05 | 4.12788E-05 | -4.402696 | 2338.5 | 28315 | 25320.25 | 0 |
| TSC22 domain family, member 3 (TSC22D3), transcript variant 2, mRNA | NP_004080.2 | NM_004089.3 | mwghuman3 OK#B:3462 | -1.491298 | 5.41371E-05 | 1.72268E-05 | -5.010311 | 2350.5 | 18693.5 | 13200.5 | 43 |
| G protein-coupled receptor 61 (GPR51), mRNA | NP_005449.5 | NM_005458.5 | mwghuman3 OK#A:04815 | -1.389185 | 0.0001017 08 | 2.98753E-05 | -4.845166 | 2361 | 3420 | 2489.25 | 0 |
| chromosome 10 open reading frame 61 (C10orf61), transcript variant 2, mRNA | NP_056446.1 | NM_016631.2 | mwghuman3 OK#B:3105 | -1.555923 | 0.0001770 95 | 0.000297 088 | -4.510054 | 2368.5 | 10134 | 8091.5 | 3 |
| jumonji domain containing 2C (JMJD2C), mRNA | NP_055876.1 | NM_015061.1 | mwghuman3 OK#B:8433 | -1.317474 | 6.41124E-05 | 0.000142 749 | -4.870495 | 2368.5 | 24516.5 | 22272.75 | 11 |
| zinc finger protein 547 (ZNF547), mRNA | NP_775902.2 | NM_173631.2 | mwghuman3 OK#B:6716 | -1.63256 | 0.0002511 74 | 0.000257 25 | -3.984452 | 2370 | 19484 | 19537 | 2 |

Fig. 3 (continued)

| Gene name/ symbol | protein accession | mRNA ref seq accession | MWG Probe name | median fold change | t-test | Wilcoxon test | SAM | rank score | turnour tissue median intensity rank | non-malignant tissue median intensity rank | blood |
|---|---|---|---|---|---|---|---|---|---|---|---|
| hypothetical protein FLJ20032 (FLJ20032), mRNA | NP_060098.2 | NM_017628.2 | mwghuman3 OK#B:2068 | -1.74414 | 8.61052E-05 | 0.000105 506 | -4.166213 | 2374 | 15233.5 | 9767.75 | 16 |
| ensembl genscan prediction | | AC064877.3.1 21131.166993 .1 | mwghuman3 OK#C:7466 | -1.319284 | 4.28953E-05 | 2.03519E-05 | -4.602131 | 2374 | 27348 | 26740.25 | |
| ensembl genscan prediction | | AC027755.2.8 1287.97080.1 | mwghuman3 OK#C:3411 | -1.439071 | 0.00001259 01 | 0.000331 474 | -4.145868 | 2378.5 | 14385.5 | 10781.5 | |
| KIAA0890 (KIAA0890), mRNA | NP_055894.1 | NM_015179.2 | mwghuman3 OK#B:7202 | -1.642414 | 0.0001739 36 | 0.000433 377 | -4.08872 | 2380 | 14459 | 11844.25 | 10 |
| SH3 domain binding glutamic acid-rich protein like 2 (SH3BGRL2), mRNA | NP_113857.1 | NM_031488.1 | mwghuman3 OK#B:1794 | -1.995457 | 0.0002796 76 | 0.000376 568 | -4.033794 | 2381 | 8893.5 | 6985.75 | 3 |
| cdna: fj21384 fis clone col03536 unnamed protein product | | AK025047 | mwghuman3 OK#B:2580 | -2.258109 | 0.0004473 76 | 0.000359 234 | -4.071961 | 2387.5 | 17288 | 11926.75 | 0 |
| hypothetical protein xp_039231 loc91565 | | XM_039231 | mwghuman3 OK#B:8431 | -1.337232 | 2.70835E-05 | 0.000174 117 | -4.141157 | 2398 | 24099.5 | 20885 | |

Fig. 3 (continued)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| GPI anchored molecule like protein (GML), mRNA | NP_002057.1 | NM_002066.1 | mwghuman3 0K#A:02108 | -1.438045 | 0.0000724 93 | 0.000129 14 | -4.162956 | 2405 | 16818 | 14285.75 | 0 |
| small nuclear RNA activating complex, polypeptide 5, 19kDa (SNAPC5), mRNA | NP_006040.1 | NM_006049.1 | mwghuman3 0K#B:09945 | -1.323754 | 1.74702E-05 | 0.000184 787 | -4.005319 | 2444 | 17556.5 | 17969.25 | 6 |
| ensembl genscan prediction | | AC027689.10. 1.180573.5 | mwghuman3 0K#C:19758 | -1.844263 | 0.0002550 65 | 2.98763E -05 | -3.674603 | 2451 | 16829.5 | 10684.25 | |
| mitochondrial tumor suppressor 1 (MTUS1), nuclear gene encoding mitochondrial protein, transcript variant 1, mRNA | NP_0010019 24.1 | NM_0010019 24.1 | mwghuman3 0K#B:7775 | -1.715161 | 0.0003036 63 | 0.000269 936 | -4.435392 | 2461. 5 | 17489 | 15873 | 0 |
| ensembl genscan prediction | | AL049829.4.1 .196292.3 | mwghuman3 0K#C:4548 | -1.402914 | 1.70081E-06 | 2.49927E -06 | -5.01844 | 2471 | 28131 | 26784 | |
| ensembl genscan prediction | | AC084842.1.7 903.10639.1 | mwghuman3 0K#C:7838 | -1.400793 | 0.0008120 94 | 7.36585E -05 | -5.107784 | 2475. 5 | 14235.5 | 11061.25 | |

Fig. 3 (continued)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| SAFB-like, transcription modulator (SLTM), transcript variant 1, mRNA | NP_079031.2 | NM_024755.2 | mwghuman3 OK#B:2154 | -1.308539 | 2.00445E-05 | 0.000122 803 | -4.680439 | 2477.5 | 12490 | 12280 | 12 |
| guanine nucleotide binding protein (G protein), alpha activating activity polypeptide; olfactory type (GNAL), transcript variant 2, mRNA | NP_002062.1 | NM_002071.1 | mwghuman3 OK#A:06286 | -1.836112 | 0.0003002 6 | 0.000498 109 | -4.10637 | 2478 | 19858 | 16880.75 | 0 |
| similar to cg14182 product loc146175 | | XM_085352 | mwghuman3 OK#B:7365 | -1.748066 | 0.0001949 23 | 0.000433 377 | -3.812815 | 2487 | 14791.5 | 9814.5 | |
| PH domain and leucine rich repeat protein phosphatase (PHLPP), mRNA | NP_919431.1 | NM_194449.1 | mwghuman3 OK#B:2242 | -2.043619 | 0.0003079 45 | 0.000498 109 | -4.006924 | 2500 | 15125 | 10009.75 | 7 |

Fig. 3 (continued)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| autism susceptibility candidate 2 (AUTS2), mRNA | NP_055385.1 | NM_015570.1 | mwghuman3 OK#B:0110 | -1.807633 | 0.0003692 99 | 0.0003982 814 | -4.213775 | 2503 | 18404 | 14412.75 | 8 |
| hypothetical protein xp_097338 loc147809 | | XM_097338 | mwghuman3 OK#B:5652 | -1.428873 | 1.32234E-08 | 2.87916E-05 | -4.387947 | 2513 | 4388 | 2981.75 | |
| leucine-rich repeat-containing G protein-coupled receptor 4 (LGR4), mRNA | NP_060960.1 | NM_018490.1 | mwghuman3 OK#A:06106 | -1.519205 | 7.81416E-05 | 0.000122 803 | -3.810559 | 2514.5 | 21417.5 | 19884 | 2 |
| ensembl prediction | | ENSG000001 13407 | mwghuman3 OK#C:2560 | -1.740805 | 1.93346E-05 | 9.52811E-05 | -4.388894 | 2525 | 8797.5 | 6359.5 | |
| programmed cell death 1 (PDCD1), mRNA | NP_005009.1 | NM_005018.1 | mwghuman3 OK#B:9147 | -1.519488 | 1.50412E-08 | 3.41028E-08 | -5.713059 | 2537 | 8575 | 7118.5 | 0 |
| cadherin 20, type 2 (CDH20), mRNA | NP_114097.2 | NM_031891.2 | mwghuman3 OK#B:7584 | -1.393019 | 1.91884E-05 | 2.73302E-05 | -4.362445 | 2538 | 15588 | 12275.75 | 0 |

Fig. 3 (continued)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| glycine dehydrogenase (decarboxylating; glycine decarboxylase, glycine cleavage system protein P) (GLDC), mRNA | NP_000161.1 | NM_000170.1 | mwghuman3 OK#B:89959 | -1.405054 | 9.33312E-05 | 0.000116 76 | -4.398207 | 2542.5 | 6039 | 4550.5 | 1 |
| protease, serine, 35 (PRSS35), mRNA | NP_899193.1 | NM_153362.1 | mwghuman3 OK#B:3364 | -1.451818 | 0.0002370 39 | 0.000257 25 | -4.319803 | 2545 | 16909 | 14109 | 0 |
| ensembl genscan prediction | | AC008134.3.1 .175132.1 | mwghuman3 OK#C:3643 | -1.601839 | 0.0003788 4 | 0.000286 633 | -4.042534 | 2545 | 27071.5 | 25825 | |
| ATP-binding cassette, sub-family A (ABC1), member 12 (ABCA12), transcript variant 1, mRNA | NP_775099.2 | NM_173076.2 | mwghuman3 OK#B:3505 | -1.653773 | 0.0002371 78 | 0.000475 592 | -3.927921 | 2561.5 | 19931 | 18593.5 | 0 |
| suppressor of hairy wing homolog 3 (Drosophila) (SUHW3), mRNA | NP_060136.1 | NM_017668.2 | mwghuman3 OK#B:2904 | -1.678106 | 0.0001663 59 | 0.000546 156 | -3.864728 | 2568 | 17527 | 15364.5 | 1 |

Fig. 3 (continued)

| Gene name/symbol | protein accession | mRNA ref seq accession | median fold change | rank score | tumour tissue median intensity rank | non-malignant tissue median intensity rank | blood EST number |
|---|---|---|---|---|---|---|---|
| hypothetical protein FLJ21511 (FLJ21511), mRNA | NP_079363.1 | NM_025087.1 | -2.060908 | 68 | 14455 | 9272.5 | 0 |
| paired box gene 8 (PAX8), transcript variant PAX8A, mRNA | NP_003457.1 | NM_003466.3 | -1.961898 | 82 | 19419 | 12899.5 | 0 |
| UPF3 regulator of nonsense transcripts homolog A (yeast) (UPF3A), transcript variant 1, mRNA | NP_075387.1 | NM_023011.2 | -3.84007 | 96.5 | 5663.5 | 1825 | 0 |
| leukotriene B4 12-hydroxydehydrogenase (LTB4DH), mRNA | NP_036344.1 | NM_012212.2 | -5.034613 | 122.5 | 11340.5 | 3138 | 0 |
| RAB11 family interacting protein 2 (class I) (RAB11FIP2), mRNA | NP_055719.1 | NM_014904.1 | -1.993629 | 156 | 19636.5 | 12951 | 0 |
| TSC22 domain family, member 1 (TSC22D1), transcript variant 2, mRNA | NP_006013.1 | NM_006022.2 | -2.133065 | 156.5 | 8415 | 6130 | 1 |
| sulfite oxidase (SUOX), nuclear gene encoding mitochondrial protein, transcript variant 1, mRNA | NP_000447.2 | NM_000456.2 | -1.622803 | 223 | 11312.5 | 8789.5 | 0 |
| tetratricopeptide repeat domain 21A (TTC21A), mRNA | NP_665698.1 | NM_145755.1 | -2.978809 | 225 | 8375.5 | 3870.5 | 1 |
| synaptotagmin-like 2 (SYTL2), transcript variant b, mRNA | NP_115755.2 | NM_032378.3 | -2.343357 | 342 | 19920 | 12053.5 | 0 |
| wingless-type MMTV integration site family, member 2B (WNT2B), transcript variant WNT-2B1, mRNA | NP_004176.2 | NM_004185.2 | -10.745275 | 501 | 10716 | 2016.25 | 0 |
| protocadherin gamma subfamily A, 12 (PCDHGA12), transcript variant 1, mRNA | NP_003726.1 | NM_003735.2 | -2.070447 | 511 | 2537 | 1931.5 | 0 |
| olfactory receptor, family 1, subfamily D, member 5 (OR1D5), mRNA | NP_055381.1 | NM_014566.1 | -1.840751 | 539.5 | 1844 | 1134 | 0 |
| G protein-coupled receptor 126 (GPR126), transcript variant b1, mRNA | NP_940971.1 | NM_198569.1 | -2.181735 | 549 | 15965.5 | 8040.75 | 0 |
| ubiquitin specific peptidase 9, Y-linked (fat facets-like, Drosophila) (USP9Y), mRNA | NP_004845.2 | NM_004654.3 | -1.584085 | 587 | 10035.5 | 7858.25 | 1 |

Fig. 4

| Gene name/symbol | protein accession | mRNA ref seq accession | median fold change | rank score | tumour tissue median intensity rank | non-malignant tissue median intensity rank | blood EST number |
|---|---|---|---|---|---|---|---|
| chromosome 11 open reading frame 1 (C11orf1), mRNA | NP_073598.1 | NM_022761.1 | -1.81726 | 673.5 | 12025.5 | 9585.25 | 0 |
| BCL2-associated athanogene (BAG1), mRNA | NP_004314.3 | NM_004323.3 | -2.525417 | 776 | 9031 | 4503.5 | 1 |
| family with sequence similarity 44, member B (FAM44B), mRNA | NP_812378.1 | NM_138369.1 | -1.357114 | 942.5 | 15308.5 | 13004.75 | 1 |
| fibroblast growth factor receptor 4 (FGFR4), transcript variant 2, mRNA | NP_075252.2 | NM_022963.2 | -2.638426 | 1087.5 | 17086 | 9762.5 | 0 |
| thyroid transcription factor 1 (TITF1), mRNA | NP_003308.1 | NM_003317.3 | -1.466987 | 1124.5 | 2139 | 1028.25 | 0 |
| VprBP protein (VprBP), mRNA | NP_055518.1 | NM_014703.1 | -1.720326 | 1178 | 17312.5 | 14031 | 0 |
| empty spiracles homolog 2 (Drosophila) (EMX2), mRNA | NP_004089.1 | NM_004098.2 | -1.745086 | 1199.5 | 19380 | 10749.25 | 0 |
| homeo box D8 (HOXD8), mRNA | NP_062458.1 | NM_019558.2 | -1.41555 | 1206 | 9672.5 | 7512.25 | 0 |
| zinc finger protein 626 (ZNF626), mRNA | NP_660340.1 | NM_145297.2 | -1.773183 | 1266 | 14808.5 | 10341 | 1 |
| ring finger protein 44 (RNF44), mRNA | NP_055716.1 | NM_014901.4 | -1.353366 | 1292 | 6288.5 | 4684.5 | 1 |
| pyrimidinergic receptor P2Y, G-protein coupled, 4 (P2RY4), mRNA | NP_002556.1 | NM_002565.3 | -1.732075 | 1309 | 18307 | 12139.5 | 0 |
| similar to hypothetical protein (LOC440804), mRNA | XP_038936.3 | XM_038936.3 | -4.049848 | 1332 | 3647 | 986.5 | 0 |
| chromosome 20 open reading frame 152 (C20orf152), mRNA | NP_543024.1 | NM_080834.1 | -1.948612 | 1349 | 10775 | 8852.5 | 0 |
| follistatin-like 4 (FSTL4), mRNA | NP_055597.1 | NM_015082.1 | -1.544042 | 1405.5 | 17051 | 12319 | 0 |
| chromosome 14 open reading frame 168 (C14orf168), mRNA | NP_113915.1 | NM_031427.1 | -1.512002 | 1414 | 15738 | 14705.75 | 1 |
| kallikrein 8 (neuropsin/ovasin) (KLK8), transcript variant 2, mRNA | NP_653088.1 | NM_144505.1 | -2.091505 | 1449.5 | 8391 | 6488 | 0 |
| leucine zipper, down-regulated in cancer 1-like (LDOC1L), mRNA | NP_115663.2 | NM_032287.2 | -1.501021 | 1454.5 | 16509.5 | 14157 | 0 |
| hypothetical protein MGC11242 (MGC11242), mRNA | NP_077296.1 | NM_024320.2 | -1.527839 | 1463.5 | 17565 | 13134.5 | 0 |
| KIAA1274 (KIAA1274), mRNA | NP_055246.1 | NM_014431.1 | -1.41942 | 1488.5 | 8059 | 5065 | 0 |
| hypothetical LOC401510 (LOC401510), mRNA | XP_376843.2 | XM_376843.2 | -1.402922 | 1504 | 13882.5 | 11233.25 | 0 |

Fig. 4 (continued)

| Gene name/symbol | protein accession | mRNA ref seq accession | median fold change | rank score | tumour tissue median Intensity rank | non-malignant tissue median intensity rank | blood EST number |
|---|---|---|---|---|---|---|---|
| plastin 1 (I isoform) (PLS1), mRNA | NP_002661.1 | NM_002670.1 | -1.626206 | 1509.5 | 20943 | 14040.5 | 1 |
| zinc finger, DHHC-type containing 2 (ZDHHC2), mRNA | NP_057437.1 | NM_016353.2 | -1.588633 | 1536 | 13684.5 | 10087.5 | 0 |
| cone-rod homeobox (CRX), mRNA | NP_000545.1 | NM_000554.2 | -3.022299 | 1548 | 16588.5 | 7500.5 | 0 |
| PHD finger protein 23 (PHF23), mRNA | NP_077273.1 | NM_024297.1 | -1.388461 | 1657.5 | 10666.5 | 9355.75 | 0 |
| nasopharyngeal carcinoma associated gene protein-8 (NAG8), mRNA | NP_055226.1 | NM_014411.2 | -1.388055 | 1660 | 15731.5 | 12161 | 0 |
| HERV-H LTR-associating 3 (HHLA3), transcript variant 3, mRNA | NP_001031722.1 | NM_001036645.1 | -2.043346 | 1759 | 13925.5 | 11798 | 0 |
| fibronectin leucine rich transmembrane protein 3 (FLRT3), transcript variant 1, mRNA | NP_037413.1 | NM_013281.2 | -4.204569 | 1770 | 18156 | 9231.25 | 0 |
| cell division cycle associated 7 (CDCA7), transcript variant 1, mRNA | NP_114148.2 | NM_031942.3 | -1.858598 | 1788 | 14826 | 12677.25 | 1 |
| pyruvate dehydrogenase kinase, isozyme 4 (PDK4), mRNA | NP_002603.1 | NM_002612.2 | -1.735687 | 1911.5 | 18067 | 13997.25 | 1 |
| leucine rich repeat and sterile alpha motif containing 1 (LRSAM1), transcript variant 1, mRNA | NP_612370.3 | NM_138361.3 | -2.034574 | 1959.5 | 7871.5 | 4421.75 | 1 |
| guanine nucleotide binding protein (G protein), alpha inhibiting activity polypeptide 1 (GNAI1), mRNA | NP_002060.4 | NM_002069.4 | -1.631361 | 2003 | 16803.5 | 14082 | 1 |
| cerebral endothelial cell adhesion molecule 1 (CEECAM1), mRNA | NP_057258.2 | NM_016174.3 | -1.518413 | 2014 | 16662.5 | 13757.75 | 0 |
| hypothetical protein FLJ22865 (FLJ22865), mRNA | NP_071384.1 | NM_022101.2 | -1.803469 | 2041.5 | 2598 | 2337 | 0 |
| chromosome 8 open reading frame 102 (C8orf102), transcript variant 1, mRNA | NP_064592.1 | NM_020207.2 | -1.369819 | 2049 | 16457.5 | 13970 | 1 |
| pleckstrin and Sec7 domain containing 3 (PSD3), transcript variant 1, mRNA | NP_056125.2 | NM_015310.2 | -1.395391 | 2072 | 14023 | 13223.25 | 0 |
| zinc finger, FYVE domain containing 21 (ZFYVE21), mRNA | NP_076976.1 | NM_024071.2 | -1.579562 | 2084 | 2994.5 | 2740.25 | 0 |
| forkhead box E1 (thyroid transcription factor 2) (FOXE1), mRNA | NP_004464.2 | NM_004473.3 | -1.878852 | 2107 | 7269 | 5293.75 | 0 |

Fig. 4 (continued)

| Gene name/symbol | protein accession | mRNA ref seq accession | median fold change | rank score | tumour tissue median intensity rank | non-malignant tissue median intensity rank | blood EST number |
|---|---|---|---|---|---|---|---|
| Myc-induced mitochondria protein (mimitin), mRNA | NP_777549.1 | NM_174889.2 | -1.474873 | 2151.5 | 9215 | 7030.25 | 1 |
| similar to developmental pluripotency associated 5; embryonal stem cell specific gene 1 (LOC341912), mRNA | XP_292301.3 | XM_292301.3 | -1.639786 | 2155 | 18561.5 | 12815.25 | 1 |
| hepcidin antimicrobial peptide (HAMP), mRNA | NP_066998.1 | NM_021175.2 | -1.279742 | 2205.5 | 3722.5 | 3385.25 | 0 |
| hypothetical protein BC009862 (LOC90113), mRNA | XP_291077.3 | XM_291077.3 | -1.768275 | 2221.5 | 6261.5 | 5176 | 0 |
| tripartite motif-containing 10 (TRIM10), transcript variant 1, mRNA | NP_006768.1 | NM_006778.2 | -1.750912 | 2296.5 | 4089.5 | 1565.5 | 0 |
| fksg17 fksg17 | | NM_032031 | -1.576144 | 2320.5 | 2050 | 1701.75 | 1 |
| LIM homeobox 9 (LHX9), transcript variant 1, mRNA | NP_064589.2 | NM_020204.2 | -1.374971 | 2333.5 | 16168 | 13872.25 | 0 |
| G protein-coupled receptor 51 (GPR51), mRNA | NP_005449.5 | NM_005458.5 | -1.309185 | 2361 | 3420 | 2488.25 | 0 |
| cdna: fj21394 fis clone col03536 unnamed protein product | | AK025047 | -2.258109 | 2387.5 | 17288 | 11926.75 | 0 |
| GPI anchored molecule like protein (GML), mRNA | NP_002057.1 | NM_002066.1 | -1.438045 | 2405 | 16818 | 14265.75 | 0 |
| programmed cell death 1 (PDCD1), mRNA | NP_005009.1 | NM_005018.1 | -1.519488 | 2537 | 8575 | 7118.5 | 0 |
| cadherin 20, type 2 (CDH20), mRNA | NP_114097.2 | NM_031891.2 | -1.393019 | 2538 | 15588 | 12275.75 | 0 |
| glycine dehydrogenase (decarboxylating; glycine decarboxylase, glycine cleavage system protein P) (GLDC), mRNA | NP_000161.1 | NM_000170.1 | -1.405054 | 2542.5 | 6039 | 4550.5 | 1 |
| protease, serine, 35 (PRSS35), mRNA | NP_699193.1 | NM_153362.1 | -1.45161B | 2545 | 16909 | 14109 | 0 |

| ratio | sensitivity (%) | specificity (%) |
|---|---|---|
| MDK/LTB4DH | 87 | 81 |
| IGFBP5/LTB4DH | 87 | 88 |
| HoxA13/LTB4DH | 65 | 81 | b.

| combination test | sensitivity (%) | specificity (%) |
|---|---|---|
| MDK/LTB4DH and IGFBP5/LTB4DH | 92 | 98 |
| MDK/LTB4DH and HoxA13/LTB4DH | 88 | 86 |
| IGFBP5/LTB4DH and HoxA13/LTB4DH | 83 | 98 |

Fig. 6

Fig. 8a: Combination test with MDK/LTB4DH and IGFBP5/LTB4DH
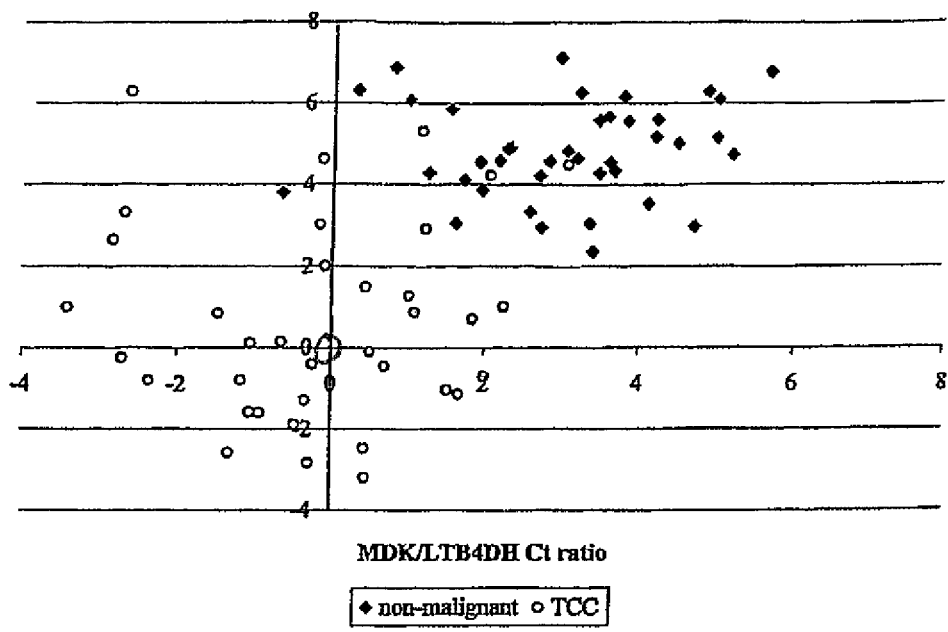
MDK/LTB4DH Ct ratio
♦ non-malignant   o TCC
Fig. 8b: Combination test with MDK/LTB4DH and HoxA13/LTB4DH
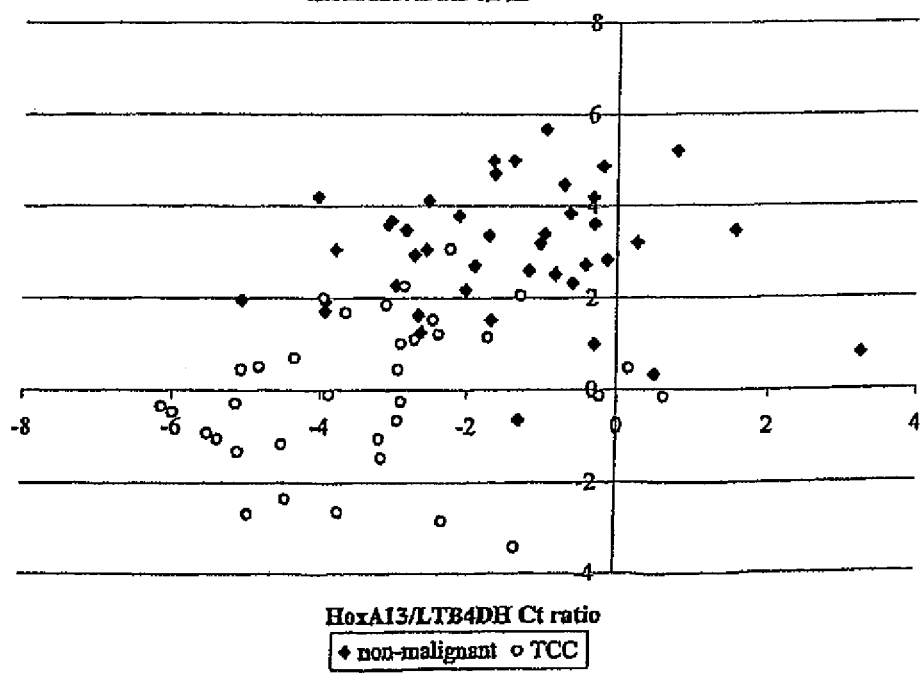
HoxA13/LTB4DH Ct ratio
♦ non-malignant   o TCC

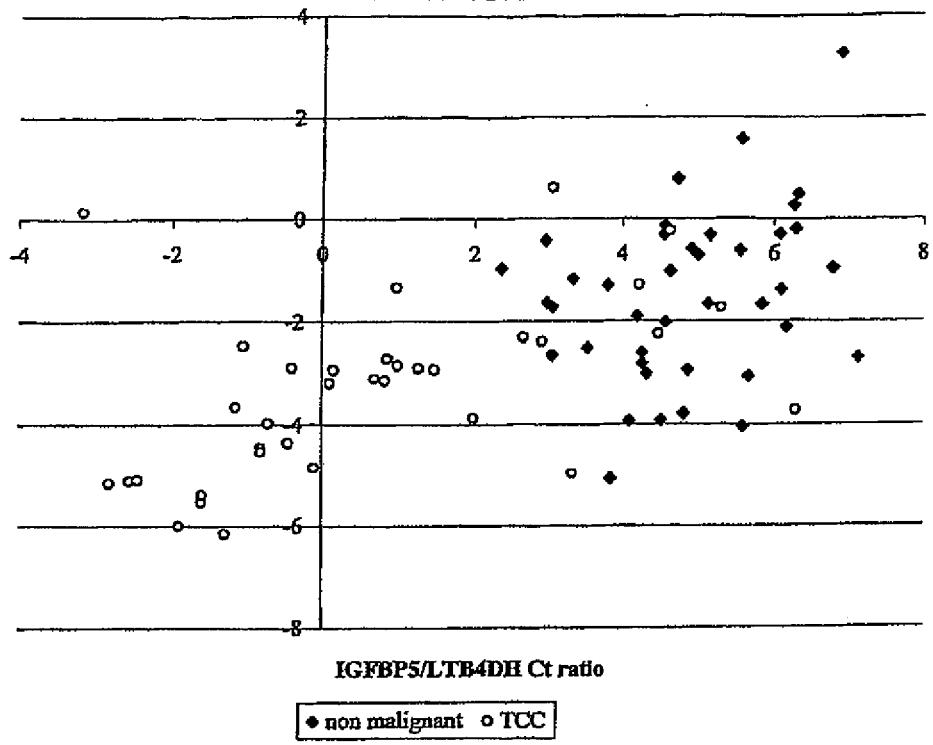
Fig. 8c: Combination test with IGFBP5/LTB4DH and HoxA13/LTB4DH
IGFBP5/LTB4DH Ct ratio
● non malignant  ○ TCC
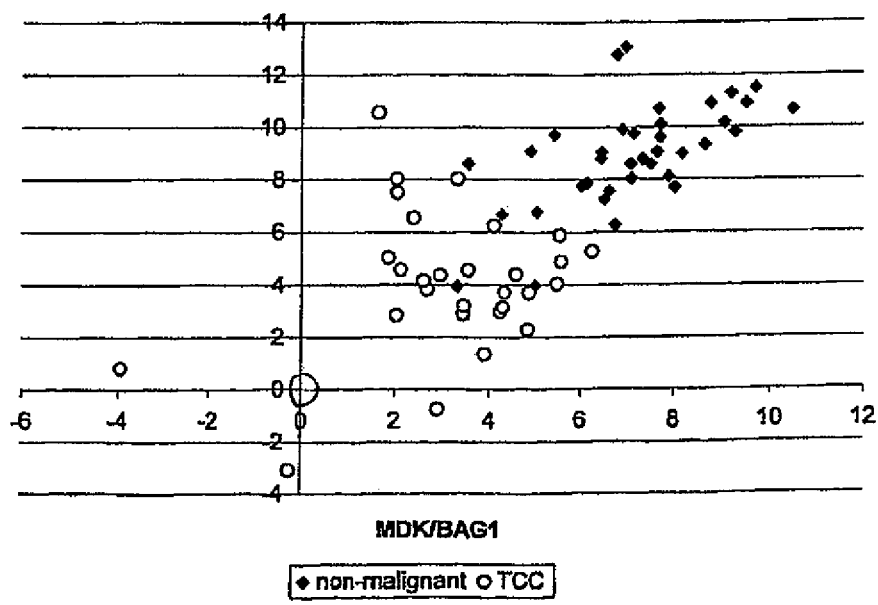
Fig 8d: Combination Test with MDK/BAG1 and IGFBP5/BAG1
MDK/BAG1
● non-malignant  ○ TCC

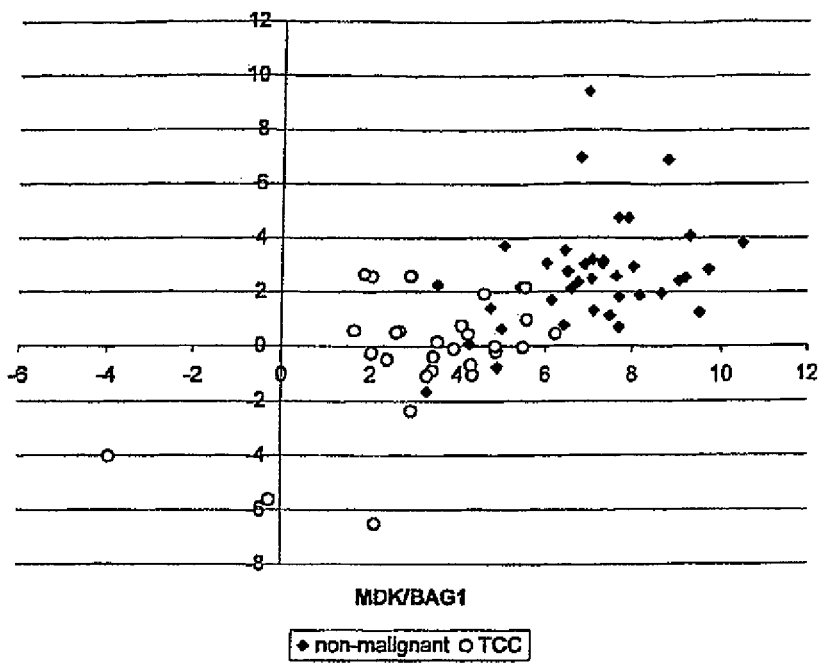

Fig. 8e: Combination test with MDK/BAG1 and HoxA13/BAG1

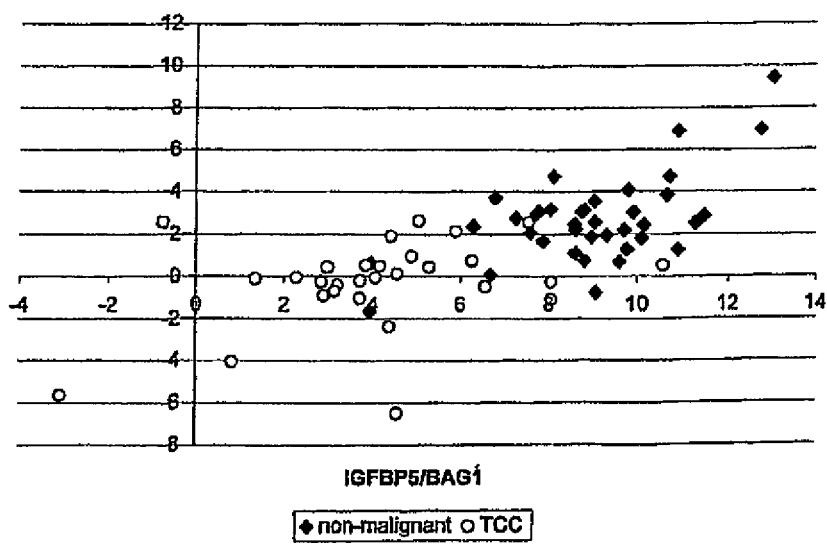

Fig. 8f: Combination test with IGFBP5/BAG1 and HoxA13/BAG1

Figure 8. Scatter plots showing the use of test combinations to discriminate between urine samples from TCC patients and controls with non-malignant disease. 8a. MDK/LTB4DH and IGFBP5/LTB4DH; 8b. MDK/LTB4DH and HoxA13/LTB4DH; 8c. IGFBP5/LTB4DH and HoxA13/LTB4DH; 8d. MDK/BAG1 and IGFBP5/BAG1; 8e. MDK/BAG1 and HoxA13/BAG1; 8f. IGFBP5/BAG1 and HoxA13/BAG1.

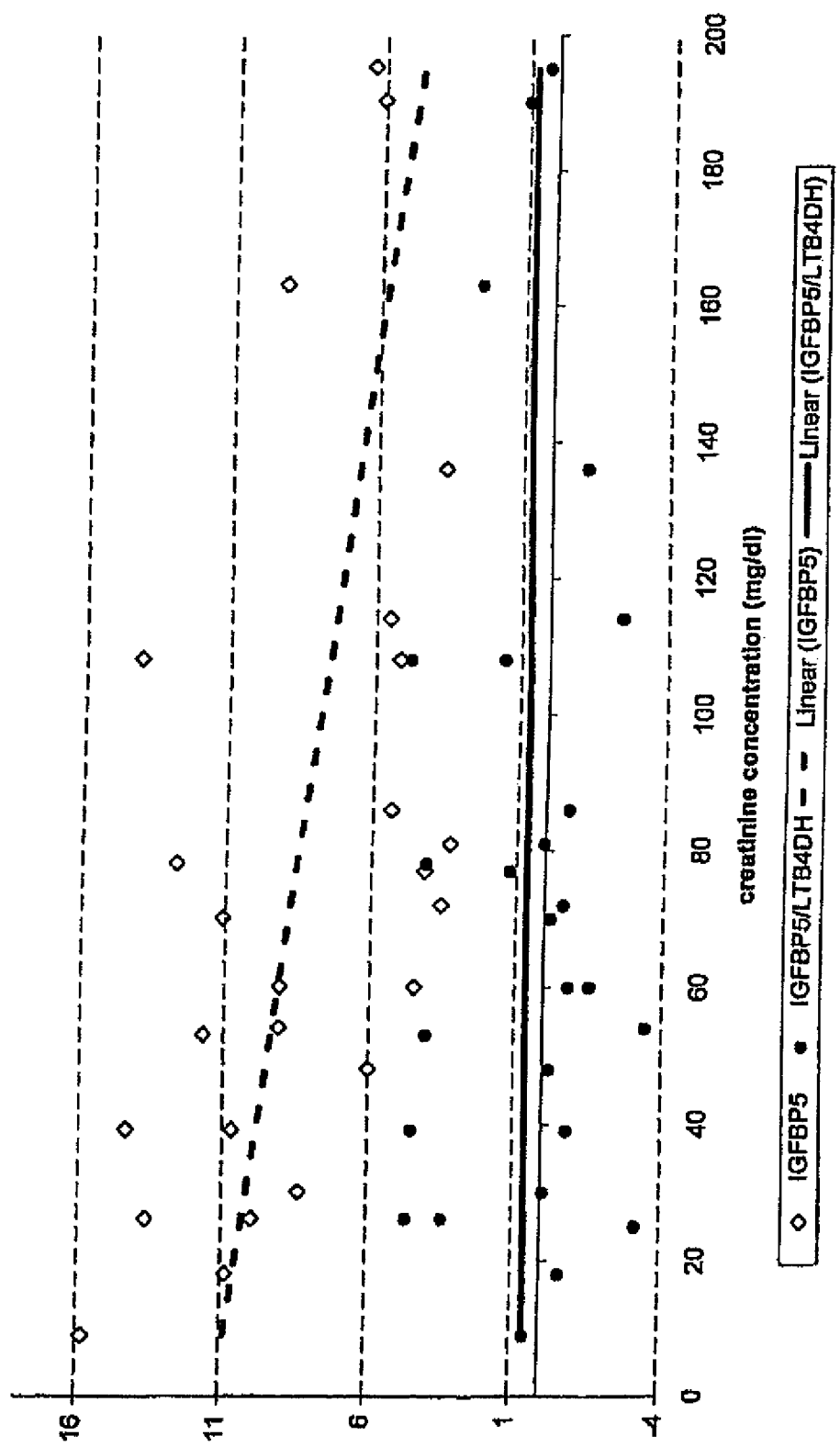
Fig. 9a: IGFBP5 and IGFBP5/LTB4DH vs creatinine concentration: TCC samples

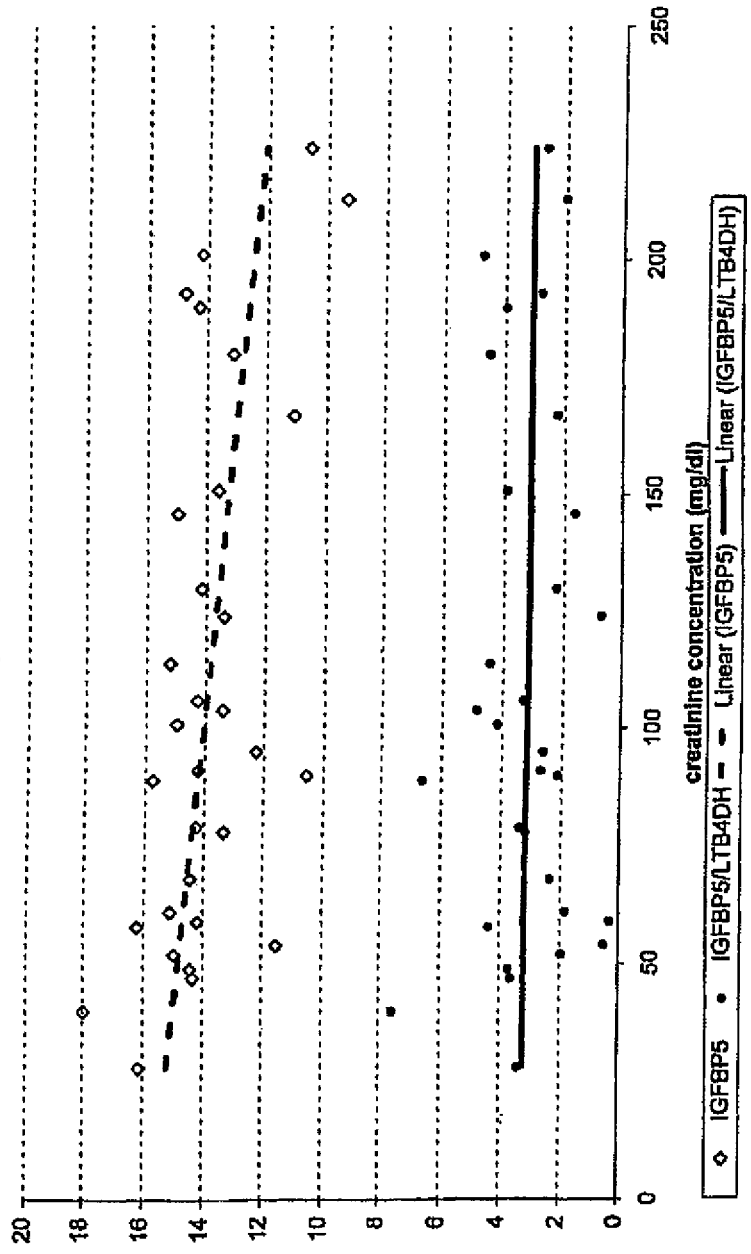
Figure 9. Scatter plots showing the correlation between ΔCt for IGFBP5 and ΔCt ratios for IGFBP5/LTB4DH and urine creatinine concentration.
9a. Urine samples from patients with TCC.
9b. Urine samples from patients with non-malignant disease.

Fig. 10a: MDK - catheterised and voided samples
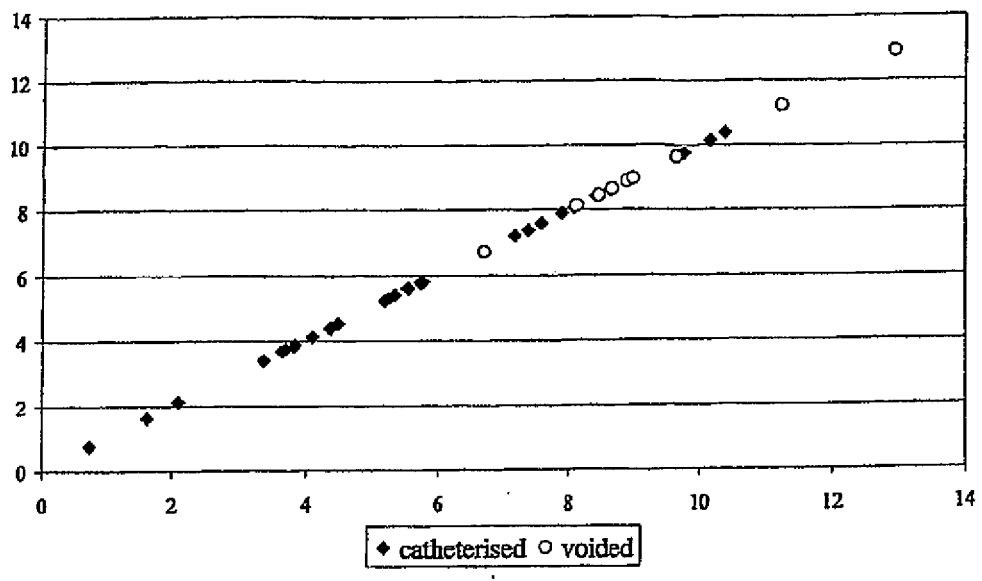
Fig. 10b: MDK/LTB4DH -catheterised and voided samples
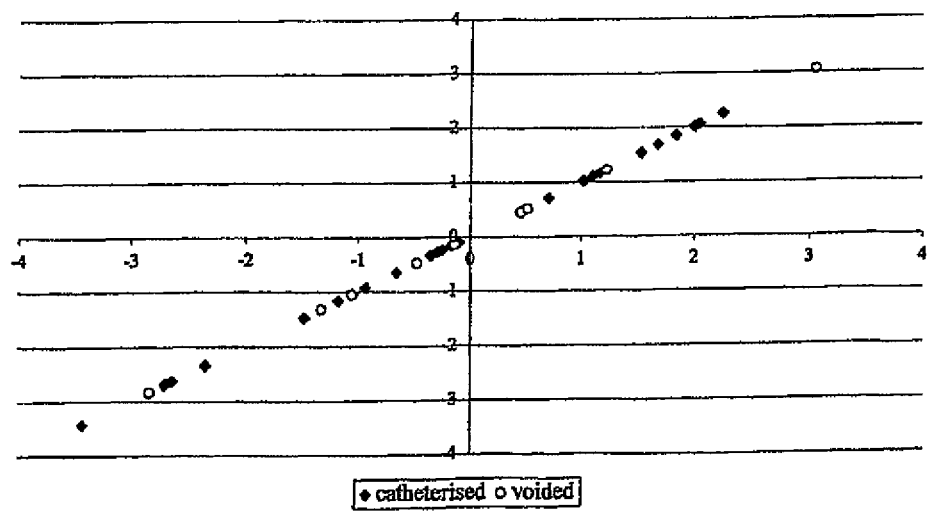

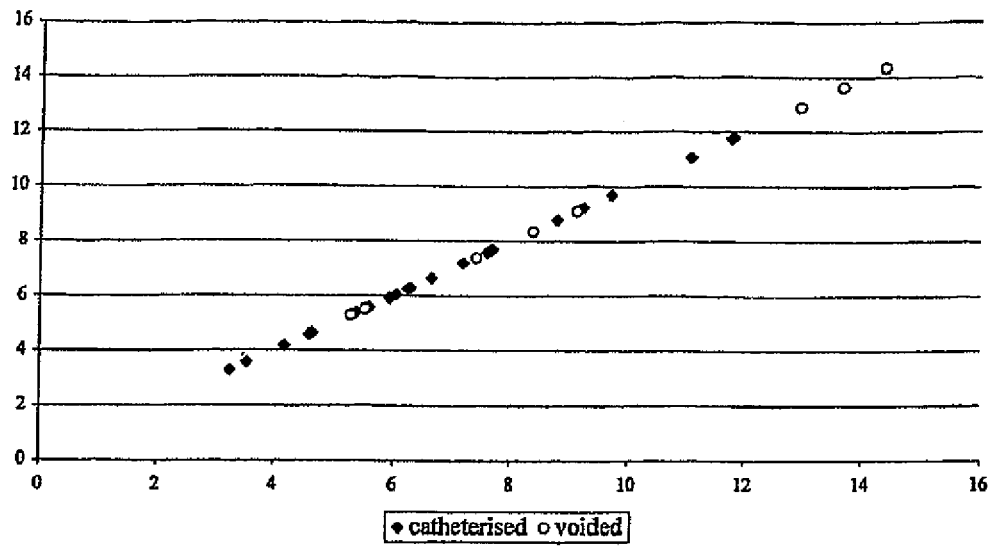
Fig. 10c: IGFBP5 - catheterised and voided samples
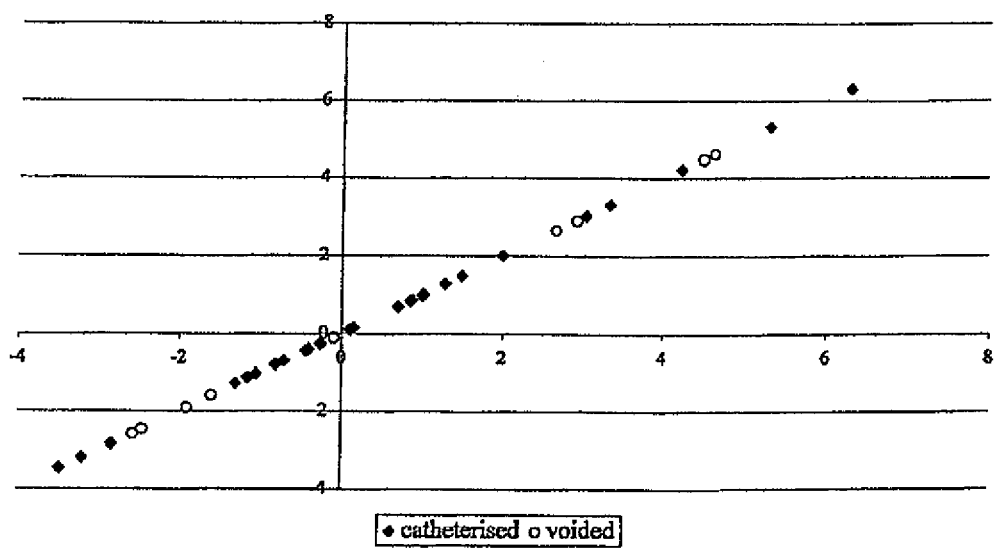
Fig. 10d: IGFBP5/LTB4DH -catheterised and voided samples Fig. 10e: HoxA13 - catheterised and voided samples
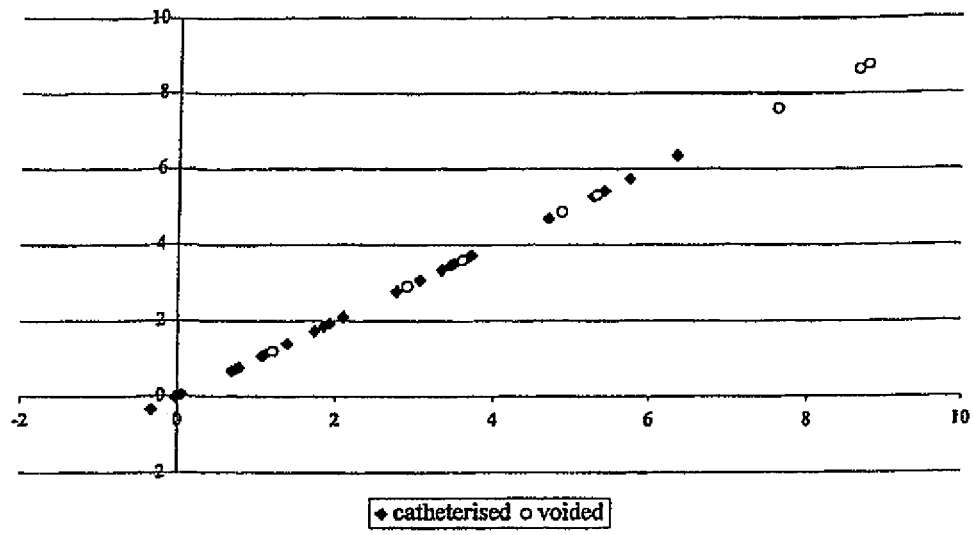
Fig. 10f: HoxA13/LTB4DH -catheterised and voided samples
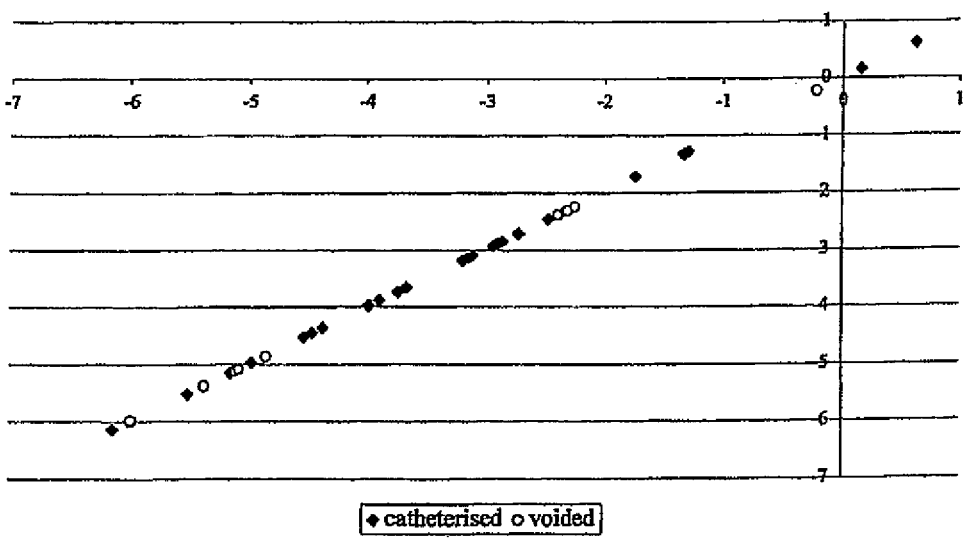
Figure 10a. Self-self scatter plots showing the distribution of voided and catheterised samples from TCC patients analysed using BTMs alone and BTMs in ratios with LTB4DH. 10a. MDK; 10b. MDK/LTB4DH; 10c. IGFBP5; 10d. IGFBP5/LTB4DH; 10e. HoxA13; 10f. HoxA13/LTB4DH.

| Gene Name | HUGO | MWG oligo # | NCBI mRNA ref seq | Protein ref seq | mean fold change | max fold change | T-test | Wilcoxon test | Summated rank | Serum |
|---|---|---|---|---|---|---|---|---|---|---|
| gamma-glutamyl hydrolase | GGH | mwghuman3 0K#A:03601 | NM_003878.1 | NP_003869.1 | 2.7 | 7.5 | 2.78E-08 | 3.63E-09 | 102 | s |
| secreted phosphoprotein 1 | SPP1 | mwghuman3 0K#A:09441 | NM_000582.2 | NP_000573.1 | 5.1 | 28.6 | 3.04E-08 | 0.000000525 | 143.5 | s |
| neuritin 1 | NRN1 | mwghuman3 0K#A:00858 | NM_016588.2 | NP_057672.1 | 3.9 | 54.8 | 1.93E-07 | 0.000000265 | 232 | s |
| secreted protein, acidic, cysteine-rich (osteonectin) | SPARC | mwghuman3 0K#A:08082 | NM_031118.2 | NP_003109.1 | 2.5 | 6.9 | 2.8E-07 | 0.00000013 | 352.5 | s |
| a disintegrin-like and metalloprotease (reprolysin type) with thrombospondin type 1 motif | ADAMTS10 | mwghuman3 0K#B:1355 | NM_030957.1 | NP_122219.2 | 2.7 | 26.8 | 2.27E-06 | 0.000000858 | 465 | s |
| contactin 1 | CNTN1 | mwghuman3 0K#A:01591 | NM_175038.1 | NP_778203.1 | 1.9 | 5.3 | 2.61E-06 | 0.00000198 | 805 | s |
| tolloid-like 2 | TLL2 | mwghuman3 0K#A:02932 | NM_012465.2 | NP_036597.1 | 3.9 | 35.6 | 0.0000207 | 0.0000466 | 1019 | s |
| protein disulfide isomerase-related | PDIR | mwghuman3 0K#A:03506 | NM_006810.1 | NP_006801.1 | 1.6 | 3.3 | 0.0000220 | 0.00000785 | 1044.5 | s |
| fibrillin 1 | FBN1 | mwghuman3 0K#A:07105 | NM_000138.2 | NP_000129.2 | 2.1 | 7.9 | 2.822E-06 | 1.37393E-06 | 1072.5 | s |
| KIAA0100 gene product | | mwghuman3 0K#A:10752 | NM_014680.2 | NP_055495.2 | 1.5 | 2.3 | 1.65E-06 | 0.00000187 | 1100.5 | s |
| calreticulin | CALR | mwghuman3 0K#A:10360 | NM_004343.2 | NP_004334.1 | 1.7 | 3.4 | 5.39E-06 | 0.00000518 | 1123.5 | s |
| integrin, beta-like 1 | ITGBL1 | mwghuman3 0K#A:07933 | NM_004791.1 | NP_004782.1 | 1.9 | 10.5 | 0.0000293 | 0.0000224 | 1186 | s |
| elastase 3B, pancreatic | ELA3B | mwghuman3 0K#B:3993 | NM_007352.1 | NP_031378.1 | 1.4 | 2.1 | 1.65E-06 | 0.00000785 | 1239.5 | s |
| SPARC related modular calcium binding 2 | SMOC2 | mwghuman3 0K#B:0260 | NM_022138.1 | NP_071421.1 | 1.6 | 4.3 | 0.0000069 | 0.00000547 | 1280 | s |

Fig. 11

| Gene Name | HUGO | MWG oligo # | NCBI mRNA ref seq | Protein ref seq | mean fold change | max fold change | T-test | Wilcoxon test | Summated rank | Serum |
|---|---|---|---|---|---|---|---|---|---|---|
| hexosaminidase A (alpha polypeptide) | HEXA | mwghuman3 OK#B:9777 | NM_000520.2 | NP_000511.1 | 1.9 | 14.6 | 0.0000183 | 0.0000325 | 1318.5 | s |
| insulin-like growth factor binding protein 7 | IGFBP7 | mwghuman3 OK#A:03385 | NM_001553.1 | NP_001544.1 | 2.0 | 6.5 | 0.0000614 | 0.000059 | 1554.5 | s |
| microfibrillar-associated protein 2 | MFAP2 | mwghuman3 OK#B:3055 | NM_017459.1 | NP_059453.1 | 1.6 | 4.9 | 0.0000388 | 0.0000466 | 1565.5 | s |
| cartilage intermediate layer protein, nucleotide pyrophosphohydrolase | CILP | mwghuman3 OK#A:00019 | NM_003613.1 | NP_003604.2 | 1.5 | 2.7 | 0.0000323 | 0.0000254 | 1582 | s |
| olfactomedin 1 | OLFM1 | mwghuman3 OK#B:3555 | NM_058199.2 | NP_478106.1 | 2.3 | 20.7 | 0.0000508 | 0.0000254 | 1704 | s |
| lumican | LUM | mwghuman3 OK#A:09199 | NM_002345.2 | NP_002336.1 | 2.8 | 25.0 | 0.0002509 | 6.82502E-05 | 1953 | s |
| midkine (neurite growth-promoting factor 2) | MDK | mwghuman3 OK#A:016650 | NM_002391.2 | NP_002382.1 | 1.8 | 8.9 | 0.0002901 | 5.24719E-05 | 2897 | s |
| semaphorin (LOC56920) | SEM2 | mwghuman3 OK#A:05073 | NM_020163.1 | NP_064548.1 | 1.4 | 2.2 | 7.236E-05 | 0.000118474 | 2920 | s |
| protease, serine, 11 | PRSS11 | mwghuman3 OK#B:1274 | NM_002775.2 | NP_002766.1 | 1.5 | 5.4 | 0.0002849 | 9.32339E-05 | 3896.5 | s |
| sulfatase 1 | SULF1 | mwghuman3 OK#B:8770 | NM_015170.1 | NP_055985.1 | 3.2 | 60.9 | 0.0025727 | 0.000797894 | 4138.5 | s |
| serine (or cysteine) proteinase inhibitor, clade H (heat shock protein 47), member 1 | SERPINH1 | mwghuman3 OK#A:08615 | NM_001235.2 | NP_001226.2 | 1.5 | 2.7 | 5.232E-05 | 0.000221711 | 4391 | s |
| matrix Gla protein | MGP | mwghuman3 OK#B:4003 | NM_000900.2 | NP_000891.2 | 2.6 | 47.9 | 0.0011611 | 0.001781807 | 5134 | s |

Fig. 11 (continued)

| Gene Name | HUGO | MWG oligo # | NCBI mRNA ref seq | Protein ref seq | mean fold change | max fold change | T-test | Wilcoxon test | Summated rank | Serum |
|---|---|---|---|---|---|---|---|---|---|---|
| tissue inhibitor of metalloproteinase 1 | TIMP1 | mwghuman3 OK#A:08048 | NM_003254.1 | NP_003245.1 | 1.8 | 4.4 | 0.0010783 | 0.006400169 | 7533 | s |
| EGF-like-domain, multiple 6 | EGFL6 | mwghuman3 OK#A:07688 | NM_015507.2 | NP_056322.2 | 1.5 | 3.4 | 0.0042021 | 0.00857023 | 8467 | s |
| sperm associated antigen 11 | SPAG11 | mwghuman3 OK#B:1373 | NM_058203.1 | NP_478110.1 | 1.3 | 4.2 | 0.0015737 | 0.001050446 | 10850 | s |
| insulin-like growth factor binding protein 5 | IGFBP5 | mwghuman3 OK#C:1077 | NM_000599.2 | NP_000590.1 | 1.7 | 8.5 | 0.0097847 | 0.03386216 | 10980.5 | s |
| sema domain, immunoglobulin domain (Ig), short basic domain, secreted, (semaphorin) 3F | SEMA3F | mwghuman3 OK#A:07262 | NM_004186.2 | NP_004177.2 | -1.1 | 17.2 | 0.4328626 | 0.5041839 | NA | |
| cell division cycle 2, G1 to S and G2 to M | CDC2 | mwghuman3 OK#A:05382 | NM_033379.2 | NP_203698.1 | 5.3 | 16.5 | 1.87E-12 | 6.12E-11 | 6 | |
| topoisomerase (DNA) II alpha | TOP2A | mwghuman3 OK#B:7144 | NM_001067.2 | NP_001058.2 | 3.6 | 7.5 | 5.33E-11 | 1.32E-09 | 28.5 | |
| ubiquitin-conjugating enzyme E2C | UBE2C | mwghuman3 OK#A:01776 | NM_181803.1 | NP_861519.1 | 4.6 | 34.3 | 6.82E-10 | 1.01E-09 | 29.5 | |
| stathmin 1 | STMN1 | mwghuman3 OK#A:00925 | NM_203401.1 | NP_981946.1 | 3.2 | 11.4 | 7.66E-10 | 3.63E-09 | 44 | |
| tubulin, alpha 4 | TUBA4 | mwghuman3 OK#B:2461 | NM_025019.1 | NP_079295.1 | 2.8 | 4.5 | 3.1E-09 | 1.32E-09 | 82.5 | |
| histone 1, H1b | HIST1H1B | mwghuman3 OK#A:05716 | NM_005322.2 | NP_005313.1 | 2.3 | 5.7 | 1.77E-11 | 4.42E-12 | 93 | |
| high-mobility group box 2 | HMGB2 | mwghuman3 OK#B:3849 | NM_002129.2 | NP_002120.1 | 2.6 | 5.6 | 7.85E-09 | 1.44E-08 | 95.5 | |
| cyclin A2 | CCNA2 | mwghuman3 OK#A:04253 | NM_001237.2 | NP_001228.1 | 2.9 | 8.4 | 3.87E-08 | 5.85E-09 | 129.5 | |
| cell division cycle associated 1 | CDCA1 | mwghuman3 OK#B:9471 | NM_145697.1 | NP_663735.1 | 2.4 | 8.2 | 1.85E-09 | 5.85E-09 | 151.5 | |

Fig. 11 (continued)

| Gene Name | HUGO | MWG oligo # | NCBI mRNA ref seq | Protein ref seq | mean fold change | max fold change | T-test | Wilcoxon test | Summated rank | Serum |
|---|---|---|---|---|---|---|---|---|---|---|
| hypothetical protein MGC5576 | | mwghuman3 OK#A:03766 | NM_024058.2 | NP_076961.1 | 2.1 | 4.6 | 6.35E-09 | 9.25E-09 | 171 | |
| DEK oncogene | DEK | mwghuman3 OK#B:2969 | NM_003472.2 | NP_003463.1 | 2.4 | 6.2 | 1.11E-07 | 1.44E-08 | 173.5 | |
| MLF1 interacting protein | MLF1IP | mwghuman3 OK#C:8650 | NM_024629.2 | NP_078905.2 | 2.3 | 4.6 | 2.22E-07 | 6.07E-08 | 209.5 | |
| cell division cycle associated 8 | CDCA8 | mwghuman3 OK#A:07906 | NM_018101.1 | NP_060571.1 | 2.3 | 4.1 | 2.8E-07 | 4.99E-08 | 212 | |
| hypothetical protein FLJ26647 | | mwghuman3 OK#A:03566 | NM_017818.3 | NP_060388.1 | 2.2 | 4.6 | 1.5E-07 | 0.000000109 | 216 | |
| thymidylate synthetase | TYMS | mwghuman3 OK#A:10045 | NM_001071.1 | NP_001062.1 | 2.2 | 5.0 | 1.48E-07 | 2.72E-08 | 232.5 | |
| SMC4 structural maintenance of chromosomes 4-like 1 (yeast) | SMC4L1 | mwghuman3 OK#A:05848 | NM_0010027 99.1 | NP_0010027 99.1 | 2.4 | 5.7 | 5.7E-07 | 0.000000525 | 264.5 | |
| v-yes-1 Yamaguchi sarcoma viral related oncogene homolog | LYN | mwghuman3 OK#C:2653 | NM_002350.1 | NP_002341.1 | 1.9 | 4.5 | 8.07E-08 | 0.000000285 | 267 | |
| high-mobility group box 3 | HMGB3 | mwghuman3 OK#A:01602 | NM_005342.1 | NP_005333.1 | 1.9 | 5.0 | 2.13E-10 | 6.12E-11 | 268 | |
| prostaglandin I2 (prostacyclin) receptor | PTGIR | mwghuman3 OK#A:00298 | NM_000960.3 | NP_000951.1 | 3.2 | 31.5 | 3.59E-07 | 4.09E-08 | 270.5 | |
| downstream neighbor of SON (DONSON) | DONSON | mwghuman3 OK#A:05883 | NM_145795.1 | NP_665738.1 | 1.8 | 3.3 | 2.74E-08 | 4.09E-08 | 279.5 | |
| hyaluronan-mediated motility receptor | HMMR | mwghuman3 OK#A:02702 | NM_012485.1 | NP_036817.1 | 2.7 | 6.8 | 1.84E-06 | 0.000000729 | 281 | |
| claudin 8 | CLDN8 | mwghuman3 OK#A:08357 | NM_021195.3 | NP_067018.1 | 3.2 | 39.1 | 7.89E-07 | 6.07E-08 | 288.5 | |
| histone 1, H1d | HIST1H1D | mwghuman3 OK#C:1892 | NM_005320.2 | NP_005311.1 | 2.1 | 4.8 | 4.46E-06 | 7.37E-08 | 306.5 | |

Fig. 11 (continued)

| Gene Name | HUGO | MWG oligo # | NCBI mRNA ref seq | Protein ref seq | mean fold change | max fold change | T-test | Wilcoxon test | Summated rank | Serum |
|---|---|---|---|---|---|---|---|---|---|---|
| chromosome 10 open reading frame 3 | C10orf3 | mwghuman3 OK#A:01878 | NM_018131.3 | NP_060601.2 | 2.1 | 4.3 | 9.03E-08 | 6.07E-08 | 308.5 | |
| kinetochore associated 1 | KNTC1 | mwghuman3 OK#A:05391 | NM_014708.3 | NP_055523.1 | 2.2 | 4.2 | 2.32E-07 | 0.000000265 | 325 | |
| CDC28 protein kinase regulatory subunit 1B | CKS1B | mwghuman3 OK#C:06349 | NM_001826.1 | NP_001817.1 | 2.1 | 3.4 | 1.7E-08 | 4.99E-08 | 332 | |
| ribonucleotide reductase M2 polypeptide | RRM2 | mwghuman3 OK#B:3501 | NM_001034.1 | NP_001025.1 | 2.6 | 18.6 | 0.0000015 | 0.000000856 | 344 | |
| histone 1, H2bh | HIST1H2BH | mwghuman3 OK#B:2977 | NM_003524.2 | NP_003515.1 | 3.1 | 15.3 | 0.0000011 | 0.000000794 | 349 | |
| serine/threonine kinase 6 | STK6 | mwghuman3 OK#A:04814 | NM_198437.1 | NP_940839.1 | 2.6 | 26.9 | 1.67E-06 | 7.37E-08 | 349.5 | |
| M-phase phosphoprotein 1 | MPHOSPH1 | mwghuman3 OK#A:09885 | NM_016195.2 | NP_057279.2 | 1.9 | 3.8 | 3.29E-07 | 0.00000137 | 359.5 | |
| cyclin B2 | CCNB2 | mwghuman3 OK#A:03606 | NM_004701.2 | NP_004692.1 | 2.0 | 3.4 | 6.19E-07 | 7.37E-09 | 373.5 | |
| G protein-coupled receptor 32 | GPR32 | mwghuman3 OK#A:03297 | NM_001506.1 | NP_001497.1 | 3.4 | 42.0 | 1.26E-06 | 0.000000856 | 390 | |
| endoglin | ENG | mwghuman3 OK#A:05668 | NM_000118.1 | NP_000109.1 | 1.9 | 5.3 | 4.49E-07 | 0.000000525 | 418.5 | |
| malignant fibrous histiocytoma amplified sequence 1 MFHAS1 | MFHAS1 | mwghuman3 OK#A:04639 | NM_004225.1 | NP_004216.1 | 2.4 | 11.0 | 2.17E-07 | 0.000000243 | 425 | |
| histone 1, H1c | HIST1H1C | mwghuman3 OK#A:07773 | NM_005319.3 | NP_005310.1 | 2.3 | 10.0 | 3.71E-07 | 0.000000375 | 425 | |
| arginine vasopressin receptor 2 | AVPR2 | mwghuman3 OK#A:01219 | NM_000054.2 | NP_000045.1 | 2.3 | 22.3 | 8.93E-07 | 6.07E-08 | 427.5 | |
| centromere protein F | CENPF | mwghuman3 OK#A:06471 | NM_016343.2 | NP_057427.3 | 1.7 | 2.6 | 2.51E-07 | 1.17584E-08 | 435.5 | |
| homeo box A13 | HOXA13 | mwghuman3 OK#A:08971 | NM_000522.2 | NP_000513.2 | 1.7 | 3.5 | 2.61E-07 | 0.000000619 | 439.5 | |

Fig. 11 (continued)

| Gene Name | HUGO | MWG oligo # | NCBI mRNA ref seq | Protein ref seq | mean fold change | max fold change | T-test | Wilcoxon test | Summated rank | Serum |
|---|---|---|---|---|---|---|---|---|---|---|
| H4 histone family, member g | | mwghuman3 OK#A:01329 | XM_030144 | | | | | | | |
| MGC27121 gene | | mwghuman3 OK#C:3953 | NM_0010013 43.1 | NP_0010013 43.1 | 3.0 | 13.2 | 2.33E-06 | 0.00000179 | 463 | |
| nucleoside phosphorylase | NP | mwghuman3 OK#A:03762 | NM_000270.1 | NP_000281.1 | 3.6 | 46.3 | 1.891E-03 | 5.18452E-06 | 481.5 | |
| asp (abnormal spindle)-like, microcephaly associated | ASPM | mwghuman3 OK#A:01367 | NM_018136.2 | NP_080606.2 | 1.9 | 4.2 | 2.7E-07 | 0.000000375 | 497 | |
| hypothetical protein flj11871 | | mwghuman3 OK#A:10682 | NM_025117 | | 2.4 | 14.5 | 7.55E-07 | 0.00000187 | 504.5 | |
| likely ortholog of mouse limb-bud and heart gene | LBH | mwghuman3 OK#B:7280 | NM_030915.1 | NP_112177.1 | 2.0 | 13.2 | 1.96E-06 | 0.000001 | 511 | |
| nudix (nucleoside diphosphate linked moiety X)-type motif 1 | NUDT1 | mwghuman3 OK#A:05916 | NM_198954.1 | NP_945192.1 | 1.7 | 4.7 | 2.64E-07 | 0.000000223 | 528 | |
| lymphoid-specific helicase, | HELLS | mwghuman3 OK#A:00387 | NM_018063.3 | NP_060533.2 | 1.9 | 3.7 | 5.12E-08 | 0.000000444 | 546.5 | |
| ankyrin repeat and SOCS box-containing 9 | ASB9 | mwghuman3 OK#A:01131 | NM_024087.1 | NP_076892.1 | 1.8 | 4.3 | 5.874E-07 | 3.74678E-07 | 550 | |
| MCM5 minichromosome maintenance deficient 5 | MCM5 | mwghuman3 OK#A:07747 | NM_006739.2 | NP_006730.2 | 1.7 | 5.9 | 1.27E-06 | 0.0000016 | 556 | |
| IGF-II mRNA-binding protein 2 | IMP-2 | mwghuman3 OK#A:09784 | NM_006548.3 | NP_006539.2 | 1.7 | 3.3 | 7.831E-06 | 1.55499E-07 | 557.5 | |
| hypothetical protein DKFZp566M1046 | DKFZP566 M1046 | mwghuman3 OK#B:8751 | NM_032127.1 | NP_115503.1 | 2.1 | 4.9 | 3.964E-06 | 1.17464E-05 | 575 | |
| tubulin, alpha 2 | TUBA2 | mwghuman3 OK#B:4654 | NM_079336.1 | NP_524575.1 | 1.8 | 5.7 | 2.214E-06 | 1.37393E-06 | 594.5 | |
| growth arrest-specific 2 like 3 | GAS2L3 | mwghuman3 OK#C:3659 | NM_174942.1 | NP_777602.1 | 1.8 | 3.9 | 6.73E-07 | 0.00000217 | 602 | |
| | | | | | 2.0 | 5.6 | 7.484E-07 | 2.91843E-06 | 604 | |

Fig. 11 (continued)

| Gene Name | HUGO | MWG oligo # | NCBI mRNA ref seq | Protein ref seq | mean fold change | max fold change | T-test | Wilcoxon test | Summated rank | Serum |
|---|---|---|---|---|---|---|---|---|---|---|
| hypothetical protein FLJ12442 | | mwghuman3 OK#B:2450 | NM_022908.1 | NP_075059.1 | 1.7 | 2.9 | 1.54E-08 | 3.63E-09 | 614 | |
| MCM6 minichromosome maintenance deficient 6 | MCM6 | mwghuman3 OK#B:8147 | NM_005915.4 | NP_005906.2 | 2.2 | 5.7 | 5.43E-07 | 0.000000232 | 653.5 | |
| docking protein 3 | DOK3 | mwghuman3 OK#B:2635 | NM_024872.1 | NP_079148.1 | 2.2 | 12.6 | 1.75E-06 | 4.99E-08 | 655 | |
| WD repeat domain 18 | WDR18 | mwghuman3 OK#B:3548 | NM_024100.2 | NP_077005.2 | 2.0 | 8.7 | 9.89E-07 | 4.99E-08 | 677 | |
| cytoskeleton associated protein 2 | CKAP2 | mwghuman3 OK#A:06670 | NM_018204.2 | NP_060674.2 | 1.8 | 4.3 | 3.108E-06 | 1.83626E-05 | 701.5 | |
| kinesin family member 20A | KIF20A | mwghuman3 OK#A:07988 | NM_005733.1 | NP_005724.1 | 1.9 | 2.8 | 1.045E-08 | 1.07593E-07 | 707.5 | |
| putative fap protein | | mwghuman3 OK#B:5292 | U63542 | | 2.1 | 18.9 | 4.98E-06 | 0.0000045 | 718 | |
| chromosome 6 open reading frame 32 | C6orf32 | mwghuman3 OK#A:04343 | NM_015864.2 | NP_056948.2 | 1.8 | 11.4 | 1.527E-07 | 1.29514E-07 | 721.5 | |
| NIMA (never in mitosis gene a)-related kinase 2 | NEK2 | mwghuman3 OK#A:00347 | NM_002497.2 | NP_002488.1 | 2.0 | 3.5 | 1.023E-05 | 3.37794E-06 | 732 | |
| cryptochrome 1 (photolyase-like) | CRY1 | mwghuman3 OK#A:03219 | NM_004075.2 | NP_004066.1 | 1.8 | 3.0 | 6.04E-06 | 0.000001 | 744 | |
| transglutaminase 2 | TGM2 | mwghuman3 OK#A:08571 | NM_004613.2 | NP_004604.2 | 2.0 | 8.3 | 1.498E-05 | 3.37794E-06 | 747 | |
| discs, large homolog 7 | DLG7 | mwghuman3 OK#B:7380 | NM_014750.3 | NP_055565.2 | 2.0 | 5.9 | 1.353E-05 | 1.17464E-05 | 748 | |
| eukaryotic translation initiation factor 2C | EIF2C2 | mwghuman3 OK#C:2267 | NM_0121154.2 | NP_036286.2 | 1.7 | 2.7 | 1.73E-08 | 9.25E-09 | 766 | |
| DEP domain containing 1 | DEPDC1 | mwghuman3 OK#B:7337 | NM_017779.3 | NP_060249.2 | 2.0 | 4.6 | 1.722E-06 | 3.15848E-07 | 776 | |
| histone 2, H4 | HIST2H4 | mwghuman3 OK#C:1932 | NM_003548.2 | NP_003539.1 | 1.7 | 2.7 | 3.279E-06 | 2.91943E-05 | 823 | |

Fig. 11 (continued)

| Gene Name | HUGO | MWG oligo # | NCBI mRNA ref seq | Protein ref seq | mean fold change | max fold change | T-test | Wilcoxon test | Summated rank | Serum |
|---|---|---|---|---|---|---|---|---|---|---|
| baculoviral IAP repeat-containing 5 (survivin) | BIRC5 | mwghuman3 OK#B:0833 | NM_001168.1 | NP_001159.1 | 2.6 | 54.8 | 4.87E-06 | 0.000000856 | 823 | |
| MCM7 minichromosome maintenance deficient 7 | MCM7 | mwghuman3 OK#B:7620 | NM_182776.1 | NP_877577.1 | 1.9 | 4.0 | 1.13E-06 | 0.0000103 | 829 | |
| methylthioadenosine phosphorylase | MTAP | mwghuman3 OK#B:8310 | AF102294.1 | AAD19841.1 | 2.3 | 13.3 | 1.033E-05 | 1.33979E-05 | 844.5 | |
| kinetochore associated 2 | KNTC2 | mwghuman3 OK#A:10053 | NM_006101.1 | NP_006092.1 | 1.5 | 2.9 | 1.169E-06 | 2.17032E-06 | 848 | |
| HSPC150 protein similar to ubiquitin-conjugating enzyme | HSPC150 | mwghuman3 OK#A:00955 | NM_014176.1 | NP_054895.1 | 1.9 | 3.4 | 1.782E-05 | 1.73522E-05 | 849.5 | |
| SMC6 structural maintenance of chromosomes 6-like 1 | SMC6L1 | mwghuman3 OK#A:05363 | NM_024624.2 | NP_078900.1 | 1.7 | 4.0 | 6.059E-06 | 1.28219E-05 | 852 | |
| histone 1, H2bc | HIST1H2B C | mwghuman3 OK#B:9593 | NM_003526.2 | NP_003517.2 | 1.9 | 5.3 | 7.83E-06 | 1.73822E-05 | 870 | |
| ASF1 anti-silencing function 1 homolog B | ASF1B | mwghuman3 OK#A:04415 | NM_018154.1 | NP_060824.1 | 1.7 | 4.1 | 1.04E-06 | 0.0000016 | 872 | |
| LDL receptor adaptor protein | ARH | mwghuman3 OK#B:2491 | NM_015627.1 | NP_058442.1 | 2.0 | 14.0 | 4.01E-06 | 0.000000155 | 872 | |
| lamin B1 | LMNB1 | mwghuman3 OK#A:02089 | NM_005573.2 | NP_005564.1 | 1.8 | 3.4 | 2.869E-05 | 1.52616E-05 | 891.5 | |
| hypothetical protein FLJ10719 | | mwghuman3 OK#B:2212 | NM_018193.1 | NP_060663.1 | 1.7 | 3.4 | 4.715E-06 | 8.98315E-06 | 894.5 | |
| hypothetical protein FLJ10706 | | mwghuman3 OK#A:00611 | NM_018188.2 | NP_060856.2 | 1.5 | 2.8 | 1.483E-06 | 1.00418E-05 | 913 | |
| MAD2 mitotic arrest deficient-like 1 | MAD2L1 | mwghuman3 OK#A:08367 | NM_002358.2 | NP_002349.1 | 1.8 | 3.9 | 1.058E-05 | 2.87228E-05 | 913.5 | |

Fig. 11 (continued)

| Gene Name | HUGO | MWG oligo # | NCBI mRNA ref seq | Protein ref seq | mean fold change | max fold change | T-test | Wilcoxon test | Summated rank | Serum |
|---|---|---|---|---|---|---|---|---|---|---|
| solute carrier family 22 | SLC22A2 | mwghuman3 OK#A:02704 | NM_153191.1 | NP_894861.1 | 3.2 | 31.3 | 0.0000171 | 0.0000287 | 915.5 | |
| hypothetical protein MGC34923 | | mwghuman3 OK#C:4473 | NM_144717.2 | NP_653318.2 | 1.9 | 8.7 | 6.72E-07 | 0.000000525 | 937.5 | |
| sperm associated antigen 5 | SPAG5 | mwghuman3 OK#A:07691 | NM_006461.2 | NP_006452.2 | 2.8 | 6.6 | 0.0000482 | 0.0000171 | 947 | |
| activin A receptor type II-like 1 | ACVRL1 | mwghuman3 OK#A:00470 | NM_000020.1 | NP_000011.1 | 1.5 | 2.4 | 6.94E-06 | 0.00000733 | 961 | |
| Down syndrome critical region gene 1 | DSCR1 | mwghuman3 OK#A:09846 | NM_004414.5 | NP_004405.3 | 1.5 | 2.7 | 1.119E-06 | 2.91943E-06 | 967 | |
| protease, serine, 15 | PRSS15 | mwghuman3 OK#A:03353 | NM_004793.2 | NP_004784.2 | 1.9 | 15.2 | 0.0000135 | 0.0000292 | 969 | |
| S100 calcium binding protein A9 | S100A9 | mwghuman3 OK#A:07436 | NM_002965.2 | NP_002956.1 | 4.1 | 44.0 | 0.0000071 | 0.0000525 | 975 | |
| MCM4 minichromosome maintenance deficient 4 | MCM4 | mwghuman3 OK#B:7681 | NM_182746.1 | NP_877423.1 | 1.6 | 3.9 | 0.0000039 | 0.00000785 | 989.5 | |
| suppression of tumorigenicity 7 like | ST7L | mwghuman3 OK#A:01391 | NM_138728.2 | NP_620056.1 | 2.0 | 13.4 | 7.64E-06 | 0.00000292 | 1001 | |
| pleckstrin homology domain containing, family A (phosphoinositide binding specific) member 4 | PLEKHA4 | mwghuman3 OK#B:3447 | NM_020904.1 | NP_065955.1 | 1.4 | 3.0 | 1.26E-07 | 0.000000444 | 1030.5 | |
| EphB1 | EPHB1 | mwghuman3 OK#A:00465 | NM_004441.2 | NP_004432.1 | 2.2 | 9.5 | 2.334E-05 | 1.52615E-05 | 1042.5 | |
| caldesmon 1 | CALD1 | mwghuman3 OK#A:07744 | NM_033140.2 | NP_149131.1 | 2.2 | 7.0 | 1.129E-05 | 8.32856E-05 | 1057 | |

Fig. 11 (continued)

| Gene Name | HUGO | MWG oligo # | NCBI mRNA ref seq | Protein ref seq | mean fold change | max fold change | T-test | Wilcoxon test | Summated rank | Serum |
|---|---|---|---|---|---|---|---|---|---|---|
| SMC1 structural maintenance of chromosomes 1-like 1 | SMC1L1 | mwghuman3 0K#A:05798 | NM_006306.2 | NP_006297.2 | 1.6 | 2.9 | 4.98E-06 | 0.0000134 | 1061.5 | |
| Thy-1 co-transcribed | | mwghuman3 0K#C:0578 | NM_033209.2 | NP_149866.1 | 1.8 | 4.7 | 1.15E-06 | 0.000000375 | 1074 | |
| RA-regulated nuclear matrix-associated protein | RAMP | mwghuman3 0K#A:03935 | NM_016448.1 | NP_057532.1 | 1.5 | 2.1 | 4.195E-07 | 7.28584E-07 | 1076 | |
| FK506 binding protein 11 | FKBP11 | mwghuman3 0K#A:07244 | NM_016594.1 | NP_057878.1 | 1.8 | 5.0 | 0.0000122 | 0.0000287 | 1088.5 | |
| chromosome 20 open reading frame 129 | C20orf129 | mwghuman3 0K#B:3850 | NM_030919.1 | NP_112181.1 | 1.6 | 2.4 | 2.438E-05 | 2.91943E-06 | 1106 | |
| histone 1, H4h | HIST1H4H | mwghuman3 0K#B:4596 | NM_003543.3 | NP_003534.1 | 2.1 | 6.4 | 0.0000344 | 0.000059 | 1117 | |
| cyclin-dependent kinase inhibitor 3 | CDKN3 | mwghuman3 0K#A:05799 | NM_005192.2 | NP_005183.2 | 2.1 | 4.7 | 7.871E-05 | 1.93626E-05 | 1117.5 | |
| melanoma cell adhesion molecule | MCAM | mwghuman3 0K#A:10599 | NM_006500.1 | NP_006491.1 | 1.6 | 3.0 | 1.81E-06 | 0.0000045 | 1135.5 | |
| synuclein, alpha interacting protein | SNCAIP | mwghuman3 0K#A:08103 | NM_005460.1 | NP_005451.1 | 1.7 | 2.7 | 0.0000151 | 0.0000236 | 1151.5 | |
| nipsnap homolog 1 | NIPSNAP1 | mwghuman3 0K#A:10699 | NM_003634.1 | NP_003625.1 | 2.4 | 21.5 | 0.0000194 | 0.0000153 | 1165.5 | |
| adaptor-related protein complex 1, mu 1 subunit | AP1M1 | mwghuman3 0K#B:1553 | NM_032493.2 | NP_115882.1 | 1.5 | 4.1 | 6.892E-08 | 8.99315E-06 | 1173.5 | |
| anillin, actin binding protein | ANLN | mwghuman3 0K#A:05280 | NM_018685.2 | NP_061155.2 | 2.6 | 7.7 | 0.0001 | 0.0000716 | 1177 | |
| chromosome 6 open reading frame 69 | C6orf69 | mwghuman3 0K#C:0854 | NM_173562.3 | NP_775833.2 | 1.8 | 3.6 | 3.55E-07 | 0.000000856 | 1187 | |

Fig. 11 (continued)

| Gene Name | HUGO | MWG oligo # | NCBI mRNA ref seq | Protein ref seq | mean fold change | max fold change | T-test | Wilcoxon test | Summated rank | Serum |
|---|---|---|---|---|---|---|---|---|---|---|
| transducer of regulated cAMP response element-binding protein | TORC3 | mwghuman3 OK#A:04006 | NM_027769.1 | NP_073806.2 | 1.8 | 2.8 | 1.51E-05 | 1.73622E-05 | 1187.5 | |
| MYC-associated zinc finger protein | MAZ | mwghuman3 OK#A:04363 | NM_002383.1 | NP_002374.1 | 1.6 | 3.5 | 0.0000117 | 0.0000325 | 1195.5 | |
| thioredoxin reductase 1 | TXNRD1 | mwghuman3 OK#A:02930 | NM_182743.1 | NP_877420.1 | 2.4 | 16.9 | 0.0000377 | 0.0000254 | 1201 | |
| hypothetical protein xp_096895 | | mwghuman3 OK#B:5965 | XM_096895 | | 1.5 | 3.2 | 5.361E-08 | 2.51921E-06 | 1211.5 | |
| chromosome 22 open reading frame 4 | C22orf4 | mwghuman3 OK#B:9849 | NM_014346.1 | NP_055161.1 | 1.5 | 2.3 | 1.056E-05 | 1.33979E-05 | 1234 | |
| visinin-like 1 | VSNL1 | mwghuman3 OK#A:06227 | NM_003385.3 | NP_003376.2 | 2.2 | 13.8 | 0.0000215 | 0.0000254 | 1243.5 | |
| similar to Carboxypeptidase N 83 kDa chain | | mwghuman3 OK#B:4922 | XM_208550.5 | XP_209550.4 | 2.0 | 10.5 | 0.0000141 | 0.00000899 | 1256.5 | |
| KIAA1598 | KIAA1598 | mwghuman3 OK#A:10158 | NM_018330.3 | NP_060800.2 | 1.9 | 18.9 | 6.547E-05 | 8.56146E-07 | 1271 | |
| hypothetical protein flj13501 | | mwghuman3 OK#A:06319 | NM_025007 | | 2.0 | 5.7 | 3.162E-05 | 2.23862E-05 | 1285 | |
| DKFZP434O047 protein | DKFZP434O047 | mwghuman3 OK#A:08783 | NM_015594.1 | NP_056409.1 | 1.8 | 4.5 | 9.622E-08 | 4.13751E-05 | 1290.5 | |
| hypothetical protein FLJ38716 | | mwghuman3 OK#B:7389 | NM_152367.1 | NP_689580.1 | 1.9 | 4.0 | 9.5E-08 | 2.87228E-05 | 1291.5 | |
| similar to hypothetical protein (L1H 3 region) | | mwghuman3 OK#A:02711 | XM_372039.1 | XP_372039.2 | 1.9 | 3.5 | 3.977E-05 | 1.73622E-05 | 1295.5 | |
| hypothetical protein KIAA1875 | | mwghuman3 OK#B:5745 | XM_291269.3 | XP_281269.2 | 1.6 | 2.4 | 2.655E-05 | 1.33979E-05 | 1313.5 | |
| primase, polypeptide 1 | PRIM1 | mwghuman3 OK#A:07833 | NM_000946.2 | NP_000937.1 | 1.6 | 2.9 | 3.313E-05 | 5.24719E-05 | 1315 | |

| Gene Name | HUGO | MWG oligo # | NCBI mRNA ref seq | Protein ref seq | mean fold change | max fold change | T-test | Wilcoxon test | Summated rank | Serum |
|---|---|---|---|---|---|---|---|---|---|---|
| hypothetical protein BC001086 | | mwghuman3 0K#B:6914 | NM_138389.1 | NP_612398.1 | 1.7 | 3.3 | 0.0000359 | 0.0000367 | 1318.5 | |
| MCM2 minichromosome maintenance deficient 2 | MCM2 | mwghuman3 0K#A:08834 | NM_004526.2 | NP_004517.2 | 1.9 | 2.7 | 1.81E-06 | 0.0000045 | 1332 | |
| gap junction protein, alpha 3 | GJA3 | mwghuman3 0K#A:04569 | NM_021954.2 | NP_068773.2 | 1.8 | 2.7 | 1.04E-06 | 0.00000252 | 1332.5 | |
| chromosome 11 open reading frame 30 | C11orf30 | mwghuman3 0K#A:10832 | NM_020193.2 | NP_064578.2 | 1.4 | 3.4 | 6.848E-07 | 1.00418E-06 | 1339 | |
| similar to hypothetical protein FLJ30672 | | mwghuman3 0K#B:9577 | XM_376318.1 | XP_376318.1 | 1.8 | 2.3 | 3.03E-05 | 2.53726E-05 | 1349 | |
| Thy-1 co-transcribed (LOC94105) | THY1 | mwghuman3 0K#A:07498 | NM_033209.2 | NP_149886.1 | 1.5 | 3.4 | 1.262E-05 | 2.53726E-05 | 1353 | |
| low density lipoprotein receptor-related protein 3 | LRP3 | mwghuman3 0K#A:05068 | NM_002333.1 | NP_002324.1 | 1.5 | 2.1 | 1.066E-05 | 1.9727E-05 | 1358 | |
| LAG1 longevity assurance homolog 2 | LASS2 | mwghuman3 0K#A:00827 | NM_013384.3 | NP_037516.3 | 1.7 | 4.8 | 0.0000173 | 0.0000224 | 1365 | |
| chromosome 18 open reading frame 8 | C18orf8 | mwghuman3 0K#A:07371 | NM_013326.2 | NP_037458.2 | 1.5 | 2.1 | 6.11E-06 | 0.00000899 | 1366.5 | |
| zinc finger protein 81 | ZNF81 | mwghuman3 0K#B:1057 | NM_007137.1 | NP_009068.1 | 1.5 | 2.2 | 2.599E-06 | 1.8687E-06 | 1367.5 | |
| nuclear prelamin A recognition factor | NARF | mwghuman3 0K#A:02301 | NM_031968.1 | NP_114174.1 | 1.5 | 2.5 | 8.752E-06 | 1.73622E-05 | 1391.5 | |

| Gene Name | HUGO | MWG oligo # | NCBI mRNA ref seq | Protein ref seq | mean fold change | max fold change | T-test | Wilcoxon test | Summated rank | Serum |
|---|---|---|---|---|---|---|---|---|---|---|
| methylene tetrahydrofolate dehydrogenase (NAD+ dependent) | MTHFD2 | mwghuman3 OK#A:01688 | NM_006636.2 | NP_006627.1 | 2.4 | 8.4 | 0.0000661 | 0.00013 | 1392.5 | |
| dihydrolipoamide branched chain transacylase E2 | DBT | mwghuman3 OK#B:5854 | NM_001918.1 | NP_001909.1 | 1.6 | 2.3 | 4.015E-05 | 8.89315E-06 | 1398.5 | |
| sialyltransferase 7D | SIAT7D | mwghuman3 OK#A:03286 | NM_175040.1 | NP_778205.1 | 1.7 | 7.9 | 3.17E-06 | 0.00000598 | 1400 | |
| matrix metalloproteinase-like 1 | MMPL1 | mwghuman3 OK#A:02874 | NM_004142.1 | NP_004133.1 | 1.5 | 3.4 | 1.36E-06 | 2.91943E-06 | 1403 | |
| kallikrein 11 | KLK11 | mwghuman3 OK#A:09721 | NM_144947.1 | NP_659196.1 | 1.5 | 2.3 | 0.0000159 | 0.0000153 | 1415.5 | |
| karyopherin alpha 2 | KPNA2 | mwghuman3 OK#B:4036 | NM_002266.1 | NP_002257.1 | 1.6 | 3.3 | 9.792E-05 | 5.89923E-05 | 1426.5 | |
| FGFR1 oncogene partner 2 | FGFR1OP2 | mwghuman3 OK#B:2210 | NM_015833.1 | NP_056448.1 | 1.5 | 5.0 | 1.338E-05 | 1.33979E-05 | 1427.5 | |
| vimentin | VIM | mwghuman3 OK#A:02879 | NM_003380.1 | NP_003371.1 | 3.3 | 19.1 | 0.000123 | 0.0002 | 1451 | |
| FLJ44108 protein | | mwghuman3 OK#B:0931 | XM_379827.1 | XP_379827.1 | 1.7 | 2.9 | 7.746E-05 | 2.53726E-05 | 1474 | |
| poly(A) polymerase gamma | PAPOLG | mwghuman3 OK#A:03838 | NM_022894.2 | NP_075045.2 | 2.7 | 35.2 | 0.0000757 | 0.0000932 | 1474.5 | |
| formin homology 2 domain containing 1 | FHOD1 | mwghuman3 OK#A:05058 | NM_013241.1 | NP_037373.1 | 1.6 | 4.0 | 9.54E-06 | 0.00000187 | 1483.5 | |
| RAS-like, family 12 (RASL12) | RASL12 | mwghuman3 OK#A:07221 | NM_016563.2 | NP_057647.1 | 1.4 | 2.1 | 1.179E-05 | 2.23662E-05 | 1490.5 | |
| high-mobility group nucleosomal binding domain 2 | HMGN2 | mwghuman3 OK#B:9113 | NM_005517.2 | NP_005508.1 | 1.6 | 2.7 | 0.0000626 | 0.0000367 | 1495.5 | |

Fig. 11 (continued)

| Gene Name | HUGO | MWG oligo # | NCBI mRNA ref seq | Protein ref seq | mean fold change | max fold change | T-test | Wilcoxon test | Summated rank | Serum |
|---|---|---|---|---|---|---|---|---|---|---|
| phosphatidylinositol transfer protein, membrane-associated 2 | PITPNM2 | mwghuman3 OK#B:8484 | NM_020845 | NP_06589 | 2.3 | 26.2 | 0.0000711 | 0.0000224 | 1497 | |
| derlin-1 | DER1 | mwghuman3 OK#A:01654 | NM_024295.3 | NP_077271.1 | 1.5 | 3.3 | 4.883E-05 | 5.24719E-05 | 1527 | |
| EphA4 | EPHA4 | mwghuman3 OK#A:04433 | NM_004438.3 | NP_004429.1 | 1.5 | 3.1 | 0.0000113 | 0.0000743 | 1527.5 | |
| V-set and Immunoglobulin domain containing 1 | VSIG1 | mwghuman3 OK#B:6454 | NM_182607.3 | NP_872413.1 | 2.0 | 5.8 | 7.831E-05 | 3.24766E-05 | 1532.5 | |
| regulator of G-protein signalling 5 | RGS5 | mwghuman3 OK#B:0128 | NM_003617.2 | NP_003608.1 | 1.8 | 6.3 | 0.0000417 | 0.0000174 | 1534.5 | |
| KIAA1639 protein | | mwghuman3 OK#B:4938 | XM_290823.2 | XP_290923.3 | 1.9 | 11.5 | 2.878E-05 | 1.9727E-05 | 1540.5 | |
| SH2-B homolog | SH2B | mwghuman3 OK#B:8571 | NM_015503.1 | NP_056318.1 | 2.2 | 13.2 | 0.0000252 | 0.0000197 | 1556.5 | |
| peptidoglycan recognition protein 4 | PGLYRP4 | mwghuman3 OK#A:00868 | NM_020393.1 | NP_065128.1 | 1.5 | 3.2 | 2.891E-06 | 4.50136E-06 | 1566 | |
| CDC45 cell division cycle 45-like | CDC45L | mwghuman3 OK#A:09331 | NM_003504.3 | NP_003495.1 | 1.8 | 2.9 | 6.316E-05 | 0.000129985 | 1567.5 | |
| male sterility domain containing 1 | MLSTD1 | mwghuman3 OK#A:04500 | NM_018099.3 | NP_080589.3 | 1.9 | 10.0 | 6.279E-05 | 3.66781E-05 | 1585.5 | |
| hypothetical protein MGC11266 | | mwghuman3 OK#A:10595 | NM_024322.1 | NP_077298.1 | 1.5 | 3.4 | 5.16E-05 | 6.62502E-05 | 1608 | |
| tumor necrosis factor receptor superfamily, member 13B | TNFRSF13B | mwghuman3 OK#A:00922 | NM_012452.2 | NP_036584.1 | 1.7 | 3.8 | 2.737E-05 | 6.62502E-05 | 1643 | |

Fig. 11 (continued)

| Gene Name | HUGO | MWG oligo # | NCBI mRNA ref seq | Protein ref seq | mean fold change | max fold change | T-test | Wilcoxon test | Summated rank | Serum |
|---|---|---|---|---|---|---|---|---|---|---|
| neuroepithelial cell transforming gene 1 | NET1 | mwghuman3 OK#B:5122 | S82401.1 | AAB37883.1 | 1.4 | 2.1 | 8.878E-06 | 4.50138E-06 | 1857 | |
| lipoma HMGIC fusion partner-like 5 | LHFPL5 | mwghuman3 OK#C:9217 | NM_182548.2 | NP_872354.1 | 1.7 | 9.5 | 5.419E-05 | 4.66208E-05 | 1881 | |
| myxovirus (influenza virus) resistance 2 | MX2 | mwghuman3 OK#A:10348 | NM_002463.1 | NP_002454.1 | 1.6 | 9.3 | 0.0000739 | 0.000001 | 1880 | |
| sphingosine kinase 1 | SPHK1 | mwghuman3 OK#C:2284 | NM_182965.1 | NP_892010.1 | 1.5 | 2.2 | 2.284E-06 | 5.18452E-06 | 1702 | |
| ATP-binding cassette, sub-family G (WHITE), member 4 | ABCG4 | mwghuman3 OK#A:02044 | NM_022169.3 | NP_071452.2 | 1.7 | 8.3 | 0.000012 | 0.0000039 | 1702 | |
| serine (or cysteine) proteinase inhibitor, clade B (ovalbumin), member 2 | SERPINB2 | mwghuman3 OK#A:10076 | NM_002575.1 | NP_002566.1 | 1.8 | 8.3 | 3.09E-05 | 2.50475E-05 | 1705.5 | |
| UDP-N-acetyl-alpha-D-galactosamine:polypeptide N-acetylgalactosaminyltransferase 10 | GALNT10 | mwghuman3 OK#A:10048 | NM_017540.3 NM_0010036 80.1 | NP_060010.3 NP_0010036 80.1 | 1.6 | 7.1 | 6.432E-05 | 2.23862E-05 | 1711 | |
| leptin receptor | LEPR | mwghuman3 OK#B:5260 | | | 1.8 | 2.6 | 2.176E-05 | 2.87228E-05 | 1715.5 | |
| MAX dimerization protein 4 | MXD4 | mwghuman3 OK#A:08298 | NM_006454.2 | NP_006445.1 | 1.7 | 4.1 | 0.0000111 | 0.0000134 | 1719.5 | |
| phosphoinositol 4-phosphate adaptor protein-2 | FAPP2 | mwghuman3 OK#A:06804 | NM_032839.2 | NP_116028.1 | 1.5 | 3.3 | 1.563E-05 | 3.66781E-05 | 1725.5 | |
| nucleoporin 210 | NUP210 | mwghuman3 OK#B:7411 | NM_024923.2 | NP_079199.2 | 1.8 | 2.8 | 6.528E-05 | 0.000104282 | 1726.5 | |

Fig. 11 (continued)

| Gene Name | HUGO | MWG oligo # | NCBI mRNA ref seq | Protein ref seq | mean fold change | max fold change | T-test | Wilcoxon test | Summated rank | Serum |
|---|---|---|---|---|---|---|---|---|---|---|
| c-src tyrosine kinase | CSK | mwghuman3 OK#A-01623 | NM_004383.1 | NP_004374.1 | 1.5 | 5.1 | 7.283E-08 | 8.56149E-07 | 3601 | |
| neuropilin 1 | NRP1 | mwghuman3 OK#A-03091 | NM_003873.2 | NP_003864.2 | 2.3 | 17.2 | 0.002761 | 0.004728544 | 6356 | |

Fig. 11 (continued)

| Gene Name | HUGO | MWG oligo # | NCBI mRNA ref seq | Protein ref seq | mean fold change | max fold change | T-test | Wilcoxon test | Summated rank | Serum |
|---|---|---|---|---|---|---|---|---|---|---|
| neuritin 1 | NRN1 | mwghuman3 OK#A:00658 | NM_016588.2 | NP_057672.1 | 3.0 | 17.6 | 4.76E-07 | 0.000000421 | 63 | S |
| mannosyl (alpha-1,3-)-glycoprotein beta-1,2-N-acetylglucosaminyltransferase KIAA0100 gene product | MGAT1 | mwghuman3 OK#A:09187 | NM_002408.2 | NP_002397.1 | 1.7 | 4.1 | 3.51E-07 | 0.00000395 | 165.5 | S |
| | | mwghuman3 OK#A:10762 | NM_014880.2 | NP_055495.2 | 1.6 | 2.5 | 1.74E-08 | 0.000000085 | 241 | S |
| lipocalin 7 | LCN7 | mwghuman3 OK#B:9472 | NM_022164.1 | NP_071447.1 | 1.8 | 5.6 | 0.000015 | 0.0000271 | 436.5 | S |
| olfactomedin 1 | OLFM1 | mwghuman3 OK#B:3555 | NM_058199.2 | NP_478106.1 | 1.8 | 6.8 | 3.39E-06 | 0.00000178 | 455 | S |
| bone morphogenetic protein 7 | BMP7 | mwghuman3 OK#A:09863 | NM_001719.1 | NP_001710.1 | 1.7 | 4.1 | 2.86E-06 | 0.00000579 | 473 | S |
| midkine (neurite growth-promoting factor 2) | MDK | mwghuman3 OK#B:4650 | NM_002391.2 | NP_002382.1 | 1.8 | 4.8 | 4.98E-07 | 0.000000184 | 492.5 | S |
| a disintegrin-like and metalloprotease (reprolysin type) with thrombospondin type 1 motif, 10 | ADAMTS10 | mwghuman3 OK#B:1355 | NM_030957.1 | NP_112219.2 | 1.9 | 8.0 | 0.0000442 | 0.0000379 | 599.5 | S |
| pM5 protein | PM5 | mwghuman3 OK#A:00608 | NM_014287.2 | NP_055102.3 | 1.6 | 2.5 | 0.000017 | 0.0000339 | 598.5 | S |
| tissue inhibitor of metalloproteinase 1 | TIMP1 | mwghuman3 OK#A:08048 | NM_003254.1 | NP_003245.1 | 1.7 | 3.2 | 0.0000165 | 0.0000107 | 611.5 | S |
| lumican | LUM | mwghuman3 OK#A:09199 | NM_002345.2 | NP_002336.1 | 2.5 | 19.1 | 0.000104 | 0.0000883 | 632 | S |

Fig. 12

| Gene Name | HUGO | MWG oligo # | NCBI mRNA ref seq | Protein ref seq | mean fold change | max fold change | T-test | Wilcoxon test | Summated rank | Serum |
|---|---|---|---|---|---|---|---|---|---|---|
| EGF-like-domain, multiple 6 | EGFL6 | mwghuman3 OK#A:07688 | NM_015507.2 | NP_056322.2 | 1.9 | 4.2 | 0.0000747 | 0.0000243 | 712 | s |
| NODAL modulator 3 | NOMO3 | mwghuman3 OK#A:08071 | NM_173614.1 | NP_775885.1 | 1.5 | 3.0 | 1.71E-06 | 0.00000395 | 844.5 | s |
| insulin-like growth factor binding protein 5 | IGFBP5 | mwghuman3 OK#C:1077 | NM_000599.2 | NP_000590.1 | 2.3 | 15.0 | 0.0000791 | 0.000284 | 859.5 | s |
| hexosaminidase A (alpha polypeptide) | HEXA | mwghuman3 OK#B:9777 | NM_000520.2 | NP_000511.1 | 1.5 | 3.1 | 0.0000386 | 0.0000718 | 903.5 | s |
| serine (or cysteine) proteinase inhibitor, clade H (heat shock protein 47), member 1 | SERPINH1 | mwghuman3 OK#A:08615 | NM_001235.2 | NP_001226.2 | 1.5 | 3.2 | 0.0000043 | 0.0000107 | 1070.5 | s |
| carboxypeptidase A6 | CPA6 | mwghuman3 OK#A:02979 | NM_020361.2 | NP_085094.2 | 1.4 | 3.2 | 0.0000154 | 0.0000271 | 1098.5 | s |
| natriuretic peptide precursor C | NPPC | mwghuman3 OK#A:08602 | NM_024409.1 | NP_077720.1 | 1.5 | 3.1 | 8.17E-06 | 0.0000121 | 1134 | s |
| protease, serine, 11 | PRSS11 | mwghuman3 OK#B:1274 | NM_002775.2 | NP_002766.1 | 1.4 | 2.6 | 0.0000125 | 0.0000523 | 1151.5 | s |
| insulin-like growth factor binding protein 7 | IGFBP7 | mwghuman3 OK#A:03385 | NM_001553.1 | NP_001544.1 | 1.8 | 4.2 | 0.000239 | 0.000756 | 1222 | s |
| hypothetical protein FLJ23221 | | mwghuman3 OK#A:06273 | NM_024579.1 | NP_078855.1 | 1.5 | 2.8 | 0.0000598 | 0.000375 | 1277.5 | s |
| protein disulfide isomerase related protein | ERP70 | mwghuman3 OK#A:03979 | NM_004911.3 | NP_004902.1 | 1.5 | 3.9 | 0.000321 | 0.000215 | 1419 | s |

Fig. 12 (continued)

| Gene Name | HUGO | MWG oligo # | NCBI mRNA ref seq | Protein ref seq | mean fold change | max fold change | T-test | Wilcoxon test | Summated rank | Serum |
|---|---|---|---|---|---|---|---|---|---|---|
| UDP-N-acetyl-alpha-D-galactosamine:p olypeptide N-acetylgalactosam inyltransferase 14 (GalNAc-T14) | GALNT14 | mwghuman3 0K#B:4583 | BC010659.1 | AAH10659.1 | 1.4 | 2.4 | 0.000215 | 0.000312 | 1450.5 | s |
| inter-alpha (globulin) inhibitor H3 | ITIH3 | mwghuman3 0K#B:7988 | NM_002217.1 | NP_002208.2 | 1.5 | 3.0 | 0.000317 | 0.000972 | 1504 | s |
| pappalysin 2 | PAPPA2 | mwghuman3 0K#B:1638 | NM_020318.1 | NP_064714.1 | 1.5 | 2.8 | 0.000358 | 0.000584 | 1584 | s |
| lysyl oxidase-like 1 | LOXL1 | mwghuman3 0K#A:07055 | NM_005576.1 | NP_005567.1 | 1.8 | 5.5 | 0.0001 | 0.000259 | 1598.5 | s |
| secreted phosphoprotein 1 | SPP1 | mwghuman3 0K#A:09441 | NM_000582.2 | NP_000573.1 | 2.7 | 139.1 | 0.000577 | 0.00185 | 1789 | s |
| tumor necrosis factor receptor superfamily, member 6b, decoy | TNFRSF6B | mwghuman3 0K#A:05069 | NM_032945.2 | NP_116563.1 | 2.0 | 6.8 | 0.001594 | 0.001244 | 1901.5 | s |
| secreted protein, acidic, cysteine-rich (osteonectin) | SPARC | mwghuman3 0K#A:08092 | NM_003118.2 | NP_003109.1 | 1.7 | 4.5 | 0.000359 | 0.000895 | 2512 | s |
| sulfatase 1 | SULF1 | mwghuman3 0K#B:8770 | NM_015170.1 | NP_055985.1 | 2.5 | 67.3 | 0.007144 | 0.000895 | 2581 | s |
| microseminoprot ein, beta | MSMB | mwghuman3 0K#B:4000 | NM_002443.2 | NP_002434.1 | 1.6 | 11.8 | 0.00535 | 0.042817 | 6739.5 | s |
| tolloid-like 2 | TLL2 | mwghuman3 0K#A:02932 | NM_012465.2 | NP_036597.1 | 1.9 | 29.2 | 0.036032 | 0.070205 | 8875.5 | s |
| semaphorin sem2 (LOC56920) | SEM2 | mwghuman3 0K#A:05073 | NM_020163.1 | NP_064548.1 | 1.2 | 1.8 | 0.0172289 | 0.01761606 | 10677 | s |

Fig. 12 (continued)

| Gene Name | HUGO | MWG oligo # | NCBI mRNA ref seq | Protein ref seq | mean fold change | max fold change | T-test | Wilcoxon test | Summated rank | Serum |
|---|---|---|---|---|---|---|---|---|---|---|
| sema domain, immunoglobulin domain (Ig), short basic domain, secreted, (semaphorin) 3F | SEMA3F | mwghuman3 0K#A:07262 | NM_004188.2 | NP_004177.2 | 1.7 | 19.5 | 0.2804993 | 0.3890127 | 23888.5 | s |
| endoglin | ENG | mwghuman3 0K#A:05668 | NM_000118.1 | NP_000109.1 | 1.8 | 3.7 | 2.76E-10 | 1.75E-09 | 37 | |
| claudin 6 | CLDN6 | mwghuman3 0K#A:08357 | NM_021195.3 | NP_067018.1 | 2.2 | 6.7 | 1.84E-07 | 0.000000881 | 59 | |
| prothymosin, alpha (gene sequence 28) | PTMA | mwghuman3 0K#B:B039 | NM_002823.2 | NP_002814.2 | 1.9 | 6.0 | 1.17E-07 | 0.00000031 | 77.5 | |
| nipsnap homolog 1 | NIPSNAP1 | mwghuman3 0K#A:08899 | NM_003634.1 | NP_003625.1 | 2.0 | 4.0 | 3.08E-07 | 0.000000362 | 92.5 | |
| arginine vasopressin receptor 2 (nephrogenic diabetes insipidus) | AVPR2 | mwghuman3 0K#A:01219 | NM_000054.2 | NP_000045.1 | 1.7 | 3.7 | 1.2E-07 | 0.000000227 | 98 | |
| malignant fibrous histiocytoma amplified sequence 1 | MFHAS1 | mwghuman3 0K#A:04639 | NM_004225.1 | NP_004216.1 | 2.2 | 9.3 | 1.68E-09 | 2.62E-08 | 120 | |
| homeo box A13 | HOXA13 | mwghuman3 0K#A:08971 | NM_000522.2 | NP_000513.2 | 1.9 | 6.4 | 7.15E-07 | 0.000000421 | 122 | |
| myxovirus (influenza virus) resistance 2 | MX2 | mwghuman3 0K#A:10346 | NM_002463.1 | NP_002454.1 | 1.8 | 6.6 | 1.42E-06 | 0.000000659 | 156.5 | |

Fig. 12 (continued)

| Gene Name | HUGO | MWG oligo # | NCBI mRNA ref.seq | Protein ref seq | mean fold change | max fold change | T-test | Wilcoxon test | Summated rank | Serum |
|---|---|---|---|---|---|---|---|---|---|---|
| similar to sodium- and chloride-dependent creatine transporter | | mwghuman3 0K#C:4285 | NM_198857.1 | NP_942154.1 | 1.8 | 4.1 | 1.78E-06 | 0.0000051 | 164 | |
| transmembrane protein 19 | TMEM19 | mwghuman3 0K#B:7083 | NM_018279.2 | NP_060749.2 | 1.8 | 3.0 | 3.14E-06 | 0.00000204 | 175 | |
| prostaglandin I2 (prostacyclin) receptor (IP) | PTGIR | mwghuman3 0K#A:00288 | NM_000960.3 | NP_000951.1 | 2.1 | 9.9 | 4.88E-06 | 0.00000449 | 205 | |
| hypothetical protein xp_047287 | | mwghuman3 0K#B:6855 | XM_047287 | | 1.6 | 3.9 | 2.89E-07 | 0.000000881 | 235 | |
| hypothetical protein flj11871 | | mwghuman3 0K#A:10682 | NM_025117 | | 1.6 | 3.3 | 6.94E-07 | 0.00000102 | 240.5 | |
| proline synthetase co-transcribed homolog | PROSC | mwghuman3 0K#B:0341 | NM_007198.2 | NP_009129.1 | 1.7 | 3.8 | 3.41E-07 | 0.00000233 | 270 | |
| G protein-coupled receptor 32 | GPR32 | mwghuman3 0K#A:03297 | NM_001506.1 | NP_001497.1 | 2.4 | 21.8 | 0.0000154 | 0.0000216 | 322 | |
| hypothetical protein MGC34923 | | mwghuman3 0K#C:4473 | NM_144717.2 | NP_653318.2 | 1.5 | 2.7 | 0.0000015 | 0.00000117 | 323 | |
| MGC27121 gene | | mwghuman3 0K#C:3953 | NM_001001343.1 | NP_001001043.1 | 2.8 | 10.4 | 0.0000214 | 0.0000243 | 333 | |
| NAD(P)H dehydrogenase, quinone 1 | NQO1 | mwghuman3 0K#A:05176 | NM_000903.1 | NP_000894.1 | 2.6 | 17.7 | 7.17E-08 | 0.0000422 | 352.5 | |
| cytoskeleton-associated protein 4 | CKAP4 | mwghuman3 0K#A:01860 | NM_006825.2 | NP_006816.2 | 1.8 | 4.9 | 0.0000029 | 0.00000233 | 382 | |
| sialyltransferase 7D | SIAT7D | mwghuman3 0K#A:03288 | NM_175040.1 | NP_778205.1 | 1.6 | 2.6 | 4.14E-09 | 8.34E-09 | 394 | |

Fig. 12 (continued)

| Gene Name | HUGO | MWG oligo # | NCBI mRNA ref seq | Protein ref seq | mean fold change | max fold change | T-test | Wilcoxon test | Summated rank | Serum |
|---|---|---|---|---|---|---|---|---|---|---|
| hypothetical protein BCD01096 | | mwghuman3 OK#B:8914 | NM_138389.1 | NP_612398.1 | 1.6 | 3.6 | 1.99E-07 | 0.000000421 | 394 | |
| 3-phosphoinositide dependent protein kinase-1 | PDPK1 | mwghuman3 OK#A:10300 | NM_002613.2 | NP_002604.1 | 1.5 | 2.1 | 0.0000192 | 0.00000135 | 438 | |
| phosphatidylinositol transfer protein, membrane-associated 2 | PITPNM2 | mwghuman3 OK#B:8484 | AB040890.2 | BAA95981.2 | 2.1 | 7.8 | 0.0000309 | 0.00000579 | 448 | |
| regulator of mitotic spindle assembly 1 | | mwghuman3 OK#A:09972 | XM_040863 | | 2.0 | 11.1 | 0.0000219 | 0.0000271 | 449.5 | |
| molecule interacting with Rab13 | MIRAB13 | mwghuman3 OK#C:0021 | NM_033386.1 | NP_203744.1 | 1.5 | 3.0 | 2.16E-06 | 0.0000084 | 457.5 | |
| protease, serine, 15 | PRSS15 | mwghuman3 OK#A:03363 | NM_004793.2 | NP_004784.2 | 1.5 | 2.7 | 0.0000101 | 0.0000135 | 497 | |
| porcupine homolog | PORCN | mwghuman3 OK#A:00520 | NM_203476.1 | NP_982302.1 | 1.6 | 3.4 | 7.61E-06 | 0.0000243 | 528 | |
| likely ortholog of mouse limb-bud and heart gene | LBH | mwghuman3 OK#B:7280 | NM_030915.1 | NP_112177.1 | 1.6 | 3.8 | 3.35E-07 | 0.000000268 | 534.5 | |
| sine oculis homeobox homolog 6 | SIX6 | mwghuman3 OK#A:10145 | NM_007374.1 | NP_031400.1 | 1.5 | 2.4 | 0.0000131 | 0.00000949 | 538 | |
| gap junction protein, beta 2A | GJB2 | mwghuman3 OK#A:09852 | NM_004004.3 | NP_003995.2 | 1.8 | 4.1 | 0.0000184 | 0.0000977 | 541.5 | |
| FLJ35784 protein | | mwghuman3 OK#C:4803 | NM_198534.1 | NP_940938.1 | 2.0 | 5.2 | 0.0000285 | 0.0000304 | 563.5 | |
| cell division cycle 2 | CDC2 | mwghuman3 OK#A:05382 | NM_033379.2 | NP_203698.1 | 2.4 | 7.8 | 0.0000208 | 0.000284 | 582.5 | |

Fig. 12 (continued)

| Gene Name | HUGO | MWG oligo # | NCBI mRNA ref seq | Protein ref seq | mean fold change | max fold change | T-test | Wilcoxon test | Summated rank | Serum |
|---|---|---|---|---|---|---|---|---|---|---|
| solute carrier family 37 (glycerol-3-phosphate transporter), member 3 | SLC37A3 | mwghuman3 OK#B:8722 | NM_207113.1 | NP_996996.1 | 1.5 | 3.8 | 7.99E-07 | 0.00000117 | 596 | |
| sprouty homolog 4 | SPRY4 | mwghuman3 OK#C:0553 | NM_030964.2 | NP_112228.2 | 1.5 | 3.1 | 3.13E-06 | 0.0000084 | 597.5 | |
| LIM homeobox 3 | LHX3 | mwghuman3 OK#A:025580 | NM_178138.2 | NP_835258.1 | 1.4 | 2.2 | 1.73E-06 | 0.00000049 | 608.5 | |
| chromosome 7 open reading frame 27 | C7orf27 | mwghuman3 OK#B:2531 | NM_152743.1 | NP_689956.1 | 1.6 | 3.2 | 2.33E-06 | 0.00000102 | 648.5 | |
| LDL receptor adaptor protein | ARH | mwghuman3 OK#B:2491 | NM_015627.1 | NP_058442.1 | 1.5 | 3.1 | 0.0000141 | 0.0000216 | 649 | |
| solute carrier family 39 (zinc transporter), member 1 | SLC39A1 | mwghuman3 OK#A:02443 | NM_014437.3 | NP_055252.2 | 1.6 | 3.7 | 0.0000296 | 0.0000498 | 652 | |
| zinc finger protein 307 (ZNF307) | ZNF307 | mwghuman3 OK#A:08705 | NM_018110.3 | NP_081983.2 | 1.5 | 3.8 | 5.01E-06 | 0.00000743 | 658 | |
| macrophage migration Inhibitory factor | MIF | mwghuman3 OK#A:09347 | NM_002415.1 | NP_002406.1 | 1.6 | 3.6 | 0.0000719 | 0.0000977 | 681.5 | |
| synuclein, alpha interacting protein | SNCAIP | mwghuman3 OK#B:08103 | NM_005460.1 | NP_005451.1 | 1.6 | 2.7 | 0.00000188 | 0.00000301 | 683 | |
| bone marrow stromal cell antigen 2 | BST2 | mwghuman3 OK#B:4758 | NM_004335.2 | NP_004326.1 | 2.1 | 5.3 | 0.0000818 | 0.000236 | 737.5 | |
| proline-serine-threonine phosphatase interacting protein 1 | PSTPIP1 | mwghuman3 OK#B:0578 | NM_003978.2 | NP_003969.2 | 1.6 | 3.3 | 2.22E-06 | 0.00000347 | 765 | |

Fig. 12 (continued)

| Gene Name | HUGO | MWG oligo # | NCBI mRNA ref seq | Protein ref seq | mean fold change | max fold change | T-test | Wilcoxon test | Summated rank | Serum |
|---|---|---|---|---|---|---|---|---|---|---|
| topoisomerase (DNA) II alpha | TOP2A | mwghuman3 0K#B:7144 | NM_001067.2 | NP_001058.2 | 2.0 | 5.5 | 0.0000799 | 0.000161 | 760.5 | |
| MCM2 minichromosome maintenance deficient 2 | MCM2 | mwghuman3 0K#A:08634 | NM_004526.2 | NP_004517.2 | 1.5 | 2.3 | 4.21E-08 | 0.00000395 | 774.5 | |
| SRY (sex determining region Y)-box 4 | SOX4 | mwghuman3 0K#A:07410 | NM_003107.2 | NP_003098.1 | 1.5 | 4.8 | 4.96E-08 | 0.00000448 | 789 | |
| nuclear receptor coactivator 5 | NCOA5 | mwghuman3 0K#B:8592 | NM_020867.1 | NP_066018.1 | 1.6 | 2.8 | 0.0000122 | 0.00000223 | 792 | |
| tubulin, alpha 4 | TUBA4 | mwghuman3 0K#B:2461 | NM_025019.1 | NP_079295.1 | 1.9 | 5.1 | 0.0000645 | 0.000161 | 793.5 | |
| hypothetical protein FLJ31436 | | mwghuman3 0K#C:8001 | NM_152385.1 | NP_689598.1 | 1.5 | 2.9 | 0.0000327 | 0.0000121 | 804 | |
| odd-skipped homolog | ODD | mwghuman3 0K#C:8737 | NM_145260.1 | NP_660303.1 | 1.8 | 5.9 | 0.000131 | 0.0000523 | 813 | |
| solute carrier family 23 (nucleobase transporters), member 2 | SLC23A2 | mwghuman3 0K#A:04621 | NM_203327.1 | NP_976072.1 | 1.6 | 4.7 | 0.0000089 | 0.000132 | 819.5 | |
| split handfoot malformation (ectrodactyly) type 1 | SHFM1 | mwghuman3 0K#A:05869 | NM_006304.1 | NP_006295.1 | 1.6 | 3.3 | 0.0000306 | 0.0000647 | 823.5 | |
| SFRS protein kinase 2 | SRPK2 | mwghuman3 0K#A:08608 | NM_182692.1 | NP_872634.1 | 1.8 | 6.4 | 0.0000197 | 0.0000339 | 848.5 | |
| chromosome 18 open reading frame 8 | C18orf8 | mwghuman3 0K#A:07371 | NM_013326.2 | NP_037458.2 | 1.4 | 2.1 | 1.54E-08 | 0.00000347 | 856 | |
| formin homology 2 domain containing 1 | FHOD1 | mwghuman3 0K#A:05058 | NM_013241.1 | NP_037373.1 | 1.5 | 2.3 | 0.0000106 | 0.00000153 | 863.5 | |

Fig. 12 (continued)

| Gene Name | HUGO | MWG oligo # | NCBI mRNA ref seq | Protein ref seq | mean fold change | max fold change | T-test | Wilcoxon test | Summated rank | Serum |
|---|---|---|---|---|---|---|---|---|---|---|
| receptor (calcitonin) activity modifying protein 2 | RAMP2 | mwghuman3 OK#A:02505 | NM_005854.1 | NP_005845.1 | 1.6 | 4.2 | 0.0000208 | 0.0000172 | 866.5 | |
| 2,3-bisphosphoglycerate mutase | BPGM | mwghuman3 OK#A:00673 | NM_001724.3 | NP_001715.1 | 1.6 | 4.1 | 0.000203 | 0.0000523 | 868 | |
| SH2-B homolog | SH2B | mwghuman3 OK#B:8571 | NM_015503.1 | NP_056318.1 | 1.7 | 5.7 | 0.0000461 | 0.0000647 | 906 | |
| regulator of G-protein signalling 5 | RGS5 | mwghuman3 OK#B:0128 | NM_003617.2 | NP_003608.1 | 1.8 | 12.8 | 0.0000299 | 0.000177 | 922.5 | |
| phosphoinositol 4-phosphate adaptor protein-2 | FAPP2 | mwghuman3 OK#A:0B904 | NM_032639.2 | NP_116028.1 | 1.4 | 2.3 | 0.0000188 | 0.0000647 | 932.5 | |
| coxsackie virus and adenovirus receptor | CXADR | mwghuman3 OK#A:00118 | NM_001338.3 | NP_001329.1 | 1.9 | 4.7 | 0.000165 | 0.000177 | 935.5 | |
| Meis1, myeloid ecotropic viral integration site 1 homolog 2 | MEIS2 | mwghuman3 OK#A:08006 | NM_002399.2 | NP_002390.1 | 1.5 | 2.8 | 0.0000768 | 0.0000863 | 941 | |
| tensin-like SH2 domain containing 1 | TENS1 | mwghuman3 OK#A:01929 | NM_022748.6 | NP_0735856 | 1.5 | 3.1 | 0.0000868 | 0.000132 | 946.5 | |
| small homolog 2 | SNAI2 | mwghuman3 OK#A:10655 | NM_003068.3 | NP_003059.1 | 1.8 | 17.9 | 0.0000524 | 0.0000339 | 960.5 | |
| docking protein 3 | DOK3 | mwghuman3 OK#B:2635 | NM_024872.1 | NP_079148.1 | 1.6 | 4.8 | 7.57E-06 | 0.00000049 | 967.5 | |
| carbohydrate (N-acetylglucosamine-6-O) sulfotransferase 2 | CHST2 | mwghuman3 OK#A:06174 | NM_004267.2 | NP_004258.2 | 1.7 | 5.2 | 9.87E-07 | 0.00000155 | 983 | |
| nucleoside phosphorylase | NP | mwghuman3 OK#A:03762 | NM_000270.1 | NP_000261.1 | 1.5 | 4.1 | 0.0000189 | 0.0000271 | 996.5 | |

Fig. 12 (continued)

| Gene Name | HUGO | MWG oligo # | NCBI mRNA ref seq | Protein ref seq | mean fold change | max fold change | T-test | Wilcoxon test | Summated rank | Serum |
|---|---|---|---|---|---|---|---|---|---|---|
| visinin-like 1 | VSNL1 | mwghuman3 OK#A:05227 | NM_003385.3 | NP_003376.2 | 1.7 | 3.5 | 0.0000811 | 0.00012 | 1013 | |
| v-yes-1 Yamaguchi sarcoma viral related oncogene homolog | LYN | mwghuman3 OK#C-2653 | NM_002350.1 | NP_002341.1 | 1.6 | 3.5 | 0.0000593 | 0.000108 | 1013.5 | |
| hepatocellular carcinoma-associated antigen 127 | HCA127 | mwghuman3 OK#B:7758 | NM_018684.1 | NP_061154.1 | 1.3 | 2.0 | 0.0000442 | 0.0000797 | 1017 | |
| solute carrier family 22 (organic cation transporter), member 2 | SLC22A2 | mwghuman3 OK#A:02704 | NM_153191.1 | NP_694861.1 | 2.3 | 12.5 | 0.000298 | 0.000535 | 1021 | |
| MAX dimerization protein 4 | MXD4 | mwghuman3 OK#A:08296 | NM_006454.2 | NP_006445.1 | 1.4 | 2.5 | 5.21E-06 | 0.00000656 | 1025 | |
| Thy-1 co-transcribed (LOC94105) | | mwghuman3 OK#A:07488 | NM_033209.2 | NP_149986.1 | 1.4 | 2.0 | 0.0000307 | 0.0000153 | 1032.5 | |
| Thy-1 co-transcribed (LOC94105) | THY1 | mwghuman3 OK#A:07488 | NM_033209.2 | NP_149986.1 | 1.4 | 2.0 | 3.072E-05 | 1.52973E-05 | 1032.5 | |
| leucine rich repeat and fibronectin type III domain containing 3 | LRFN3 | mwghuman3 OK#A:00147 | NM_024509.1 | NP_078785.1 | 1.6 | 2.4 | 0.000225 | 0.0000419 | 1035.5 | |
| h4 histone family, member g | | mwghuman3 OK#A:01329 | XM_030144 | | 1.9 | 12.3 | 0.000241 | 0.0000883 | 1040 | |
| hypothetical protein FLJ23390 | | mwghuman3 OK#A:05789 | NM_022746.2 | NP_073583.2 | 1.5 | 2.4 | 0.0000373 | 0.0000172 | 1045.5 | |

Fig. 12 (continued)

| Gene Name | HUGO | MWG oligo # | NCBI mRNA ref seq | Protein ref seq | mean fold change | max fold change | T-test | Wilcoxon test | Summated rank | Serum |
|---|---|---|---|---|---|---|---|---|---|---|
| tribbles homolog 2 | TRIB2 | mwghuman3 0K#A:05272 | NM_021643.1 | NP_067675.1 | 1.7 | 4.1 | 0.0000616 | 0.000195 | 1058 | |
| keratin, hair, acidic, 3B | KRTHA3B | mwghuman3 0K#A:02682 | NM_002279.3 | NP_002270.1 | 1.3 | 2.1 | 0.0000079 | 0.0000271 | 1071.5 | |
| kinesin family member 21A | KIF21A | mwghuman3 0K#C:0043 | NM_017641.2 | NP_060111.2 | 1.7 | 3.1 | 0.000121 | 0.000108 | 1073 | |
| high-mobility group nucleosomal binding domain 2 | HMGN2 | mwghuman3 0K#B:9113 | NM_005517.2 | NP_005508.1 | 1.5 | 2.9 | 0.000199 | 0.0000883 | 1075 | |
| ankyrin repeat domain 17 | ANKRD17 | mwghuman3 0K#B:0250 | NM_198889.1 | NP_942592.1 | 1.5 | 2.6 | 0.000013 | 0.00000743 | 1089.5 | |
| recombination activating gene 1 | RAG1 | mwghuman3 0K#A:09856 | NM_000448.1 | NP_000439.1 | 1.4 | 2.7 | 0.000114 | 0.0000797 | 1090 | |
| nucleotide binding protein 2 | NUBP2 | mwghuman3 0K#C:1908 | NM_012225.1 | NP_036357.1 | 1.4 | 2.3 | 0.0000198 | 0.0000193 | 1097 | |
| hypothetical protein FLJ20489 | | mwghuman3 0K#A:07462 | NM_017842.1 | NP_060312.1 | 1.4 | 2.7 | 3.49E-06 | 0.000000395 | 1100.5 | |
| calcium/calmodulin-dependent serine protein kinase (MAGUK family) | CASK | mwghuman3 0K#A:01768 | NM_003688.1 | NP_003679.1 | 1.5 | 3.5 | 0.0000572 | 0.000161 | 1104.5 | |
| huntingtin interacting protein 1 | HIP1 | mwghuman3 0K#A:05908 | NM_005338.4 | NP_005329.3 | 1.4 | 4.5 | 0.0000185 | 0.00000656 | 1110 | |
| LAG1 longevity assurance homolog 2 | LASS2 | mwghuman3 0K#A:00827 | NM_013384.3 | NP_037516.3 | 1.5 | 2.3 | 0.0000311 | 0.000083 | 1111.5 | |
| protein kinase C, delta binding protein | PRKCDBP | mwghuman3 0K#B:4639 | NM_145040.2 | NP_659477.2 | 1.6 | 3.5 | 6.96E-07 | 0.000000194 | 1123.5 | |

Fig. 12 (continued)

| Gene Name | HUGO | MWG oligo # | NCBI mRNA ref seq | Protein ref seq | mean fold change | max fold change | T-test | Wilcoxon test | Summated rank | Serum |
|---|---|---|---|---|---|---|---|---|---|---|
| tyrosine kinase with Immunoglobulin and epidermal growth factor homology domains | TIE | mwghuman3 0K#A:05888 | NM_005424.2 | NP_005415.1 | 1.7 | 4.3 | 0.000268 | 0.000312 | 1128.5 | |
| chromosome 5 open reading frame 15 | C5orf15 | mwghuman3 0K#A:10834 | NM_020199.1 | NP_064584.1 | 1.8 | 3.3 | 0.000144 | 0.000195 | 1131 | |
| anillin, actin binding protein | ANLN | mwghuman3 0K#A:05280 | NM_018685.2 | NP_061155.2 | 2.2 | 6.5 | 0.000908 | 0.000332 | 1154 | |
| derlin-1 | DER1 | mwghuman3 0K#A:01854 | NM_024295.3 | NP_077271.1 | 1.4 | 3.1 | 0.000115 | 0.0000422 | 1160.5 | |
| CGI-72 protein | CGI-72 | mwghuman3 0K#C:2137 | NM_018018.3 | NP_057102.3 | 1.4 | 2.5 | 0.0000047 | 0.000195 | 1165 | |
| activin A receptor type II-like 1 | ACVRL1 | mwghuman3 0K#A:00470 | NM_000020.1 | NP_000011.1 | 1.4 | 2.3 | 0.000113 | 0.0000618 | 1178 | |
| ectonucleoside triphosphate diphosphohydrolase 8 | ENTPD8 | mwghuman3 0K#C:1422 | NM_138793.2 | NP_620148.1 | 1.4 | 2.2 | 0.0000121 | 0.0000379 | 1179.5 | |
| SH3 domain binding glutamic acid-rich protein like 3 | SH3BGRL3 | mwghuman3 0K#B:1593 | NM_031286.2 | NP_112576.1 | 1.5 | 2.5 | 0.000062 | 0.000177 | 1185.5 | |
| SMC4 structural maintenance of chromosomes 4-like 1 (yeast) | SMC4L1 | mwghuman3 0K#A:05648 | NM_001002799.1 | NP_001002799.1 | 1.7 | 3.4 | 0.000271 | 0.000215 | 1190 | |
| NADH:ubiquinone oxidoreductase MLRQ subunit homolog | | mwghuman3 0K#B:1359 | NM_020142.3 | NP_064527.1 | 2.2 | 17.8 | 0.000123 | 0.000249 | 1198 | |
| angiogenic factor VG5Q | VG5Q | mwghuman3 0K#B:2180 | NM_018046.3 | NP_060516.2 | 1.4 | 2.8 | 0.0000245 | 0.0000562 | 1228.5 | |

Fig. 12 (continued)

| Gene Name | HUGO | MWG oligo # | NCBI mRNA ref seq | Protein ref seq | mean fold change | max fold change | T-test | Wilcoxon test | Summated rank | Serum |
|---|---|---|---|---|---|---|---|---|---|---|
| stathmin 1 | STMN1 | mwghuman3 OK#A:00925 | NM_203401.1 | NP_981946.1 | 1.9 | 11.8 | 0.0004 | 0.000342 | 1250 | |
| lipidosin | BG1 | mwghuman3 OK#A:08285 | NM_015182.3 | NP_055977.3 | 1.6 | 8.8 | 0.000221 | 0.00017 | 1267 | |
| BCL2-like 11 | BCL2L11 | mwghuman3 OK#A:08369 | NM_207003.1 | NP_998886.1 | 1.4 | 2.5 | 0.0000369 | 0.000108 | 1271 | |
| AMP-activated protein kinase family member 5 | ARK5 | mwghuman3 OK#B:9070 | NM_014840.2 | NP_055655.1 | 1.5 | 3.1 | 0.000345 | 0.0000647 | 1273.5 | |
| pleckstrin homology domain containing, family A (phosphoinositid e binding specific) member 4 | PLEKHA4 | mwghuman3 OK#B:3447 | NM_020904.1 | NP_065955.1 | 1.4 | 2.6 | 6.89E-06 | 0.0000107 | 1278.5 | |
| kallikrein 11 | KLK11 | mwghuman3 OK#A:09721 | NM_144947.1 | NP_659198.1 | 1.4 | 3.3 | 0.00024 | 0.000047 | 1332 | |
| suppression of tumorigenicity 7 like | ST7L | mwghuman3 OK#A:01391 | NM_138726.2 | NP_620056.1 | 1.5 | 3.3 | 0.0001161 | 0.000132 | 1376.5 | |
| transducin-like enhancer of split 3 | TLE3 | mwghuman3 OK#A:08092 | NM_005078.1 | NP_005069.1 | 1.3 | 2.1 | 0.0000102 | 0.0000084 | 1382.5 | |
| Inter-alpha (globulin) inhibitor H5 | ITIH5 | mwghuman3 OK#A:10153 | NM_032817.2 | NP_116206.2 | 1.4 | 2.4 | 0.000205 | 0.000259 | 1387.5 | |
| regulator of G-protein signalling 11 | RGS11 | mwghuman3 OK#A:09250 | NM_183337.1 | NP_899180.1 | 1.5 | 2.8 | 0.0000268 | 0.0000379 | 1400.5 | |
| ankyrin repeat and SOCS box-containing 9 | ASB9 | mwghuman3 OK#A:01131 | NM_024087.1 | NP_076992.1 | 1.4 | 2.5 | 0.000131 | 0.000146 | 1418.5 | |

Fig. 12 (continued)

| Gene Name | HUGO | MWG oligo # | NCBI mRNA ref seq | Protein ref seq | mean fold change | max fold change | T-test | Wilcoxon test | Summated rank | Serum |
|---|---|---|---|---|---|---|---|---|---|---|
| chromosome 6 open reading frame 69 | C6orf69 | mwghuman3 OK#C:0854 | NM_173562.3 | NP_775833.2 | 1.4 | 2.7 | 0.0000737 | 0.000195 | 1436 | |
| transmembrane 7 superfamily member 3 | TM7SF3 | mwghuman3 OK#A:09485 | NM_016551.1 | NP_057635.1 | 1.6 | 3.0 | 0.000278 | 0.000535 | 1437 | |
| secernin 3 | SCRN3 | mwghuman3 OK#A:00384 | NM_024583.2 | NP_078859.2 | 1.4 | 2.7 | 0.0000977 | 0.000215 | 1452 | |
| cryptochrome 1 | CRY1 | mwghuman3 OK#A:06219 | NM_004075.2 | NP_004066.1 | 1.5 | 3.7 | 0.000377 | 0.000259 | 1457.5 | |
| plexin A1 | PLXNA1 | mwghuman3 OK#B:8739 | NM_032242.2 | NP_115618.2 | 1.4 | 3.2 | 0.000107 | 0.000108 | 1474 | |
| UDP-N-acetyl-alpha-D-galactosamine:polypeptide N-acetylgalactosaminyltransferase 10 (GalNAc-T10) | GALNT10 | mwghuman3 OK#B:5489 | NM_017540.3 | NP_060010.3 | 1.4 | 2.0 | 4.42E-08 | 0.000000659 | 1479.5 | |
| gap junction protein, alpha 4 | GJA4 | mwghuman3 OK#A:07540 | NM_002060.1 | NP_002051.1 | 1.4 | 2.8 | 0.000427 | 0.000284 | 1488.5 | |
| hypothetical protein DKFZp434G1415 | | mwghuman3 OK#C:3525 | NM_031292.2 | NP_112582.2 | 1.4 | 2.9 | 0.0000627 | 0.000156 | 1501 | |
| WD repeat and SOCS box-containing 2A | WSB2 | mwghuman3 OK#B:1353 | NM_018639.3 | NP_061109.1 | 1.4 | 2.5 | 0.0000652 | 0.0000523 | 1505 | |
| cytidine deaminase | CDA | mwghuman3 OK#A:07490 | NM_001785.1 | NP_001776.1 | 1.6 | 3.0 | 0.0000477 | 0.0000271 | 1538.5 | |
| phosphoribosylglycinamide formyltransferase | GART | mwghuman3 OK#A:10142 | NM_000819.3 | NP_000810.1 | 1.4 | 2.2 | 0.0000428 | 0.000146 | 1560 | |
| histone 1, H1b | HIST1H1B | mwghuman3 OK#A:05716 | NM_005322.2 | NP_005313.1 | 1.5 | 4.0 | 0.0000929 | 0.000238 | 1578.5 | |

Fig. 12 (continued)

| Gene Name | HUGO | MWG oligo # | NCBI mRNA ref seq | Protein ref seq | mean fold change | max fold change | T-test | Wilcoxon test | Summated rank | Serum |
|---|---|---|---|---|---|---|---|---|---|---|
| zinc metalloproteinase (STE24 homolog, yeast) | ZMPSTE24 | mwghuman3 0K#A:09568 | NM_005857.2 | NP_005848.2 | 1.5 | 3.9 | 0.000166 | 0.000236 | 1653.5 | |
| transmembrane protein 33 | TMEM33 | mwghuman3 0K#A:01542 | NM_018126.1 | NP_060596.1 | 2.9 | 31.9 | 0.000365 | 0.002513 | 1669.5 | |
| glucose phosphate isomerase | GPI | mwghuman3 0K#B:1465 | NM_000175.2 | NP_000166.2 | 1.4 | 2.6 | 0.000153 | 0.000236 | 1670.5 | |
| hypothetical protein FLJ11000 | | mwghuman3 0K#B:4538 | NM_018296.1 | NP_060765 | 1.6 | 5.1 | 0.000203 | 0.000448 | 1687.5 | |
| hypothetical protein MGC55576 | | mwghuman3 0K#A:06786 | NM_024056.2 | NP_076961.1 | 1.6 | 11.7 | 0.000735 | 0.000312 | 1710 | |
| calcium/calmodulin-dependent protein kinase ID | CAMK1D | mwghuman3 0K#A:03327 | NM_020397.1 | NP_065130.1 | 1.4 | 2.6 | 0.00034 | 0.000423 | 1719 | |
| protein tyrosine phosphatase, non-receptor type 21 | PTPN21 | mwghuman3 0K#A:09269 | NM_007039.2 | NP_008970.1 | 1.4 | 2.4 | 0.000571 | 0.000259 | 1723.5 | |
| eukaryotic translation initiation factor 2C | EIF2C2 | mwghuman3 0K#C:2287 | NM_012154.2 | NP_036286.2 | 1.4 | 2.5 | 0.00011 | 0.0000243 | 1730 | |
| WD repeat domain 18 | WDR18 | mwghuman3 0K#B:3546 | NM_024100.2 | NP_077005.2 | 1.4 | 3.2 | 0.0000511 | 0.0000582 | 1748.5 | |
| tensin | TNS | mwghuman3 0K#B:8493 | NM_022648.2 | NP_072174.2 | 1.3 | 2.0 | 0.0000393 | 0.000177 | 1753.5 | |
| c-src tyrosine kinase | CSK | mwghuman3 0K#A:01629 | NM_004383.1 | NP_004374.1 | 1.4 | 1.9 | 1.05E-06 | 0.0000107 | 1935.5 | |
| ubiquitin-conjugating enzyme E2C | UBE2C | mwghuman3 0K#A:01776 | NM_181803.1 | NP_861519.1 | 2.1 | 8.3 | 0.001146 | 0.003908 | 2155 | |
| neuropilin 1 | NRP1 | mwghuman3 0K#A:03091 | NM_003873.2 | NP_003864.2 | 1.9 | 6.0 | 0.003291 | 0.003636 | 2941 | |

Fig. 12 (continued)

| control | number | TCC | number |
|---|---|---|---|
| other urological cancer | 35 | Ta grade 1 | 9 |
| benign prostate hyperplasia | 10 | Ta grade 2 | 28 |
| miscellaneous non malignant urological disease | 10 | T1 stage 2 | 4 |
| TCC surveillance (no cancer) | 47 | Tis stage 1 | 1 |
| urinary tract infection | 21 | Tis stage 2 | 1 |

Fig. 13

| | Area under curve (%) | | | |
|---|---|---|---|---|
| TCC characteristic | HoxA13 | HoxA13/LTB4DH | IGFBP5 | IGFBP5/LTB4DH |
| Stage Ta (grades 1-2) | 64 | 67 | 61 | 70 |
| Stage Ta (grade 1) | 66 | 69 | 73 | 81 |
| Grade 1 (all stages) | 66 | 69 | 73 | 81 |
| Grade 2 (all stages) | 62 | 62 | 55 | 63 |
| Grade 1-2 (all) | 64 | 64 | 60 | 68 |

Fig. 14

| BTM | Overall Sensitivity | stage Ta | grade 1&2 | grade 3 |
|---|---|---|---|---|
| cdc2 Hoxa13, MDK | 0.61 | 0.41 | 0.42 | 0.86 |
| cdc2, Hoxa13, MDK, LTB4DH | 0.63 | 0.44 | 0.43 | 0.89 |
| cdc2 Hoxa13, IGFBP5, MDK | 0.61 | 0.44 | 0.44 | 0.82 |
| cdc2 Hoxa13, IGFBP5, MDK, LTB4DH | 0.62 | 0.46 | 0.45 | 0.84 |
| cdc2, IGFBP5, MDK | 0.61 | 0.44 | 0.45 | 0.82 |
| cdc2, IGFBP5, MDK, LTB4DH | 0.62 | 0.46 | 0.45 | 0.85 |
| Hoxa13, IGFBP5, MDK, Top2a | 0.61 | 0.44 | 0.45 | 0.83 |
| Hoxa13, IGFBP5, MDK, Top2a, LTB4DH | 0.63 | 0.47 | 0.46 | 0.85 |
| Hoxa13, IGFBP5, MDK | 0.61 | 0.44 | 0.45 | 0.83 |
| Hoxa13, IGFBP5, MDK, LTB4DH | 0.62 | 0.46 | 0.45 | 0.85 |
| HoxA13, MDK | 0.62 | 0.42 | 0.42 | 0.87 |
| HoxA13, MDK, LTB4DH | 0.64 | 0.45 | 0.44 | 0.89 |
| IGFBP5, MDK | 0.62 | 0.44 | 0.45 | 0.84 |
| IGFBP5, MDK, LTB4DH | 0.63 | 0.47 | 0.45 | 0.86 |
| cdc2, IGFBP5, MDK, Top2a | 0.62 | 0.45 | 0.45 | 0.84 |
| cdc2, IGFBP5, MDK, Top2a, LTB4DH | 0.64 | 0.48 | 0.46 | 0.87 |

Fig. 15

SEQUENCE LISTING

```
<160> NUMBER OF SEQ ID NOS: 11

<210> SEQ ID NO 1
<211> LENGTH: 22
<212> TYPE: DNA
<213> ORGANISM: Homo sapiens

<400> SEQUENCE: 1
aattgtgacc gcaaaggatt ct                                          22

<210> SEQ ID NO 2
<211> LENGTH: 18
<212> TYPE: DNA
<213> ORGANISM: Homo sapiens

<400> SEQUENCE: 2
cagcagatgc cacgcttg                                               18

<210> SEQ ID NO 3
<211> LENGTH: 27
<212> TYPE: DNA
<213> ORGANISM: Homo sapiens

<400> SEQUENCE: 3
aagagaaagc agtgcaaacc ttcccgt                                     27

<210> SEQ ID NO 4
```

-continued

```
<211> LENGTH: 22
<212> TYPE: DNA
<213> ORGANISM: Homo sapiens

<400> SEQUENCE: 4
tataacagaa ccggcccact tc                                              22

<210> SEQ ID NO 5
<211> LENGTH: 21
<212> TYPE: DNA
<213> ORGANISM: Homo sapiens

<400> SEQUENCE: 5
cccatttcag caagtccttc a                                               21

<210> SEQ ID NO 6
<211> LENGTH: 22
<212> TYPE: DNA
<213> ORGANISM: Homo sapiens

<400> SEQUENCE: 6
ccaggcccac ccccagagat tg                                              22

<210> SEQ ID NO 7
<211> LENGTH: 28
<212> TYPE: DNA
<213> ORGANISM: Homo sapiens

<400> SEQUENCE: 7
tgtctaccct tatacacaac tccatagg                                        28

<210> SEQ ID NO 8
<211> LENGTH: 31
<212> TYPE: DNA
<213> ORGANISM: Homo sapiens

<400> SEQUENCE: 8
agccgggatc taccataccc attgactaac t                                    31

<210> SEQ ID NO 9
<211> LENGTH: 20
<212> TYPE: DNA
<213> ORGANISM: Homo sapiens

<400> SEQUENCE: 9
ccgcccagac acctacattg                                                 20

<210> SEQ ID NO 10
<211> LENGTH: 26
<212> TYPE: DNA
<213> ORGANISM: Homo sapiens

<400> SEQUENCE: 10
tgtacaaacc aggaacaaaa gtgact                                          26

<210> SEQ ID NO 11
<211> LENGTH: 30
<212> TYPE: DNA
<213> ORGANISM: Homo sapiens

<400> SEQUENCE: 11
ttctgtggaa ttagtgaccc agcaaatgtg                                      30
```

URINE GENE EXPRESSION RATIOS FOR DETECTION OF CANCER

CLAIM OF PRIORITY

This application is a Continuation application filed under 35 U.S.C. §111(a) and 37 C.F.R. §1.53(b) of non-provisional U.S. application Ser. No. 12/221,626, filed 5 Aug. 2008, which is a Continuation application filed under 35 U.S.C. 111(a) of PCT International Application Number PCT/NZ2007/000029, International Filing Date Feb. 9, 2007, Inventor Parry Guilford, entitled "Urine Gene Expression Ratios for Detection of Cancer." The above PCT Application claims priority to New Zealand provisional patent application number NZ 545,243, filed 10 Feb. 2006. Each of the above applications is expressly incorporated herein fully by reference, as if individually so incorporated.

TECHNICAL FIELD

This invention relates to detection of cancer. Specifically, the invention relates to the use of markers for the detection of bladder cancer. More specifically, this invention relates to use of an under-expressed marker in combination with at least one other marker for the detection of bladder cancer.

BACKGROUND

Survival of cancer patients is greatly enhanced when the cancer is treated early. In the case of bladder cancer, patients diagnosed with early stage disease have 5-year survival rates of >90%, compared to approximately 15-30% for patients diagnosed with advanced disease. Therefore, developments that lead to early diagnosis of bladder cancer can lead to an improved prognosis for the patients. The established method for detecting bladder cancer using urine samples is cytology. However, cytology is known to be only about 75% sensitive for detecting invasive bladder cancer and only about 25% sensitive for detecting superficial bladder cancer (Lotan and Roehrborn, Urology 61, 109-118 (2003)).

Identification of specific markers for cancer in urine can provide a valuable approach for the early diagnosis of cancer, leading to early treatment and improved prognosis. Specific cancer markers also provide a means for monitoring disease progression, enabling the efficacy of surgical, radiotherapeutic and chemotherapeutic treatments to be monitored.

At present, the most reliable method for detecting bladder cancer is cystoscopy accompanied by histology of biopsied lesions. However, this technique is time consuming, invasive and its sensitivity is only approximately 90%, meaning that about 10 percent of cancers are not detected using these methods. Of the non-invasive methodologies, urine cytology, which detects exfoliated malignant cells microscopically, is the current preferred method. Although cytology has a specificity of about 95%, it has poor sensitivity (9-25%) for low-grade lesions, is extremely dependent on sample quality and suffers from high inter-observer variability.

Several urine protein markers are known. Tests for these markers offer better sensitivity than cytology, but tend to suffer from sub-optimal specificity because elevated levels of these markers are also commonly observed in patients with non-malignant diseases including inflammation, urolithiasis and benign prostatic hyperplasia. For example, NMP22, which detects a specific nuclear matrix protein, has a sensitivity of 47-87% and a specificity of 58-91%.

One drawback associated with urine testing is that individual marker levels can vary significantly with: (i) different urine collection methods (catheterised, voided, urine pellets); (ii) the diurnal timing of urine sampling; (iii) the point of sampling during voiding (e.g. midstream vs end sample); and (iv) urine concentration associated with varying fluid intake, kidney function or diseases that affect plasma volume. These variations have the potential to lead to false positive and false negative tests. Although some of this variation can be reduced using strict standard operating procedures, patient compliance with these procedures can be unreliable. The effect of varying urine concentration can, in some instances, be accounted for by assessing marker levels relative to urinary creatinine, however, this increases the cost and complexity of testing, particularly when sample preparation or storage methods differ for marker detection and creatinine measurement.

There is a need for simple tools for the early detection and diagnosis of cancer. This invention provides further methods, devices and kits based on markers, specifically ratios, regression or classification analysis of bladder cancer markers, to aid in the detection and diagnosis of bladder cancer.

SUMMARY OF THE INVENTION

The present invention provides for a method for determining the presence of a cancer in a subject, comprising:
  (a) providing a sample from the subject;
  (b) detecting the expression level of at least two tumour marker (TM) family members in said sample, wherein at least one TM is an under-expressed TM;
  (c) establishing whether the patient has cancer according to a predetermined threshold.

Step (c) can be preformed by determining the ratio of expression of said TMs, or by performing regression or classification analysis on the TM expression levels.

The TM can be a BTM. The cancer to be detected can be bladder cancer, and in certain embodiments at least one of the TMs is an over-expressed BTM. The over-expressed BTM may be selected from the group outlined in FIG. 11 or FIG. 12.

In certain embodiments at least one under-expressed TM is a BTM selected from the group outlined in FIG. 3 or FIG. 4.

In other embodiments of the present invention the step of detecting is carried out by detecting over expression of BTM mRNA, a BTM protein, or a BTM peptide.

The sample can be any one of biopsy, blood, serum, peritoneal washes, cerebrospinal fluid, urine and stool samples The present invention also provides for a device for detecting a TM, comprising:
  a substrate having a TM capture reagent thereon; and
  a detector associated with said substrate, said detector capable of detecting a TM associated with said capture reagent, wherein the TM is an under-expressed TM.

The TM can be a BTM.

The TM capture reagent can be an oligonucleotide or an antibody.

In certain embodiments the TM can be a BTM selected from the group outlined in FIG. 3 or FIG. 4.

The present invention also provides for a kit for determining the presence of a cancer in a subject, comprising:
  a substrate;
  at least two TM capture reagents, wherein at least one TM is an under-expressed TM; and
  instructions for use.

The TM can be a BTM.

The TM capture reagent may be a TM-specific oligonucleotide or a TM-specific antibody.

The TM detected by the kit may be a BTM selected from the group outlined in FIG. 3 or FIG. 4.

At least one of the TMs detected by the kit may be an over-expressed TM or an over-expressed BTM. The over-expressed BTM may be selected from the group outlined in FIG. 11 or FIG. 12.

BRIEF DESCRIPTION OF THE FIGURES

This invention is described with reference to specific embodiments thereof and with reference to the Figures, in which:

FIG. 1 depicts a table showing the characteristics of urine samples used in the qPCR analyses.

FIG. 2 depicts a table of primers and oligonucleotide probes of markers for qPCR analysis of bladder cancer according to the present invention.

FIG. 3 depicts a table of under-expressing bladder tumour markers identified using microarray methods on samples of bladder cancer.

FIG. 4 depicts a table of under-expressing bladder tumour markers identified using microarray methods on samples of bladder cancer that have insignificant expression in whole blood, but high expression in normal bladder tissue.

FIG. 6 shows examples of the sensitivities and specificities of TCC detection for tests that include LTB4DH. (a). single tests; (b). combination tests using LTB4DH and two of the three markers HoxA13, IGFBP5, and MDK.

FIG. 8a-f shows scatter plots for combination tests, a-c using LTB4DH and two of the three markers HoxA13, IGFBP5, and MDK, and d-f repeated using BAG1 for LTB4DH. 8a. MDK/LTB4DH and IGFBP5/LTB4DH; 8b. MDK/LTB4DH and HoxA13/LTB4DH; IGFBP5/LTB4DH and HoxA13/LTB4DH; 8d MDK/BAG1 and IGFBP5/BAG1; 8e.MDK/BAG1 and HoxA13/BAG1; 8f. IGFBP5/BAG1 and HoxA13/BAG1.

FIG. 9a-b shows scatter plots showing the correlation between ΔCt for IGFBP5 and ΔCt ratios for IGFBP5/LTB4DH and urine creatinine concentration. 9a. Urine samples from patients with TCC 9b. Urine samples from patients with non-malignant disease FIG. 10a-f depicts self-self scatter plots showing the distribution of voided and catheterised urine samples from TCC patients analysed using the bladder tumour markers MDK, IGFBP5 and HoxA13 alone or in ratios with LTB4DH.

FIG. 11 shows known over-expressed markers from invasive bladder tumours.

FIG. 12 shows known over-expressed markers from superficial bladder tumours.

FIG. 13 shows the clinical characteristics of low grade TCC samples and controls used in ROC curve analysis.

FIG. 14 shows the results of a ROC Curve analysis. Illustration of the increased test accuracy obtained when LTB4DH is used in ratios with HoxA13 and IGFBP5.

FIG. 15 shows the results of a Linear Discriminate Analysis of BTMs, with and without LTB4DH, for the detection of TCC.

DETAILED DESCRIPTION

Definitions

Figure 5:
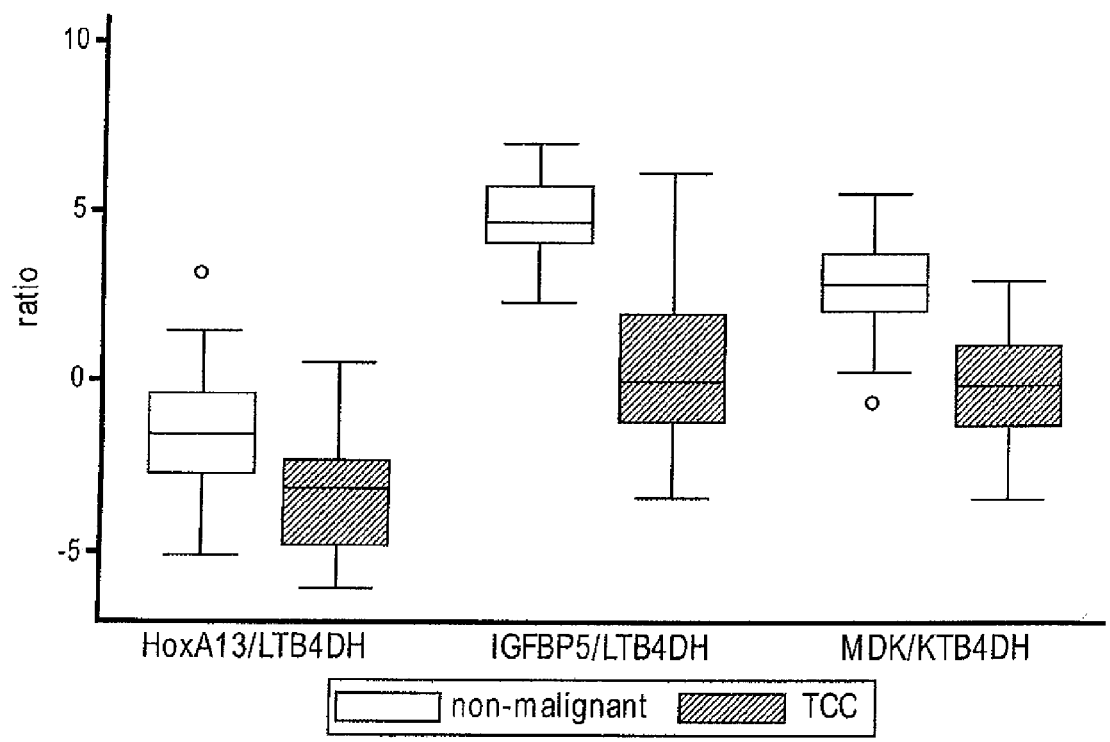
FIG. 5 depicts box and whisker plots showing the ratios of three bladder transitional cell carcinoma (TCC) markers (HoxA13, IGFBP5, and MDK) with the under expressing marker LTB4DH for urine samples from patients with either non-malignant urological disease or TCC. The boxes define the $25^{th}$, $50^{th}$ and $75^{th}$ percentiles and the horizontal bars mark the adjacent values. Outliers are shown by circles. The unfilled boxes represent samples from non-malignant disease controls and the shaded boxes represent samples from patients with TCC.

The term "marker" means a molecule that is associated quantitatively or qualitatively with the presence of a biological phenomenon. Examples of "markers" include a polynucleotide, such as a gene, gene fragment, RNA, or RNA fragment; or a gene product, including a polypeptide such as a peptide, oligopeptide protein or protein fragment; or related metabolites, by products or other identifying molecules, such as antibodies or antibody fragments whether related directly or indirectly to a mechanism underlying the phenomenon. The markers of the invention include the nucleotide sequences (e.g. GenBank sequences) as disclosed herein, in particular the full length sequences, any coding sequences, non-coding sequences and fragments, or any compliments thereof, and any measurable marker thereof as defined above.

The term "sensitivity" means the proportion of individuals with the disease who test (by the model) positive. Thus, increased sensitivity means fewer false negative test results.

The term "specificity" means the proportion of individuals without the disease who test (by the model) negative. Thus, increased specificity means fewer false positive test results. The term "expression" includes production of polynucleotides and polypeptides, in particular, the production of RNA (e.g., mRNA) from a gene or portion of a gene, and includes the production of a polypeptide encoded by an RNA or gene or portion of a gene, and includes appearance of a detectable material associated with expression. For example, the formation of a complex, for example, from a polypeptide-polypeptide interaction, polypeptide-nucleotide interaction, or the like, is included within the scope of the term "expression". Another example, the binding of a binding ligand, such as a hybridization probe or antibody, to a gene or other polynucleotide, a polypeptide or a protein fragment and the visualization of the binding ligand Thus, the density of a spot on a microarray, on a hybridization blot such as a Northern blot, or on an immunoblot, such as a Western blot, or on a bead array, or by PCR analysis, is included within the term "expression" of the underlying biological molecule.

The term "over expression" is used where the expression of a marker in one cell, or cell type, is greater than that of another equivalent cell, or cell type.

The term "under expression" is used where the expression of a marker in one cell, or cell type, is less than that of another equivalent cell, or cell type.

The term "TM" or "tumour marker" or "TM family member" means a marker that is associated with a particular cancer. The term TM also includes combinations of individual markers, whose combination improves the sensitivity and specificity of detecting cancer. It is to be understood that the term TM does not require that the marker be specific only for a particular tumour. Rather, expression of TM can be altered in other types of cells, diseased cells, tumours, including malignant tumours.

A TM can be identified by extracting RNA from a tissue sample from a patient suspected of having bladder cancer, applying the RNA or cDNA copy to a microarray having a number of oligonucleotides thereon, permitting the sample RNA to hybridize to the oligonucleotides on the array, and then quantifying the level of measured RNA bound to the each array spot. A marker is considered to be a under expressing TM if its presence is below a threshold of at least about 1.2 times that found in normal, non-malignant tissue using microarray methods. Alternatively, the threshold can be below about 2 times normal, about 3 times less than normal, 4 times or even about 5 times less than normal. By "normal" we mean less than the $90^{th}$ percentile of the normal population. In other cases, normal can mean a level of presence of the $95^{th}$ percentile (i.e., about 2 Standard Deviations (SD) from the mean), and in other cases, less than about $97.5^{th}$ percentile (i.e., about 3 SD) or the $99^{th}$ percentile.

The term "under expressing TM" means a marker that shows lower expression in bladder tumours than in non-malignant bladder tissue. The term "over expressing TM" means a marker that shows higher expression in bladder tumours than in non-malignant tissue.

The term "BTM" or "bladder tumour marker" or "BTM family member" means a TM that is associated with bladder cancer. The term BTM also includes combinations of individual markers, whose combination improves the sensitivity and specificity of detecting bladder cancer. It is to be understood that the term BTM does not require that the marker be specific only for bladder tumours. Rather, expression of BTM can be altered in other types of cells, diseased cells, tumours, including malignant tumours.

The term "under expressing BTM" means a marker that shows lower expression in bladder tumours than in non-malignant bladder tissue.

The term "over expressing BTM" means a marker that shows higher expression in bladder tumours than in non-malignant tissue.

The term "qPCR" means quantitative polymerase chain reaction. The term "qPCR" or "QPCR" refers to quantative polymerase chain reaction as described, for example, in PCR Technique: Quantitative PCR, J. W. Larrick, ed., Eaton Publishing, 1997, and A-Z of Quantitative PCR, S. Bustin, ed., IUL Press, 2004.

The term "TCC" means transitional cell carcinoma of the bladder. TCCs constitute ~95% of all bladder cancers.

As used herein "antibodies" and like terms refer to immunoglobulin molecules and immunologically active portions of immunoglobulin (Ig) molecules, i.e., molecules that contain an antigen binding site that specifically binds (immunoreacts with) an antigen. These include, but are not limited to, polyclonal, monoclonal, chimeric, single chain, Fc, Fab, Fab', and Fab2 fragments, and a Fab expression library. Antibody molecules relate to any of the classes IgG, IgM, IgA, IgE, and IgD, which differ from one another by the nature of heavy chain present in the molecule. These include subclasses as well, such as IgG1, IgG2, and others. The light chain may be a kappa chain or a lambda chain. Reference herein to antibodies includes a reference to all classes, subclasses, and types. Also included are chimeric antibodies, for example, monoclonal antibodies or fragments thereof that are specific to more than one source, e.g., a mouse or human sequence. Further included are camelid antibodies, shark antibodies or nanobodies.

The terms "cancer" and "cancerous" refer to or describe the physiological condition in mammals that is typically characterized by abnormal or unregulated cell growth. Cancer and cancer pathology can be associated, for example, with metastasis, interference with the normal functioning of neighbouring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

The term "tumour" refers to all neoplastic cell growth and proliferation, whether malignant or benign, and all pre-cancerous and cancerous cells and tissues.

The term "microarray" refers to an ordered or unordered arrangement of capture agents, preferably polynucleotides (e.g., probes) or polypeptides on a substrate. See, e.g., Microarray Analysis, M. Schena, John Wiley & Sons, 2002; Microarray Biochip Technology, M. Schena, ed., Eaton Publishing, 2000; Guide to Analysis of DNA Microarray Data, S. Knudsen, John Wiley & Sons, 2004; and Protein Microarray Technology, D. Kambhampati, ed., John Wiley & Sons, 2004.

The term "oligonucleotide" refers to a polynucleotide, typically a probe or primer, including, without limitation, single-stranded deoxyribonucleotides, single- or double-stranded ribonucleotides, RNA:DNA hybrids, and double-stranded DNAs. Oligonucleotides, such as single-stranded DNA probe oligonucleotides, are often synthesized by chemical methods, for example using automated oligonucleotide synthesizers that are commercially available, or by a variety of other methods, including in vitro expression systems, recombinant techniques, and expression in cells and organisms.

The term "polynucleotide," when used in the singular or plural, generally refers to any polyribonucleotide or polydeoxribonucleotide, which may be unmodified RNA or DNA or modified RNA or DNA. This includes, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. Also included are triple-stranded regions comprising RNA or DNA or both RNA and DNA. Specifically included are mRNAs, cDNAs, and genomic DNAs, and any fragments thereof. The term includes DNAs and RNAs that contain one or more modified bases, such as tritiated bases, or unusual bases, such as inosine. The polynucleotides of the invention can encompass coding or non-coding sequences, or sense or antisense sequences. It will be understood that each reference to a "polynucleotide" or like term, herein, will include the full-length sequences as well as any fragments, derivatives, or variants thereof.

"Polypeptide," as used herein, refers to an oligopeptide, peptide, or protein sequence, or fragment thereof, and to naturally occurring, recombinant, synthetic, or semi-synthetic molecules. Where "polypeptide" is recited herein to refer to an amino acid sequence of a naturally occurring protein molecule, "polypeptide" and like terms, are not meant to limit the amino acid sequence to the complete, native amino acid sequence for the full-length molecule. It will be understood that each reference to a "polypeptide" or like term, herein, will include the full-length sequence, as well as any fragments, derivatives, or variants thereof.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridisable sequence, the higher the relative temperature which can be used. As a result, it follows that higher relative temperatures would tend to make the reaction conditions more stringent, while lower temperatures less so. Additional details and explanation of stringency of hybridization reactions, are found e.g., in Ausubel et al., Current Protocols in Molecular Biology, Wiley Interscience Publishers, (1995).

"Stringent conditions" or "high stringency conditions", as defined herein, typically: (1) employ low ionic strength and high temperature for washing, for example 0.015 M sodium chloride/0.0015 M sodium citrate/0.1% sodium dodecyl sulfate at 50° C.; (2) employ a denaturing agent during hybridization, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×, Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash comprising 0.1×SSC containing EDTA at 55° C.

"Moderately stringent conditions" may be identified as described by Sambrook et al., Molecular Cloning: A Laboratory Manual, New York: Cold Spring Harbor Press, 1989, and include the use of washing solution and hybridization conditions (e. g., temperature, ionic strength, and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5× Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The practice of the present invention will employ, unless otherwise indicated, conventional techniques of molecular biology (including recombinant techniques), microbiology, cell biology, and biochemistry, which are within the skill of the art. Such techniques are explained fully in the literature, such as, Molecular Cloning: A Laboratory Manual, 2nd edition, Sambrook et al., 1989; Oligonucleotide Synthesis, M J Gait, ed., 1984; Animal Cell Culture, R. I. Freshney, ed., 1987; Methods in Enzymology, Academic Press, Inc.; Handbook of Experimental Immunology, 4th edition, D. M. Weir & C C. Blackwell, eds., Blackwell Science Inc., 1987; Gene Transfer Vectors for Mammalian, Cells, J. M. Miller & M. P. Calos, eds., 1987; Current Protocols in Molecular Biology, F. M. Ausubel et al., eds., 1987; and PCR: The Polymerase Chain Reaction, Mullis et al., eds., 1994.

Description of Embodiments of the Invention

Using a combination of microarray analysis and quantitative polymerase chain reaction (qPCR), markers for transitional cell carcinoma of the bladder (TCC) that are under-expressed in tumours have been identified. It has surprisingly been found that ratios between these markers and other bladder tumour markers (BTM), especially markers that are over expressed in tumours, are diagnostic for bladder cancer.

The ratios (rather than measuring an absolute level of a marker) identifies a simple gene expression 'signature' that typifies bladder cancer cells, and surprisingly is more robust to variations in sampling techniques or urine concentration. Moreover, the combination of an under-expressed marker and an over-expressed marker maximizes the differential between samples from patients and non-malignant controls, increasing the test reliability. The under-expressed markers described here have been selected on the basis of (i) strong and consistent down-regulation in TCC, (ii) high expression in normal tissue, and (iii) insignificant expression in whole blood to minimize the risk of false positives in patients presenting with hematuria.

As an alternative to determining the ration of the two BTM,s it has also been found that the under-expressed and over-expressed BTMs can be analysed in regression analyses or classification techniques including linear discriminate analysis, and the results of these analyses are also indicative of the presence of bladder cancer.

The test involves the measuring of at least two TM markers, such as a BTM, in a sample from a patient suspected of having a cancer or at risk of having cancer, wherein at least one of the TMs is an under-expressed TM. The ratio of the under-expressed TM and the other TM is indicative of the presence of cancer. The second TM can be any TM as known in the art, but preferably is an over-expressed BTM, FIG. 3 shows a number of under-expressed markers suitable for use in the present invention.

The test is best preformed using an under-expressed TM in combination with an over-expressed TM. Any over-expressed TM can be used, for example. Known over expressed BTMs identified from invasive bladder tumours (defined here as tumours≥stage 1), are outlined in FIG. 11, and over-expressed BTMs identified from superficial bladder tumours (defined here as Stage Ta and Tis tumours) are shown in FIG. 12.

It has also been surprisingly established that preferred under-expressed BTMs for use in the present invention are ones that are not significantly elevated in whole blood, and are present in sufficiently high copy numbers in both tumour cells and non-malignant bladder cells. Preferred under-expressed BTMs are outlined in FIG. 4.

Cancer markers can be detected in a sample using any suitable technique, and can include, but are not limited to, oligonucleotide probes, qPCR or antibodies raised against cancer markers.

It will be appreciated that the sample to be tested is not restricted to a sample of the tissue suspected of being a tumour. The marker may be secreted into the serum, sloughed from cell membranes, released from lysed cells or associated with cells lost into the urine. Therefore, a sample can include any bodily sample, and includes biopsies, blood, serum, peritoneal washes, cerebrospinal fluid, urine and stool samples.

It will also be appreciate that the present invention is not restricted to the detection of cancer in humans, but is suitable for the detection of cancer in any animal, including, but not limited to dogs, cats, horses, cattle, sheep, deer, pigs and any other animal known to get cancer.

General Approaches to Cancer Detection

The following approaches are non-limiting methods that can be used to measure TMs. Following measurement of individual TMs, ratios between high and low expressing BTM family members are determined. These ratios are used to predict the presence or absence cancer.

Alternatively, the high and low expressing TMs are used in regression or classification analyses. The results of these analyses are also used to predict the presence or absence cancer.

General methodologies for determining expression levels are outlined below, although it will be appreciated that any method for determining expression levels would be suitable.

Quantitative PCR (qPCR)

Quantitative PCR (qPCR) can be carried out on tumour samples, on serum, plasma and urine samples using BTM specific primers and probes. In controlled reactions, the amount of product formed in a PCR reaction (Sambrook, J., E Fritsch, E. and T Maniatis, Molecular Cloning: A Laboratory Manual 3$^{rd}$. Cold Spring Harbor Laboratory Press: Cold Spring Harbor (2001)) correlates with the amount of starting template. Quantification of the PCR product can be carried out by stopping the PCR reaction when it is in log phase, before reagents become limiting. The PCR products are then electrophoresed in agarose or polyacrylamide gels, stained with ethidium bromide or a comparable DNA stain, and the intensity of staining measured by densitometry. Alternatively, the progression of a PCR reaction can be measured using PCR machines such as the Applied Biosystems' Prism 7000 or the Roche LightCycler which measure product accumulation in real-time. Real-time PCR measures either the fluorescence of DNA intercalating dyes such as Sybr Green into the synthesized PCR product, or the fluorescence released by a reporter molecule when cleaved from a quencher molecule; the reporter and quencher molecules are incorporated into an oligonucleotide probe which hybridizes to the target DNA molecule following DNA strand extension from the primer oligonucleotides. The oligonucleotide probe is displaced and degraded by the enzymatic action of the Taq polymerase in the next PCR cycle, releasing the reporter from the quencher molecule. In one variation, known as Scorpion®, the probe is covalently linked to the primer.

Reverse Transcription PCR (RT-PCR)

RT-PCR can, be used to compare RNA levels in different sample populations, in normal and tumour tissues, with or without drug treatment, to characterize patterns of expression, to discriminate between closely related RNAs, and to analyze RNA structure.

For RT-PCR, the first step is the isolation of RNA from a target sample. The starting material is typically total RNA isolated from human tumours or tumour cell lines, and corresponding normal tissues or cell lines, respectively. RNA can be isolated from a variety of samples, such as tumour samples from breast, lung, colon (e.g., large bowel or small bowel), colorectal, gastric, esophageal, anal, rectal, prostate, brain, liver, kidney, pancreas, spleen, thymus, testis, ovary, uterus, bladder etc., tissues, from primary tumours, or tumour cell lines, and from pooled samples from healthy donors. If the source of RNA is a tumour, RNA can be extracted, for example, from frozen or archived paraffin-embedded and fixed (e.g., formalin-fixed) tissue samples.

The first step in gene expression profiling by RT-PCR is the reverse transcription of the RNA template into cDNA, followed by its exponential amplification in a PCR reaction. The two most commonly used reverse transcriptases are avian myeloblastosis virus reverse transcriptase (AMV-RT) and Moloney murine leukaemia virus reverse transcriptase (MMLV-RT). The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, Calif., USA), following the manufacturer's instructions. The derived cDNA can then be used as a template in the subsequent PCR reaction.

Although the PCR step can use a variety of thermostable DNA-dependent DNA polymerases, it typically employs the Taq DNA polymerase, which has a 5'-3' nuclease activity but lacks a 3'-5' proofreading endonuclease activity. Thus, TaqMan (q) PCR typically utilizes the 5' nuclease activity of Taq or Tth polymerase to hydrolyze a hybridization probe bound to its target amplicon, but any enzyme with equivalent 5' nuclease activity can be used.

Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TaqMan RT-PCR can be performed using commercially available equipment, such as, for example, ABI PRISM 7700 Sequence Detection System (Perkin-Elmer-Applied Biosystems, Foster City, Calif., USA), or Lightcycler (Roche Molecular Biochemicals, Mannheim, Germany). In a preferred embodiment, the 5' nuclease procedure is run on a real-time quantitative PCR device such as the ABI PRISM 7700tam Sequence Detection System.

The system consists of a thermocycler, laser, charge-coupled device (CCD), camera, and computer. The system amplifies samples in a 96-well format on a thermocycler. During amplification, laser-induced fluorescent signal is collected in real-time through fibre optics cables for all 96 wells, and detected at the CCD. The system includes software for running the instrument and for analyzing the data.

5' nuclease assay data are initially expressed as Ct, or the threshold cycle. As discussed above, fluorescence values are recorded during every cycle and represent the amount of product amplified to that point in the amplification reaction. The point when the fluorescent signal is first recorded as statistically significant is the threshold cycle.

Real-Time Quantitative PCR (qPCR)

A more recent variation of the RT-PCR technique is the real time quantitative PCR, which measures PCR product accumulation through a dual-labeled fluorigenic probe (i.e., TaqMan probe). Real time PCR is compatible both with quantitative competitive PCR and with quantitative comparative PCR. The former uses an internal competitor for each target sequence for normalization, while the latter uses a normalization gene contained within the sample, or a housekeeping gene for RT-PCR. Further details are provided, e.g., by Held et al., Genome Research 6: 986-994 (1996).

Expression levels can be determined using fixed, paraffin-embedded tissues as the RNA source. According to one aspect of the present invention, PCR primers and probes are designed based upon intron sequences present in the gene to be amplified. In this embodiment, the first step in the primer/probe design is the delineation of intron sequences within the genes. This can be done by publicly available software, such as the DNA BLAT software developed by Kent, W. J., Genome Res. 12 (4): 656-64 (2002), or by the BLAST software including its variations. Subsequent steps follow well established methods of PCR primer and probe design.

In order to avoid non-specific signals, it is useful to mask repetitive sequences within the introns when designing the primers and probes. This can be easily accomplished by using the Repeat Masker program available on-line through the Baylor College of Medicine, which screens DNA sequences against a library of repetitive elements and returns a query sequence in which the repetitive elements are masked. The masked sequences can then be used to design primer and probe sequences using any commercially or otherwise publicly available primer/probe design packages, such as Primer Express (Applied Biosystems); MGB assay-by-design (Applied Biosystems); Primer3 (Steve Rozen and Helen J. Skaletsky (2000) Primer3 on the WWW for general users and for biologist programmers in: Krawetz S, Misener S (eds) Bioinformatics Methods and Protocols: Methods in Molecular Biology. Humana Press, Totowa, N.J., pp 365-386).

The most important factors considered in PCR primer design include primer length, melting temperature (Tm), and G/C content, specificity, complementary primer sequences, and 3' end sequence. In general, optimal PCR primers are generally 17-30 bases in length, and contain about 20-80%, such as, for example, about 50-60% G+C bases. Melting temperatures between 50 and 80° C., e.g., about 50 to 70° C., are typically preferred. For further guidelines for PCR primer and probe design see, e.g., Dieffenbach, C. W. et al., General Concepts for PCR Primer Design in: PCR Primer, A Laboratory Manual, Cold Spring Harbor Laboratory Press, New York, 1995, pp. 133-155; Innis and Gelfand, Optimization of PCRs in: PCR Protocols, A Guide to Methods and Applications, CRC Press, London, 1994, pp. 5-11; and Plasterer, T. N. Primerselect: Primer and probe design. Methods Mol. Biol. 70: 520-527 (1997), the entire disclosures of which are hereby expressly incorporated by reference.

Microarray Analysis

Differential expression can also be identified, or confirmed using the microarray technique. Thus, the expression profile of CCPMs can be measured in either fresh or paraffin-embedded tumour tissue, using microarray technology. In this method, polynucleotide sequences of interest (including cDNAs and oligonucleotides) are plated, or arrayed, on a microchip substrate. The arrayed sequences (i.e., capture probes) are then hybridized with specific polynucleotides from cells or tissues of interest (i.e., targets). Just as in the RT-PCR method, the source of RNA typically is total RNA isolated from human tumours or tumour cell lines, and corresponding normal tissues or cell lines. Thus RNA can be isolated from a variety of primary tumours or tumour cell lines. If the source of RNA is a primary tumour, RNA can be extracted, for example, from frozen or archived formalin fixed paraffin-embedded (FFPE) tissue samples and fixed (e.g., formalin-fixed) tissue samples, which are routinely prepared and preserved in everyday clinical practice.

In a specific embodiment of the microarray technique, PCR amplified inserts of cDNA clones are applied to a substrate. The substrate can include up to 1, 2, 5, 10, 15, 20, 25, 30, 35, 40, 45, 50, or 75 nucleotide sequences. In other aspects, the substrate can include at least 10,000 nucleotide sequences. The microarrayed sequences, immobilized on the microchip, are suitable for hybridization under stringent conditions. As other embodiments, the targets for the microarrays can be at least 50, 100, 200, 400, 500, 1000, or 2000 bases in length; or 50-100, 100-200, 100-500, 100-1000, 100-2000, or 500-5000 bases in length. As further embodiments, the capture probes for the microarrays can be at least 10, 15, 20, 25, 50, 75, 80, or 100 bases in length; or 10-15, 10-20, 10-25, 10-50, 10-75, 10-80, or 20-80 bases in length.

Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the chip is scanned by confocal laser microscopy or by another detection method, such as a CCD camera. Quantitation of hybridization of each arrayed element allows for assessment of corresponding mRNA abundance. With dual colour fluorescence, separately labeled cDNA probes generated from two sources of RNA are hybridized pairwise to the array. The relative abundance of the transcripts from the two sources corresponding to each specified gene is thus determined simultaneously. An exemplary protocol for this is described in detail in Example 4.

The miniaturized scale of the hybridization affords a convenient and rapid evaluation of the expression pattern for large numbers of genes. Such methods have been shown to have the sensitivity required to detect rare transcripts, which are expressed at a few copies per cell, and to reproducibly detect at least approximately two-fold differences in the expression levels (Schena et al., Proc. Natl. Acad. Sci. USA 93 (2): 106-149 (1996)). Microarray analysis can be performed by commercially available equipment, following manufacturer's protocols, such as by using the Affymetrix GenChip technology, Illumina microarray technology or Incyte's microarray technology. The development of microarray methods for large-scale analysis of gene expression makes it possible to search systematically for molecular markers of cancer classification and outcome prediction in a variety of tumour types.

RNA Isolation, Purification, and Amplification

General methods for mRNA extraction are well known in the art and are disclosed in standard textbooks of molecular biology, including Ausubel et al., Current Protocols of Molecular Biology, John Wiley and Sons (1997). Methods for RNA extraction from paraffin embedded tissues are disclosed, for example, in Rupp and Locker, Lab Invest. 56: A67 (1987), and De Sandres et al., BioTechniques 18: 42044 (1995). In particular, RNA isolation can be performed using purification kit, buffer set, and protease from commercial manufacturers, such as Qiagen, according to the manufacturer's instructions. For example, total RNA from cells in culture can be isolated using Qiagen RNeasy mini-columns. Other commercially available RNA isolation kits include MasterPure Complete DNA and RNA Purification Kit (EPICENTRE (D, Madison, Wis.), and Paraffin Block RNA Isolation Kit (Ambion, Inc.). Total RNA from tissue samples can be isolated using RNA Stat-60 (Tel-Test). RNA prepared from tumour can be isolated, for example, by cesium chloride density gradient centrifugation.

The steps of a representative protocol for profiling gene expression using fixed, paraffin-embedded tissues as the RNA source, including mRNA isolation, purification, primer extension and amplification are given in various published journal articles (for example: T. E. Godfrey et al. J. Molec. Diagnostics 2: 84-91 (2000); K. Specht et al., Am. J. Pathol. 158: 419-29 (2001)). Briefly, a representative process starts with cutting about 10 µm thick sections of paraffin-embedded tumour tissue samples. The RNA is then extracted, and protein and DNA are removed. After analysis of the RNA concentration, RNA repair and/or amplification steps may be included, if necessary, and RNA is reverse transcribed using gene specific promoters followed by RT-PCR. Finally, the data are analyzed to identify the best treatment option(s) available to the patient on the basis of the characteristic gene expression pattern identified in the tumour sample examined.

Immunohistochemistry and Proteomics

Immunohistochemistry methods are also suitable for detecting the expression levels of the proliferation markers of the present invention. Thus, antibodies or antisera, preferably polyclonal antisera, and most preferably monoclonal antibodies specific for each marker, are used to detect expression. The antibodies can be detected by direct labeling of the antibodies themselves, for example, with radioactive labels, fluorescent labels, hapten labels such as, biotin, or an enzyme such as horse radish peroxidase or alkaline phosphatase. Alternatively, unlabeled primary antibody is used in conjunction with a labeled secondary antibody, comprising antisera, polyclonal antisera or a monoclonal antibody specific for the primary antibody. Immunohistochemistry protocols and kits are well known in the art and are commercially available.

Proteomics can be used to analyze the polypeptides present in a sample (e.g., tissue, organism, or cell culture) at a certain point of time. In particular, proteomic techniques can be used to assess the global changes of polypeptide expression in a sample (also referred to as expression proteomics). Proteomic analysis typically includes: (1) separation of individual polypeptides in a sample by 2-D gel electrophoresis (2-D PAGE); (2) identification of the individual polypeptides recovered from the gel, e.g., by mass spectrometry or N-terminal sequencing, and (3) analysis of the data using bioinformatics. Proteomics methods are valuable supplements to other methods of gene expression profiling, and can be used, alone or in combination with other methods, to detect the products of the proliferation markers of the present invention.

Hybridization Methods Using Nucleic Acid Probes Selective for a Marker

These methods involve binding the nucleic acid probe to a support, and hybridizing under appropriate conditions with RNA or cDNA derived from the test sample (Sambrook, J., E Fritsch, E. and T Maniatis, Molecular Cloning: A Laboratory Manual 3$^{rd}$. Cold Spring Harbor Laboratory Press: Cold Spring Harbor (2001)). These methods can be applied to BTM derived from a tumour tissue or fluid sample. The RNA or cDNA preparations are typically labeled with a fluorescent or radioactive molecule to enable detection and quantification. In some applications, the hybridizing DNA can be tagged with a branched, fluorescently labeled structure to enhance signal intensity (Nolte, F. S., Branched DNA signal amplification for direct quantitation of nucleic acid sequences in clinical specimens. Adv. Clin. Chem. 33, 201-35 (1998)). Unhybridized label is removed by extensive washing in low salt solutions such as 0.1×SSC, 0.5% SDS before quantifying the amount of hybridization by fluorescence detection or densitometry of gel images. The supports can be solid, such as nylon or nitrocellulose membranes, or consist of microspheres or beads that are hybridized when in liquid suspension. To allow washing and purification, the beads may be magnetic (Haukanes, B-I and Kvam, C., Application of magnetic beads in bioassays. Bio/Technology 11, 60-63 (1993)) or fluorescently-labeled to enable flow cytometry (see for example: Spiro, A., Lowe, M. and Brown, D., A Bead-Based Method for Multiplexed Identification and Quantitation of DNA Sequences Using Flow Cytometry. Appl. Env. Micro. 66, 4258-4265 (2000)).

A variation of hybridization technology is the QuantiGene Plex® assay (Genospectra, Fremont) which combines a fluorescent bead support with branched DNA signal amplification. Still another variation on hybridization technology is the Quantikine® mRNA assay (R&D Systems, Minn.). Methodology is as described in the manufacturer's instructions. Briefly the assay uses oligonucleotide hybridization probes conjugated to Digoxigenin. Hybridization is detected using anti-Digoxigenin antibodies coupled to alkaline phosphatase in colorometric assays.

Additional methods are well known in the art and need not be described further herein.

Enzyme-Linked Immunological Assays (ELISA)

Briefly, in sandwich ELISA assays, a polyclonal or monoclonal antibody against the BTM is bound to a solid support (Crowther, J. R. The ELISA guidebook. Humana Press: New Jersey (2000); Harlow, E. and Lane, D., Using antibodies: a laboratory manual. Cold Spring Harbor Laboratory Press: Cold Spring. Harbor (1999)) or suspension beads. Other methods are known in the art and need not be described herein further. Monoclonal antibodies can be hybridoma-derived or selected from phage antibody libraries (Hust M. and Dubel S., Phage display vectors for the in vitro generation of human antibody fragments. Methods Mol Biol. 295:71-96 (2005)). Non-specific binding sites are blocked with non-target protein preparations and detergents. The capture antibody is then incubated with a preparation of urine or tissue containing the BTM antigen. The mixture is washed before the antibody/antigen complex is incubated with a second antibody that detects the target BTM. The second antibody is typically conjugated to a fluorescent molecule or other reporter molecule that can either be detected in an enzymatic reaction or with a third antibody conjugated to a reporter (Crowther, Id.). Alternatively, in direct ELISAs, the preparation containing the BTM can be bound to the support or bead and the target antigen detected directly with an antibody-reporter conjugate (Crowther, Id.).

Methods for producing monoclonal antibodies and polyclonal antisera are well known in the art and need not be described herein further.

Immunodetection

The methods can also be used for immunodetection of marker family members in sera or plasma from bladder cancer patients taken before and after surgery to remove the tumour, immunodetection of marker family members in patients with other cancers, including but not limited to, colorectal, pancreatic, ovarian, melanoma, liver, oesophageal, stomach, endometrial, and brain and immunodetection of marker family members in urine and stool from bladder cancer patients.

BTMs can also be detected in tissues or urine using other standard immunodetection techniques such as immunoblotting or immunoprecipitation (Harlow, E. and Lane, D., Using antibodies: a laboratory manual. Cold Spring Harbor Laboratory Press: Cold Spring Harbor (1999)). In immunoblotting, protein preparations from tissue or fluid containing the BTM are electrophoresed through polyacrylamide gels under denaturing or non-denaturing conditions. The proteins are then transferred to a membrane support such as nylon. The BTM is then reacted directly or indirectly with monoclonal or polyclonal antibodies as described for immunohistochemistry. Alternatively, in some preparations, the proteins can be spotted directly onto membranes without prior electrophoretic separation. Signal can be quantified by densitometry.

In immunoprecipitation, a soluble preparation containing the BTM is incubated with a monoclonal or polyclonal antibody against the BTM. The reaction is then incubated with inert beads made of agarose or polyacrylamide with covalently attached protein A or protein G. The protein A or G beads specifically interact with the antibodies forming an immobilized complex of antibody-BTM-antigen bound to the bead. Following washing the bound BTM can be detected and quantified by immunoblotting or ELISA.

Threshold Determination

For tests using down-regulated BTMs in either ratios or regression analyses, thresholds will be derived that will enable a sample to be called either positive or negative for TCC. These thresholds will be determined by the analysis of cohorts of patients who are being investigated for the presence of TCC. Thresholds may vary for different test applications; for example, thresholds for use of the test in population screening will be determined using cohorts of patients who are largely free of urological symptoms, and these thresholds may be different to those used in tests for patients who are under surveillance for TCC recurrence, or those being investigated for the presence of urological symptoms such as hematuria. A threshold could be selected to provide a practical level of test specificity in the required clinical setting; that is, a specificity that allows reasonable sensitivity without excessive numbers of patients receiving false positive results. This specificity may be within the range of 80-90%. An alternative method to obtain a test threshold is to plot sensitivity against specificity for different test thresholds (ROC curves) then select the point of inflexion of the curve.

As an alternative to single thresholds, the test may use test intervals which provide different degrees of likelihood of presence of disease and which have different clinical consequences associated with them. For example, a test may have three intervals; one associated with a high (eg 90%) risk of the presence of TCC, a second associated with a low risk of TCC and a third regarded as being suspicious of disease. The "suspicious" interval could be associated with a recommendation for a repeat test in a defined period of time.

Methods for Detecting Bladder Cancer Markers in Urine

In several embodiments, assays for BTM can be desirably carried out on urine samples. In general, methods for assaying for oligonucleotides, proteins and peptides in these fluids are known in the art. However, for purposes of illustration, urine levels of a BTM can be quantified using a sandwich-type enzyme-linked immunosorbent assay (ELISA). For plasma or serum assays, a 5 µL aliquot of a properly diluted sample or serially diluted standard BTM and 75 µL of peroxidase-conjugated anti-human BTM antibody are added to wells of a microtiter plate. After a 30-minute incubation period at 30° C., the wells are washed with 0.05% Tween 20 in phosphate-buffered saline (PBS) to remove unbound antibody. Bound complexes of BTM and anti-BTM antibody are then incubated with o-phenylendiamine containing $H_2O_2$ for 15 minutes at 30° C. The reaction is stopped by adding 1 M $H_2SO_4$, and the absorbance at 492 nm is measured with a microtiter plate reader. It can be appreciated that anti-BTM antibodies can be monoclonal antibodies or polyclonal antisera.

Because many proteins are either (1) secreted by cells, (2) cleaved from cell membranes, (3) lost from cells upon cell death or (4) contained within sloughed cells, it will be appreciated that BTMs may also be detected in the urine. Additionally, diagnosis of bladder cancer can be determined by measuring either expression of BTMs in a sample, or accumulation of BTMs in a sample. Prior art methods of diagnosis include cystoscopy, cytology and examination of cells extracted during these procedures. Such methods have relied upon identification of tumour cells in the urine or in a brush sample of urothelium, or in other cases, in biopsy specimens of the bladder wall. These methods suffer from several types of errors, including sampling error, errors in identification between observers, and the like.

Antibodies to Bladder Tumour Markers

In additional aspects, this invention includes manufacture of antibodies against BTMs. Using methods described herein, novel BTMs can be identified using microarray and/or qPCR methods. Once a putative marker is identified, it can be produced in sufficient amount to be suitable for eliciting an immunological response. In some cases, a full-length BTM can be used, and in others, a peptide fragment of a BTM may be sufficient as an immunogen. The immunogen can be injected into a suitable host (e.g., mouse, rabbit, etc) and if desired, an adjuvant, such as Freund's complete adjuvant, Freund's incomplete adjuvant can be injected to increase the immune response. It can be appreciated that making antibodies is routine in the immunological arts and need not be described herein further. As a result, one can produce antibodies against BTMs identified using methods described herein.

In yet further embodiments, antibodies can be made against the protein or the protein core of the tumour markers identified herein or against an oligonucleotide sequence unique to a BTM. Although certain proteins can be glycosylated, variations in the pattern of glycosylation can, in certain circumstances, lead to mis-detection of forms of BTMs that lack usual glycosylation patterns. Thus, in certain aspects of this invention, BTM immunogens can include deglycosylated BTM or deglycosylated BTM fragments. Deglycosylation can be accomplished using one or more glycosidases known in the art. Alternatively, BTM cDNA can be expressed in glycosylation-deficient cell lines, such as prokaryotic cell lines, including *E. coli* and the like.

Vectors can be made having BTM-encoding oligonucleotides therein. Many such vectors can be based on standard vectors known in the art. Vectors can be used to transfect a variety of cell lines to produce BTM-producing cell lines, which can be used to produce desired quantities of BTM for development of specific antibodies or other reagents for detection of BTMs or for standardizing developed assays for BTMs.

Kits

Based on the discoveries of this invention, several types of test kits can be envisioned and produced. First, kits can be made that have a detection device pre-loaded with a detection molecule (or "capture reagent"). In embodiments for detection of BTM mRNA, such devices can comprise a substrate (e.g., glass, silicon, quartz, metal, etc) on which oligonucleotides as capture reagents that hybridize with the mRNA to be detected is bound. In some embodiments, direct detection of mRNA can be accomplished by hybridizing mRNA (labeled with cy3, cy5, radiolabel or other label) to the oligonucleotides on the substrate. In other embodiments, detection of mRNA can be accomplished by first making complementary DNA (cDNA) to the desired mRNA. Then, labeled cDNA can be hybridized to the oligonucleotides on the substrate and detected.

Antibodies can also be used in kits as capture reagents. In some embodiments, a substrate (e.g., a multiwell plate) can have a specific BTM capture reagent attached thereto. In some embodiments, a kit can have a blocking reagent included. Blocking reagents can be used to reduce non-specific binding. For example, non-specific oligonucleotide binding can be reduced using excess DNA from any convenient source that does not contain BTM oligonucleotides, such as salmon sperm DNA. Non-specific antibody binding can be reduced using an excess of a blocking protein such as serum albumin. It can be appreciated that numerous methods for detecting oligonucleotides and proteins are known in the art, and any strategy that can specifically detect BTM associated molecules can be used and be considered within the scope of this invention.

In addition to a substrate, a test kit can comprise capture reagents (such as probes), washing solutions (e.g., SSC, other salts, buffers, detergents and the like), as well as detection moieties (e.g., cy3, cy5, radiolabels, and the like). Kits can also include instructions for use and a package.

BTM ratios Used for Detection of Bladder Cancer I

In one series of embodiments, reagents for the testing the BTM LTBDH4 in combination with over-expressing BTMs can be incorporated into a kit for the testing of unfractionated urine or urine cell sediments to detect bladder cancer. The urine samples could be collected from patients with diagnosed bladder cancer who require monitoring for disease progression or treatment response, individuals with urological symptoms including macroscopic or microscopic hematuria, or asymptomatic individuals. For patients or individuals being tested with a kit that measures the BTMs in unfractionated urine, approximately 2 mls of urine can be taken for testing. For tests on the urine pellet, >10 mls of urine can be collected.

A suitable kit includes: (i) instructions for use and result interpretation, (ii) software for interpretation of multiple gene analyses, including any regression analysis classifier or formula (iii) reagents for the stabilization and purification of RNA from unfractionated urine or urine pellets, (iv) reagents for the synthesis of cDNA including dNTPs and reverse transcriptase, and (v) reagents for the quantification of the BTM cDNA. In one form, these reagents would be used for quantitative PCR and would include specific exon-spanning oligonucleotide primers, a third oligonucleotide labeled with a probe for detection, Taq polymerase and the other buffers, salts and dNTPs required for PCR. The kit can also use other methods for detection of the transcripts such as direct hybridization of the BTM RNA with labeled probes or branched DNA technology; and (vi) oligonucleotides and probe for the detection of transcripts from a highly transcribed gene, such as β-actin: to serve as a quality control measure.

Evaluation of Progression of Bladder Cancer Using BTM ratios

To evaluate the progression of bladder tumours, samples of tissue are obtained by biopsy of bladder wall or samples of urine are collected over time from a patient having bladder cancer. Evaluation of the ratio of BTMs or combinations thereof are made for samples taken at different times. BTM ratios within a specified range are indicative of progression of bladder cancer.

Evaluation of Therapy of Bladder Cancer Using BTM Ratios

To evaluate the efficacy of therapy for bladder tumours, samples of tissue and/or urine are obtained before treatment is initiated. The baseline levels of one or more BTMs are determined, as are ratios of various BTMs with respect to each other. Treatment is initiated, and can include any therapy known in the art, including surgery, radiation therapy or chemotherapy as appropriate to the type and stage of the disease. During the course of therapy, samples of tissue and/or urine are collected and analyzed for the presence and amount of BTMs. Ratios of various BTMs are determined and results are compared to: (1) the patient's baseline levels before treatment or (2) normal values obtained from a population of individuals not having bladder cancer.

Use of BTM Ratios to Monitor the Progression of TCC Therapies

In addition to the rapid diagnosis and early detection of TCC; BTM marker ratios detected in either tissue, serum or urine can be used to monitor a patient's response to therapy. In these applications, urine and/or serum samples can be taken at intervals following the initiation of systemic, intra-vesicular or intravascular chemotherapy, radiotherapy or immunotherapy. A change in marker ratio can indicate a reduction in tumour size, indicative of effective treatment. The rate of change can be used to predict the optimum therapeutic dose for each patient or treatment.

Use of BTM Regression Analyses

In addition to the BTM ratios, regression or classification analyses that include high and low expressing BTM family members can be used for the applications described above.

Markers evaluated are selected from known human genes. The genes evaluated are indicated in FIGS. 3 and 4. Included in FIGS. 3 and 4 are the name of the gene, the HUGO identifier, MWG oligo number, NCBI mRNA reference sequence number and the protein reference number. The full length sequences can be found at http://www.ncbi.nlm.nih.gov/entrez/.

EXAMPLES

The examples described herein are for purposes of illustrating embodiments of the invention and are not intended to limit the scope of the invention. Other embodiments, methods and types of analyses are within the scope of persons of ordinary skill in the molecular diagnostic arts and need not be described in detail hereon. Other embodiments within the scope of the art that are based on the teachings herein are considered to be part of this invention.

Methods

Tumour Collection

Bladder tumour samples and non-malignant urothelium samples were collected from surgical specimens resected at Kyoto University Hospital, Japan.

Urine Collection

Urine samples from non-malignant controls and bladder cancer patients were obtained from Kyoto University Hospital, Japan. Healthy control samples were obtained from Japanese volunteers (FIG. 1).

RNA Extraction

Tumour tissues were homogenized in a TriReagent: water (3:1) mix, then chloroform extracted. Total RNA was then purified from the aqueous phase using the RNeasy™ procedure (Qiagen). RNA was also extracted from 16 cancer cell lines and pooled to serve as a reference RNA.

RNA was extracted from urine by mixing the urine sample with an equal volume of lysis buffer (5.64 M guanidine-HCl, 0.5% sarkosyl, 50 mM sodium acetate (pH 6.5) and 1 mM β-mercaptoethanol; pH adjusted to 7.0 with 1.5 M Hepes pH 8). Due to the low amounts of RNA in urine, 7.5 ugs of total bacterial RNA was added to the urine/lysis buffer mix to act as a carrier. Total RNA was then extracted using Trizol and the RNeasy™ procedure. RNA preparations were further purified prior to cDNA synthesis using the Qiagen QIAquick™ PCR purification kit.

RNA was extracted from the blood of three healthy volunteers by performing a Trizol/RNeasy™ extraction on cells enriched from whole blood using sedimentation in 3.6% dextran.

Microarray Slide Preparation

Epoxy coated glass slides (MWG Biotech) were printed with ~30,000 50 mer oligonucleotides (MWG Biotech) using a Gene Machines microarraying robot, according to the manufacturer's protocol.

RNA Labeling and Hybridization cDNA was transcribed from 5 μg total RNA using Superscript II™ reverse transcriptase (Invitrogen) in reactions containing 5-(3-aminoallyl)-2'deoxyuridine-5'-triphosphate. The reaction was then de-ionised in a Microcon column before being incubated with Cy3 or Cy5 in bicarbonate buffer for 1 hour at room temperature. Unincorporated dyes were removed using a Qiaquick column (Qiagen) and the sample concentrated to 15 μl in a SpeedVac. Cy3 and Cy5 labeled cDNAs were then mixed with Ambion ULTRAhyb™ buffer, denatured at 100° C. for 2 min and hybridized to the microarray slides in hybridisation chambers at 42° C. for 16 hours. The slides were then washed and scanned twice in an Axon 4000A™ scanner at two power settings.

Microarray Analysis of Cancer Marker Genes

RNA from 53 bladder tumours and 20 non-malignant ("normal") bladder tissue samples were labeled with Cy5 and hybridized in duplicate or triplicate with Cy3 labeled reference RNA. After normalization, the change in expression in each of 29,718 genes was then estimated by fold change and statistical probability.

Normalisation Procedure

Median fluorescence intensities detected by Genepix™ software were corrected by subtraction of the local background intensities. Spots with a background corrected intensity of less than zero were excluded. To facilitate normalization, intensity ratios and overall spot intensities were log-transformed. The logged intensity ratios were corrected for dye and spatial bias using local regression implemented in the LOCFIT™ package. Logged intensity ratios were regressed simultaneously with respect to overall spot intensity and location. The residuals of the local regression provided the corrected logged fold changes. For quality control, ratios of each normalized microarray were plotted in respect to spot intensity and localization. The plots were subsequently visually inspected for any remaining artifacts. Additionally, an ANOVA model was applied for the detection of pin-tip bias. All results and parameters of the normalization were inserted into a Postgres-database for statistical analysis.

Statistical Analysis

To improve the comparison of measured fold changes between arrays, log 2 (ratios) were scaled to have the same overall standard deviation per array. This standardization reduced the average within-tissue class variability. A ranktest based on fold changes was then used to improve the noise robustness. This test consists of two steps: (i) calculation of the rank of fold change (Rfc) within arrays and ii) subtraction of the median (Rfc) for normal tissue from the median (Rfc) for tumour tissue. The difference of both median ranks defines the score of the fold change rank.

Three additional statistical tests were also performed on standardized data: 1) Two sample student's t-test, 2) the Wilcoxon test and 3) Statistical Analysis of Microarrays (SAM). The most significantly down-regulated genes determined by each of the statistical methods (rank fold change, t-test, Wilcoxon test, and SAM) were given a rank score for each test. All rank scores were then added into one summated rank score.

cDNA Synthesis from Urine RNA

Total urine RNA was annealed to gene-specific primers for each of the bladder tumour markers by incubating at 70° C. then cooling on ice for 2 mins in 50 ul reactions containing forward primers at 0.01 μg/μl. Each cDNA reaction contained annealed RNA and 4 μl of 5× Superscript II reverse transcriptase buffer (Invitrogen, USA), 2 μl of 0.1M DTT (Invitrogen, USA), 0.5 μl of RNase out (40 U/μL), (Invitrogen, USA), 4 μl of 10 mM dNTP (Invitrogen, USA) and 0.5 μl of Superscript II reverse transcriptase (200 U/μl), (Invitrogen, USA) in a final volume of 20 μl. Reactions were incubated at 42° C. for 1 hour, 10 minutes at 70° C. and 1 minute at 80° C. Reactions were cleaned prior to qPCR with Qiagen QIAquick PCR purification columns (Qiagen, Victoria, Australia) and stored at −80° C.

Quantitative Real-Time PCR

Real-time or quantitative PCR (qPCR) is used for absolute or relative quantitation of PCR template copy number. Taqman™ probe and primer sets were designed using Primer Express V 2.0™ (Applied Biosystems). Where possible, all potential splice variants were included in the resulting amplicon, with amplicon preference given to regions covered by the MWG-Biotech-derived microarray oligonucleotide. Primer and probe sequences are shown in FIG. 2. Alternatively, if the target gene was represented by an Assay-on-Demand™ expression assay (Applied Biosystems) covering the desired amplicons, these were used. In the in-house designed assays, primer concentration was titrated using a SYBR green labeling protocol and cDNA made from the reference RNA. Amplification was carried out on an ABI Prism™ 7000 sequence detection system under standard cycling conditions. When single amplification products were observed in the dissociation curves, standard curves were generated over a 625 fold concentration range using optimal primer concentrations and 5'FAM-3'TAMRA phosphate Taqman™ probe (Proligo) at a final concentration of 250 nM. Assays giving standard curves with regression coefficients over 0.98 were used in subsequent analyses.

Assays were performed in 96 well plates. Each plate contained a reference cDNA standard curve, over a 625-fold concentration range. For the urine qPCR, total RNA extracted from ~0.5 mls unfractionated urine was used in each reaction. The ΔCt (target gene Ct-mean reference cDNA Ct) was calculated for each marker, and used in subsequent ratios, regression or classification analysis.

Expression of Markers in Blood

The expression of the markers shown in FIGS. 3 and 4 in whole blood was determined in silico. Microarray probes were linked to UniGene clusters via the GenBank accession numbers of their target mRNAs, and the tissue expression profile from UniGene used to determine the number of expressed sequence tags (ESTs) in blood libraries. Only genes with 0 or 1 expressed sequence tags (EST) are shown in FIG. 4. To confirm the low expression of LTB4DH in whole blood, RT-qPCR was carried out on total RNA extracted from whole blood using the primers and probes shown in FIG. 2. No significant expression was observed (results not shown).

Identification of Down Regulated Bladder Cancer Markers

To identify down-regulated markers of bladder cancer, we performed microarray studies on RNA from 53 bladder tumours and 20 non-malignant bladder tissue samples using 30,000 oligonucleotide chips. FIG. 3 shows the statistical analysis of microarray data for 300 genes that show significant downregulation in bladder cancer tissue compared to non-malignant tissue. FIG. 3 includes the HUGO gene name and symbol, the protein reference sequence number, the NCBI mRNA reference sequence number, the MWG Biotech probe oligonucleotide number, the median fold change in gene expression between tumour and non-malignant tissue, the results of an original unadjusted Student's t-test, the results of the 2-sample Wilcoxon test, the results of the SAM test, and the summated rank score.

Identification of Preferred Under-Expressed Bladder Tumour Markers for Use in Urine Tests for Bladder Cancer Because urinary hematuria is a common co-occurrence with bladder cancer, it is an advantage that bladder cancer markers are not significantly elevated in whole blood. In addition, because the downregulated markers are being used in ratios, regression or classification analysis, it is an advantage that they be present in sufficiently high copy numbers in both tumour cells and non-malignant bladder cells to enable reliable detection in urine. To identify suitable markers, we screened the genes in FIG. 3 for a subset that had little or no representation in blood EST libraries, and had higher than median expression in non-malignant tissue. Median expression was estimated by ranking the 30,000 oligonucleotides on the array by their median intensity in the samples analysed in the microarray study. Markers that met the criteria are shown in FIG. 4. FIG. 4 includes the HUGO gene name and symbol, the protein reference sequence number, the NCBI mRNA reference sequence number, the median fold change, the rank score, the median rank of microarray spot intensity in tumour tissue and non-malignant tissue, and the number of ESTs present in blood EST libraries.

The down regulation observed in the array data was validated by qPCR for three genes shown in FIG. 4, LTB4DH, BAG1 and FLJ21511. These genes were tested on total RNA from 10 tumour samples and 10 non-malignant samples. LTB4DH, BAG1 and F1121511 showed an average downregulation in bladder tumours compared to bladder non-malignant tissue of 2.5 fold, 1.4 fold and 6.1 fold, respectively, in these samples.

qPCR Analysis of Urine using LTB4DH

Figure 7A:
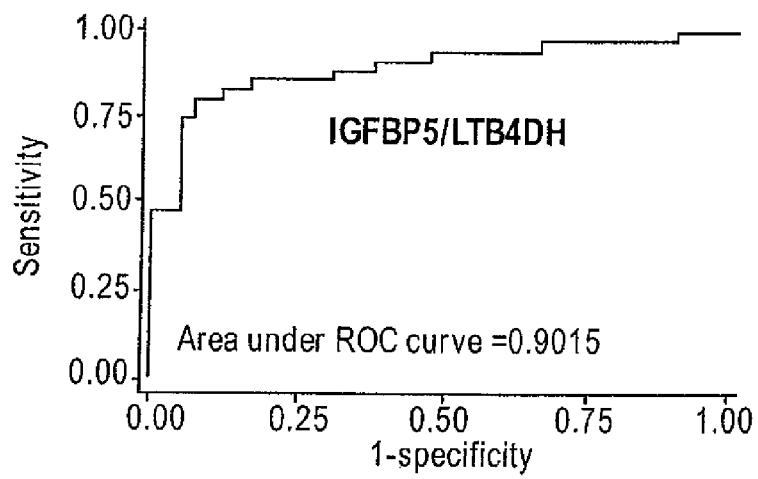
FIG. 7a-c shows ROC curves for the sensitivity and specificity of detection of TCC in urine samples using ratios that include LTB4DH. 7a. IGFBP5/LTB4DH; 7b. MDK/LT4BDH; 7c. HoxA13/LTB4DH.
Figure 7B:
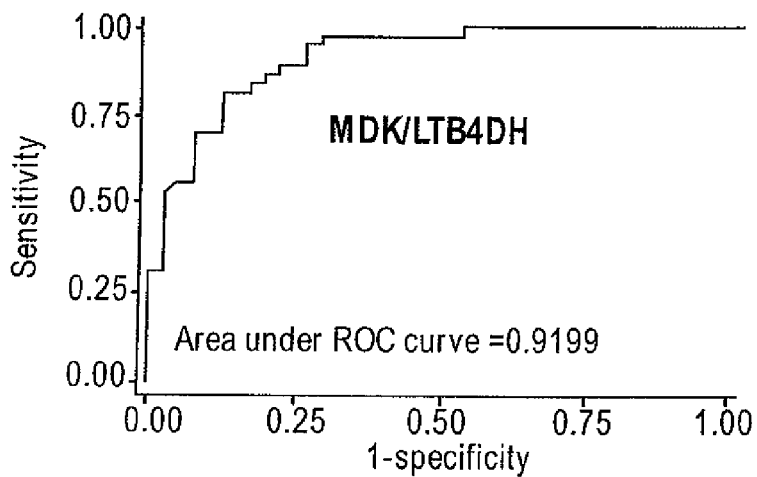
Figure 7C:
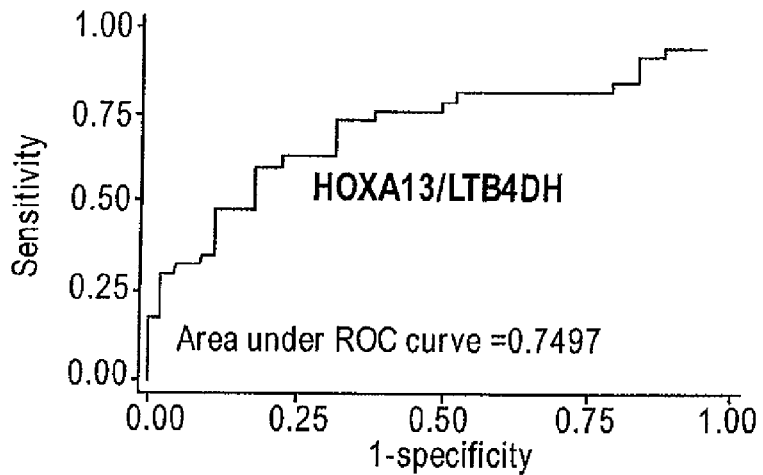

Urine from TCC patients and controls with non-malignant urological conditions was collected by either voiding or catheterisation. Total RNA was extracted from the voided urine of 42 controls and the voided or catheterised urine of 37 TCC patients and used in quantitative RT-PCR using primers and probes for LTB4DH and three over-expressed markers, IGFBP5, MDK and HoxA13. The ΔCt ratios were determined for IGFBP5/LTB4DH, MDK/LTB4DH and HoxA13/LTB4DH. This data is illustrated by the box plots in FIG. 5, which show a clear difference in the spread of data between the urine samples from controls and TCC patients for each of the three tests. The most accurate test was IGFBP5/LTB4DH which demonstrated sensitivity and specificity of 87% and 88% in this sample cohort, respectively (FIG. 6a). To illustrate the correspondence between sensitivity and specificity for each of these tests, ROC curves are shown in FIG. 7. The areas under the curve for IGFBP5/LTB4DH, MDK/LTB4DH and HoxA13/LTB4DH are 0.9223, 0.9199, and 0.7497, respectively. These areas, which measure test accuracy, indicate that all three ratios with LTB4DH are useful tests, in particular IGFBP5/LTB4DH and MDK/LTB4DH.

To increase the sensitivity and specificity of TCC detection, combinations of two tests were used. The optimal sensitivities and specificities of these test combinations are shown in FIG. 6b. FIG. 8a-f shows the separation of data in 2 dimensional space for each of the three tests using LTB4DH and BAG1. This data shows that combinations of two or more tests that include either of the downregulated BTMs LTB4DH or BAG1, are able to achieve sensitivities and specificities of over 90%. Moreover, because these, tests are measuring simple gene expression signatures and not absolute levels of markers, they will be robust to variations in urine concentration.

To demonstrate the robustness of tests involving ratios with LTB4DH to urine concentration, the levels of IGFBP5 alone (ΔCt) and IGFBP5/LTB4DH were plotted as a function of urine concentration (FIG. 9a-b) and trendlines fitted to the data. It can be seen that for both urine samples from non-malignant controls and patients with TCC, there is a decrease in the IGFBP5 ΔCt with increasing urine concentration that is absent in the IGFBP5/LTB4DH ratio. The effect is most pronounced with the non-malignant samples because of the absence of other influences such as tumour size and tumour heterogeneity in the expression of IGFBP5 and LTB4DH.

In some instances, when single markers are used in bladder cancer assays, the method of urine sample collection can affect the amount of marker detected due to variations in the number of exfoliated bladder cells collected. This bias could lead to false positive or false negative results in a small proportion of samples. The use of ratios including LTB4DH or other low-expressing genes should provide a method to compensate for different methods. To test this hypothesis, samples collected from TCC patients by either simple voiding (nine samples) or catheterisation (28 samples) were tested for the presence of TCC markers and LTB4DH. Analysis of the TCC markers alone showed that the voided samples were more heavily represented at the lower end of the range of data (higher Ct), consistent with a lower average number of exfoliated cells in these samples compared to the catheterised samples. This is illustrated in the self-self scatter plots for IGFBP5, MDK and HoxA13 in FIG. 10a-c. In contrast, when ratios between these markers and LTB4DH were calculated, the voided and catheterised samples were spread over similar ranges of Ct ratios (FIG. 10d-f), illustrating that the calculation of gene expression signatures between high expressing markers and low expressing markers such as LTB4DH compensate for variations in marker levels introduced by different urine sampling methodologies.

Urine samples from patients with low grade tumours are often borderline in their accumulation of BTMs due to the presence of only small numbers of exfoliated cells in these samples. These samples are therefore at high risk of being incorrectly classified due to variations in sampling method or urine concentration.

The utility of gene expression ratios that incorporate down-regulated genes for the detection of TCC is therefore likely to be pronounced when applied to the detection of low grade TCC. To demonstrate this effect, a cohort of voided 43 urine samples from patients with low grade TCC and 123 controls were tested with the markers IGFBP5, HoxA13 and LTB4DH. The clinical characteristics of the cohort are summarised in FIG. 13. The qPCR data for IGFBP5 and HoxA13 were analysed alone and in ratios with LTB4DH using the area under the ROC curve as a measure of test accuracy (STATA statistics package). The results are summarized in FIG. 14. Using the IGFBP5 marker, LTB4DH increased the accuracy of detection of low grade (grade 1-2) stage Ta TCCs by 9% and low grade TCCs of any stage by 8%. The accuracy of HoXA13 testing of low grade stage Ta TCCs was increased by 3%.

Linear Discriminate Analysis of qPCR Data using LTB4DH

Linear discriminate analysis (LDA) is a statistical technique (Fisher R. A. "The Use of Multiple Measurements in Taxonomic Problems", Annals of Eugenics 7 179 (1936)) in which a linear combination of variables is generated, such that there is maximal separation between two or more groups. This linear combination of variables is termed the "linear discriminant", which is a linear function of the input variables that maximally separates the classes of the data set. The ability of LDA (or any other classification technique) to characterise a particular dataset, such as qPCR data, can be tested using cross-validation. In this method, part of the dataset is used to generate a classifier, and part of the dataset is used to measure the effectiveness of that classifier. The partitioning of the dataset into training and testing sets can be repeated multiple times (each time generating a new classifier). In k-fold cross-validation, the dataset is split k-wise, and each subset is used as the testing set in one of k rounds of training and validation. This can be extended to leave-one-out cross-validation (LOOCV) where each sample is classified according to a classifier generated from the remaining samples in the dataset ("leaving one out"; leaving out the sample which is being tested).

LDA and LOOCV were used to illustrate the utility of the downregulated BTM, LTB4DH, in improving the diagnosis of TCC. qPCR was first carried out on the cohort of control and TCC urine samples described in FIG. 13 which were supplemented with an additional 30 grade 3 tumours (5>stage 1, 13=stage 1, 4=Tis, and 8=Ta). Combinations of the six genes LTB4DH, MDK, 1GFBP5, HOXA13, TOP2a and CDC2 were tested for classifier performance, as judged by LOOCV. The posterior probability (that the sample "left out" was a TCC sample) was used to generate ROC curves using the ROCR package of the R statistical programming environment. The sensitivity of the classifier for a given specificity was obtained by reference to the appropriate ROC curve.

The sensitivity of detection of TCC using combinations of upregulated BTMs with and without LTB4DH was determined at a specificity of 85%. The results of this analysis are shown in FIG. 15. It can be seen that the addition of LTB4DH to assays including combinations of the upregulated BTMs MDK, IGFBP5, Top2a, cdc2 and HoxA13 increased the overall sensitivity by 1-2% and the sensitivity of detection of Stage Ta tumours, grade 1-2 tumours and grade 3 tumours by up to 3%.

Wherein in the foregoing description reference has been made to integers or components having known equivalents, such equivalents are herein incorporated as if individually set fourth.

Although the invention has been described by way of example and with reference to possible embodiments thereof, it is to be appreciated that improvements and/or modifications may be made without departing from the scope or the spirit thereof.

INDUSTRIAL APPLICABILITY

Methods for detecting BTM family members include detection of nucleic acids, proteins and peptides using microarray and/or real time PCR methods. The compositions and methods of this invention are useful in diagnosis of disease, evaluating efficacy of therapy, and for producing reagents and test kits suitable for measuring expression of BTM family members.

The invention claimed is:

1. A testing device, comprising: a substrate divided into a plurality of locations thereon wherein,
   i) one of said plurality of locations has an oligonucleotide having the sequence of SEQ ID NO: 1, SEQ ID NO: 2, or SEQ ID NO: 3 that bind to an oligonucleotide of IGFBP5;
   ii) another one of said locations having an oligonucleotide that binds to an oligonucleotide of LTB4DH;
   iii) another one of said locations having an oligonucleotide that binds to an oligonucleotide of HOXA13;
   iv) another one of said locations having an oligonucleotide that binds to an oligonucleotide of MDK;
   v) another of said locations having an oligonucleotide that binds to an oligonucleotide of CDC2; and
   vi) another one of said locations having an oligonucleotide that binds to an oligonucleotide of BAG 1
   wherein each of the oligonucleotides are immobilized on the substrate.

2. A method for determining the presence of Transitional Cell Carcinoma (TCC) of the bladder in a subject, comprising:
   (a) providing a device of claim 1;
   (b) providing a sample of urine from the subject;
   (c) providing a set of samples of urine from a plurality of subjects not having TCC;
   (d) for each of steps (b) and (c),
      (i) applying mRNA or cDNA made from mRNA obtained from said sample obtained in steps (b) to said device of step (a);
      (ii) applying mRNA or cDNA made from mRNA obtained from each of said set of subjects in step (c);
   (e) applying a plurality of labeled oligonucleotides each of which binds to one of the genetic markers on said substrates;
   (f) washing said substrates under stringent conditions;
   (g) quantifying the amount of each of said labeled oligonucleotides of step (e);
   (h) normalizing said amounts of each of said labeled oligonucleotides of step (g) thereby providing a measures of expression of each of said genetic markers in said sample and said group of said subjects in step (d)(ii);
   (i) for said sample and said plurality of subjects not having TCC, calculating the ratios of expression of IGFBP5/LTB4DH, or the ratios of expression of HOXA13/LTB4DH, or the ratios of expression of MDK/LTB4DH;
   (j) if one or more of the ratios of said sample obtained in step (i) are lower than the ratios of said genetic markers for said plurality of subjects not having TCC, said patient has TCC.

3. The device of claim 1, wherein said oligonucleotide that binds to LTB4DH comprises SEQ ID NO: 4, or SEQ ID NO: 5, or SEQ ID NO: 6.

4. The device of claim 1, wherein said oligonucleotide that binds to CDC2 comprises SEQ ID NO: 7, or SEQ ID NO: 8.

5. The device of claim 1, wherein said oligonucleotide that binds to IGFBP5 comprises SEQ ID NO: 1.

6. The device of claim 1, wherein said oligonucleotide that binds to IGFBP5 comprises SEQ ID NO: 2.

7. The device of claim 1, wherein said oligonucleotide that binds to IGFBP5 comprises SEQ ID NO: 3.

8. The device of claim 1, wherein said oligonucleotide that binds to LTB4DH comprises SEQ ID NO: 4.

9. The device of claim 1, wherein said oligonucleotide that binds to LTB4DH comprises SEQ ID NO: 5.

10. The device of claim 1, wherein said oligonucleotide that binds to LTB4DH comprises SEQ ID NO: 6.

11. The device of claim 1, wherein said oligonucleotide that binds to CDC2 comprises SEQ ID NO: 7.

12. The device of claim 1, wherein said oligonucleotide that binds to CDC2 comprises SEQ ID NO: 8.

* * * * *

UNITED STATES PATENT AND TRADEMARK OFFICE
CERTIFICATE OF CORRECTION

Page 1 of 1

PATENT NO. : 9,702,009 B2
APPLICATION NO. : 12/843435
DATED : July 11, 2017
INVENTOR(S) : Parry John Guilford It is certified that error appears in the above-identified patent and that said Letters Patent is hereby corrected as shown below:

In the Claims

Claim 2 Column 28 Line 11: "(i)" should be -- (j) --

Signed and Sealed this
Twenty-second Day of August, 2017

Joseph Matal
*Performing the Functions and Duties of the*
*Under Secretary of Commerce for Intellectual Property and*
*Director of the United States Patent and Trademark Office*